US007183067B2

(12) United States Patent
Suda et al.

(10) Patent No.: US 7,183,067 B2
(45) Date of Patent: Feb. 27, 2007

(54) VERSATILE LINKER COMPOUND, LIGAND, AND PRODUCING METHOD THEREOF

(75) Inventors: Yasuo Suda, Kagoshima (JP); Akio Arano, Nagoya (JP); Hideki Hayashi, Tokushima (JP); Shoichi Kusumoto, Minoo (JP); Michael Sobel, East Seattle, WA (US)

(73) Assignees: Japan Science and Technology Agency, Kawaguchi (JP); National University Corporation Kagoshima University, Kagoshima (JP)

( * ) Notice: Subject to any disclaimer, the term of this patent is extended or adjusted under 35 U.S.C. 154(b) by 30 days.

(21) Appl. No.: 10/526,938

(22) PCT Filed: Aug. 6, 2003

(86) PCT No.: PCT/JP03/09973

§ 371 (c)(1),
(2), (4) Date: Mar. 8, 2005

(87) PCT Pub. No.: WO2004/022565

PCT Pub. Date: Mar. 18, 2004

(65) Prior Publication Data

US 2006/0014220 A1    Jan. 19, 2006

(30) Foreign Application Priority Data

Sep. 9, 2002 (JP) ............................ 2002-263414
Jul. 2, 2003 (JP) ............................ 2003-190637

(51) Int. Cl.
*G01N 33/53* (2006.01)
*G01N 33/532* (2006.01)
*G01N 33/547* (2006.01)
*C12P 7/58* (2006.01)
*C07K 1/13* (2006.01)

(52) U.S. Cl. ..................... 435/7.5; 435/7.1; 435/7.92; 435/137; 435/961; 435/970; 436/532; 436/544; 530/402; 530/411; 530/413; 530/813

(58) Field of Classification Search ............... 435/7.1, 435/7.75, 7.92, 137, 961, 970, 7.5; 530/402, 530/411, 413, 813; 436/544, 532

See application file for complete search history.

(56) References Cited

U.S. PATENT DOCUMENTS 5,714,166 A * 2/1998 Tomalia et al. ............ 424/486
5,886,143 A   3/1999 Theodore et al.

FOREIGN PATENT DOCUMENTS

| JP | 07-252288 A | 10/1995 |
|---|---|---|
| JP | 07-252288 A | 10/1995 |
| JP | 2002-080488 A | 3/2002 |
| JP | P2002-80488 A * | 3/2002 |
| JP | 2003-083969 A | 3/2003 |
| JP | 2003-83969 A | 3/2003 |
| WO | WO 96/17613 | 6/1996 |

OTHER PUBLICATIONS

"Nature of the Interaction of Heparin with Acidic Fibroblast Growth Factor", H. Mach et al., Biochemistry 1993, 32, pp. 5480-5489.
"The Lectin-Binding Properties of Six Generations of Mannose-Functionalized Dendrimers", E. K. Woller et al., Organic Letters 2002, vol. 4, No. 1, pp. 7-10.
"A Quantitative Estimation of Carbohydrate—Carbohydrate Interaction Using Clustered Oligosaccharides of Glycolipid Monolayers and of Artificial Glycoconjugate Polymers by Surface Plasmon Resonance", K. Matsuura et al., J. Am. Chem. Soc. 2000, 122, pp. 7406-7407.
"Synthesis and biological activity of oligomer-model compounds containing units of key platelet-binding disaccharide of heparin", S. Koshida et al., Tetrahedron Letters, 40, 1999, pp. 5725-5728.
"A New Class of Polymers: Starburst-Dendritic Macromolecules", D.A. Tomalia et al., Polymer Journal, vol. 17, No. 1, 1985, pp. 117-132.
"Polynitrile- and Polyamine-Functional Poly (trimethylene imine) Dendrimers", C. Worner et al., Angew. Chem. Int. Ed. Engl. 1993, 32, No. 9, pp. 1306-1311.
"Assembly of saccharide by multi-functional linker and application to surface plasmon resonance analysis and affinity chromatography", H. Hayashi et al., Tentative Lecture Proceedings, Chemical Society of Japan, Mar. 3, 2003, vol. 83rd, No. 2, p. 952 (2G2-48).
"Synthesis of a novel linker module for assembly and immobilization of reducing saccharides", H. Hayashi et al., Tentative Lecture Proceedings, Chemical Society of Japan, Sep. 10, 2002, vol. 82nd, p. 137 (1C1-12).
"Synthesis, designed assembly and biotinylation of sulfated oligo saccharide and its application to surface plasmon resonance", H. Hayashi et al., Tentative Lecture Proceedings, Chemical Society of Japan, 2001, vol. 79th, No. 2, p. 1042 (4G304).
"Synthesis of Sugar Arrays in Microtiter Plate", F. Fazio et al., J. Am. Chem. Soc. 2002, 124, pp. 14397-14402.
"Carbohydrate Chips for Studying High-Throughput Carbohydrate-Protein Interactions", S. Park et al., J. Am. Chem. Soc. 2004, 126, pp. 4812-4819.

(Continued)

*Primary Examiner*—Christopher L. Chin
*Assistant Examiner*—Shafiqul Haq
(74) *Attorney, Agent, or Firm*—Harness, Dickey & Pierce, P.L.C.

(57) ABSTRACT

A versatile linker compound has a structure represented by following general formula (1), wherein Y has a structure represented by O or NH, and X has a structure serving as a multi-branched moiety including four hydrocarbon derivative chains each of which has an aromatic amino group at an end thereof, and may or may not have a carbon-nitrogen bond in a backbone thereof. With the versatile linker compound, sugar molecules can be two-dimensionally arranged on a surface of a protein-analyzing supporter with high reproducibility. Also, a ligand includes the versatile linker compound and a sugar molecule introduced thereinto.

18 Claims, 9 Drawing Sheets

OTHER PUBLICATIONS

"Nonstatistical binding of a protein of clustered carbohydrates", N. Horan et al., PNAS, Oct. 12, 1999, vol. 96, No. 21, pp. 11782-11786.

"Carbohydrate Arrays for the Evaluation of Protein Binding and Enzymatic Modification", B. T. Houseman et al., Chemistry & Biology vol. 9, Apr. 2002, pp. 443-454.

"Using Model Substrates To Study the Dependence of Focal Adhesion Formation on the Affinity of Integrin—Ligand Complexes", M. Kato et al., Biochemistry 2004, 43, pp. 2699-2707.

"Probing Protein—Carbohydrate Interactions with Microarrays of Synthetic Oligosaccharides", D. M. Ratner et al., ChemBioChem. 2004, 5, pp. 379-382.

"Oligosaccharide microarrays to decipher the glycol code", T. Feizi et al., Nature Reviews, Jul. 2004, vol. 5, pp. 582-588.

Hayashi Kusumotoet al., "Taki Yotogata Linker o Mochiita Tosa no Shugoka to Hyomen Plasmon Kyomeiho Kaiseki Narabi ni Affinity Chromatography eno Oyo", CSJ: The Chemical society of Japan Yokoshu, Mar. 3, 2003, vol. 83rd, No. 2, p. 952, G2-48.

Hayashi Kusumoto et al., "Tosa no Shugoka to Koteika no Tame no Shinki Linker Bunshi no Gosei", CSJ: The Chemical Society of Japan Koen Yokoshu, Sep. 10, 2002, vol. 82nd, p. 137, 1 C1-12.

Hayashi Arano et al., "Ryusanka Oligo-to no Shugoka, Biotin-ka oyobi Sono Hyomen Plasmon Kyomei eno Oyo" CSJ: The Chemical Society of Japan Yokoshu, 2001, vol. 79th, No. 2, p. 1042, 4G304.

Fukase K. et al., Functional flurescence labeling of carbohydrates and its use for preparation of neoglycoconjugates:, J. Carbohydrate Chemistry, 1994, vol. 13, No. 5, pp. 715 to 736; full text; p. 723.

Lindhorst T.K. et al., "Glycocoating of oligovalent amines: synthesis of thioureabridged cluster glycosides from glycosyl isothiocyanates", Angewandte Chemie, International Edition in English, 1996, vol. 35, No. 17, pp. 1953 to 1956.

Wells N.J. et al., "Solid-phase dendrimer synthesis", Biopolymers, 1999, vol. 47, No. 5, pp. 381 to 396.

Korean Office Action dated May 26, 2006 and translation.

* cited by examiner

US 7,183,067 B2

VERSATILE LINKER COMPOUND, LIGAND, AND PRODUCING METHOD THEREOF

RELATED APPLICATIONS

This is a US national phase filing under 35 U.S.C. Ø 371 of PCT/JP03/09973 filed Aug. 6, 2003 and claims priority from JP 2002-263414 filed Sep. 9, 2002 and JP 2003-190637 filed Jul. 2, 2003.

1. Technical Field

The present invention relates to a versatile linker compound used to introduce a sugar suitably and effectively when using a sugar in chip technology, chromatography, a bioprobe, and the like. The present invention also relates to a ligand which includes the versatile linker compound and a sugar introduced thereinto, a ligand carrier, and producing methods of such ligands and ligand carriers.

2. Background Art

Various intravital saccharides, interacting with a specific protein, play an important role in a mechanism for sustaining activities and lives of living organisms. Therefore, the study of an interaction between a sugar and a protein is important in terms of examining a biological activity of a sugar.

A protein which interacts with a sugar is detected for example by the following method. That is, the surface plasmon resonance (hereinafter referred to as SPR) method, with a sensor chip which has a sugar on a surface thereof, can be used to examine biochemical bonding of the sugar with a protein. Also, immobilization of a sugar onto an affinity chromatography carrier makes it possible to separate and purify a protein which specifically interacts with the sugar. Furthermore, the use of a sugar as a bioprobe used in genetic engineering makes it possible to detect a protein which interacts with the sugar.

As disclosed in "*Tentative Lecture Proceedings II in the 79th Spring Meeting*, Chemical Society of Japan, Mar. 15, 2001, p. 1042," the inventors have so far found a linker compound capable of taking in various oligosaccharides in one step into a protein-analyzing supporter (e.g., the SPR sensor chip and the affinity chromatography carrier) for immobilization. The inventors have also found a ligand which includes the linker compound and an oligosaccharide introduced thereinto.

The linker compound has an aromatic amine moiety and a biotin moiety. The aromatic amine moiety is used for introducing an oligosaccharide; the biotin moiety is used for immobilizing the oligosaccharide onto a protein-analyzing supporter by utilizing the biotin-streptoavidin (or avidin) bond. Therefore, the linker compound makes it possible to immobilize an oligosaccharide onto a protein-analyzing supporter.

Meanwhile, a single oligosaccharic molecule is not active enough. Therefore, it is usually necessary to collect and introduce three or more units of oligosaccharides onto the protein-analyzing supporter when evaluating a biological activity of an oligosaccharide. Accordingly, when the linker compound is used to immobilize an oligosaccharide onto the supporter, three or more units of oligosaccharides must be collected by collecting on a surface of the supporter a ligand which includes the linker compound and a sugar introduced thereinto.

It is to be noted that Japanese Laid-Open Publication No. 080488/2002 (Tokukai 2002-080488; published on Mar. 19, 2002) discloses a collecting method of a sugar chain, and a synthesis method of a linker for the sugar chains. Also, Japanese Laid-Open Publication No. 83969/2003 (Tokukai 2003-83969; published on Mar. 19, 2003) discloses an immobilizing method of a sugar chain, and a synthesis method of a linker and a sugar chain ligand thereof. Also, "H. Mach, D. B. Volkin, C. J. Burke, C. R. Middaugh, R. J. Linhardt, J. R. Fromm, D. Loganathan, Biochemistry, 32, 5480–5489 (1993)" discloses analyzing an interaction between a sugar chain immobilized on a chip and a protein, with the use of the surface plasmon resonance method. Also, "Eric K. Wollker and Marry J. Cloninger, Org. Lett., 4, 7–10 (2000)" discloses an effect of a molecule which includes collected sugar chains. Also, "K. Matuura, H. Kitakouji, A. Tsuchida, N. Sawada, H. Ishida, M. Kiso and K. Kobayashi, J. Am. Chem. Soc., 122, 7406–7407 (2000)" and "S. Koshida, Y. Suda, Y. Fukui, J. Orms by, M. Sobel, S. Kusumoto, Tetrahedron Lett., 40, 5725–5728 (1999)" discloses a collecting method of sugar chains. Also, "D. H. Tomalia, H. Barker and J. Roeck, Polymer. Jornal., 17, 117–132 (1985)" and "Christof Worner and Rolf Mulha upt, Angew. Chem. Int. Ed. Engl., 32, 1306–1311 (1993)" discloses a synthesizing method of a versatile linker molecule.

The use of a ligand which includes the conventional linker compound makes it possible to collect and arrange sugar chains of an oligosaccharide two-dimensionally on a surface of a sensor chip. However, there is a technical problem left in that it is difficult to control a collected state of the sugar chains so that the sugar chains can be arranged with high reproducibility.

That is, in order to precisely observe a biological activity of the oligosaccharide by using an oligosaccharide immobilized on a surface of a protein-analyzing supporter, it is necessary to observe with high reproducibility an interaction between the oligosaccharide and a protein, with the sugar chains of the oligosaccharide collected uniformly. However, when the conventional ligand is used, a collected state of sugar chains of three or more units of oligosaccharides becomes dependent on a collected state of the ligand. In this case, the same collected state may not always be obtained for the sugar chains of three or more units of oligosaccharides. When the sugar chains of the oligosaccharides are collected differently, the interaction between the oligosaccharides and proteins will be observed differently. As a result, it becomes difficult to evaluate biological activities of oligosaccharides with high reproducibility.

The present invention was made to solve the above problems. It is an object of the present invention to provide a novel versatile linker compound with which sugars can be two-dimensionally arranged on a surface of a protein-analyzing supporter with high reproducibility. The present invention also provides a novel ligand which includes the linker compound and a sugar molecule introduced thereinto, a ligand carrier, and a producing method thereof. The present invention further provides a method for measurement of an interaction between a sugar molecule and other substances with the use thereof.

DISCLOSURE OF INVENTION

The inventors diligently studied to solve the above problems. As a result, the inventors found a novel versatile linker compound which has four aromatic amino groups serving as a moiety capable of taking in four or more units of sugar molecules. The novel versatile linker compound also has a biotin moiety or an iminobiotin moiety serving as a moiety capable of forming a bond with a protein-analyzing supporter used to detect and separate a protein which specifically interacts with a sugar molecule. The inventors also found that the novel versatile linker compound can be used to arrange four or more units of sugar molecules two-dimensionally on the supporter with high reproducibility, thereby completing the present invention.

That is, in order to solve the above problems, a versatile linker compound (hereinafter referred to as a linker compound) has a structure represented by following general formula (1), where Y has a structure represented by O or NH, and X has a structure serving as a multi-branched structure moiety including four hydrocarbon derivative chains, wherein the hydrocarbon derivative chains each include an aromatic amino group at an end thereof, and may or may not include a carbon-nitrogen bond in a backbone thereof.

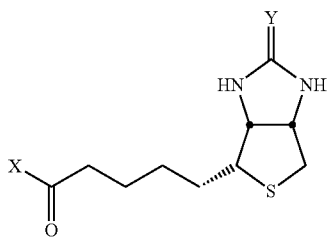

(1)

Each of the hydrocarbon derivative chains is a hydrocarbon chain, consisting of carbon and hydrogen, part of whose carbon and hydrogen may be replaced with another atom and a substituent. That is, the hydrocarbon derivative chain is a hydrocarbon chain, having an aromatic amino group at an end thereof, part of whose carbon-carbon bond (C—C bond), serving as a backbone structure of the hydrocarbon chain, may be replaced with a carbon-nitrogen bond (C—N bond), a carbon-oxygen bond (C—O bond), and an amide bond (CO—NH bond).

According to the above arrangement, the linker compound has a biotin moiety serving as a moiety immobilizable onto the protein-analyzing supporter. The biotin moiety exhibits a high affinity for streptoavidin or avidin (hereinafter referred to as avidin). Therefore, since a biotin-avidin bond is formed on a surface of a supporter which includes avidin immobilized thereon, the linker compound can be easily immobilized onto the surface of the supporter.

Further, the linker compound has an aromatic amino group serving as a moiety capable of easily taking in various sugar molecules. Since the aromatic amino group is included in each hydrocarbon derivative chain, four or more units of sugar molecules can be introduced into the linker compound. Also, since a sugar molecule so introduced is introduced in one linker compound, four or more units of sugar molecules so introduced can be kept at a predetermined interval. This makes it possible to obtain with high reproducibility an arrangement of a sugar molecule introduced onto a protein-analyzing supporter.

Moreover, the use of the linker compound makes it possible to collect four or more units of sugar molecules on the surface of the supporter and therefore arrange a sugar molecule with high reproducibility, thereby making it possible to obtain a sufficient biological activity of a sugar molecule. This makes it possible to detect an interaction between a sugar molecule and a protein and evaluate a biological activity of a sugar molecule with high reproducibility.

In a linker compound represented by general formula (1), it is preferable that X have a structure represented by following general formula (2), wherein $m^1$, $m^2$, $n^1$, $n^2$, $p^1$, $p^2$, $p^3$, and $p^4$ are independently an integer of 1 to 6.

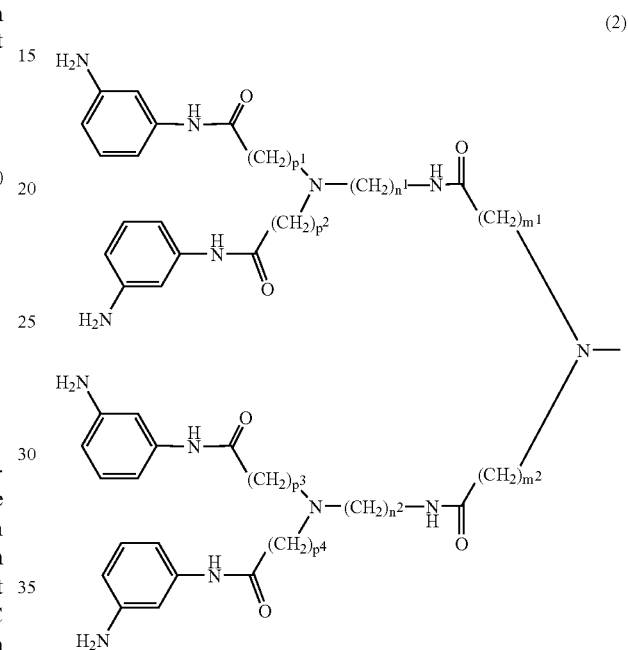

(2)

Since X of the linker compound has the four hydrocarbon derivative chains, the linker compound makes it possible to introduce four or more units of sugar molecules onto the supporter. Therefore, the use of the linker compound makes it possible to control an interval between sugar molecules introduced on the surface of the supporter so as to collect the sugar molecules, thereby making it possible to obtain an arrangement of the sugar molecules on the surface of the supporter with high reproducibility.

Therefore, the use of the linker compound makes it possible to obtain a biological activity of a sugar molecule with high reproducibility. This makes it possible to suitably detect a specific interaction between various sugar molecules and a protein by using SPR and affinity chromatography, which utilize the biological activities of the sugar molecules, a bioprobe, and the like.

Further, in order to solve the above problems, a ligand of the present invention includes the aromatic amino group of any one of the linker compounds and a sugar molecule introduced into the aromatic amino group.

Specifically, it is preferable the ligand have a structure represented by following general formula (3), wherein $m^1$, $m^2$, $n^1$, $n^2$, $p^1$, $p^2$, $p^3$, and $p^4$ are independently an integer of 1 to 6.

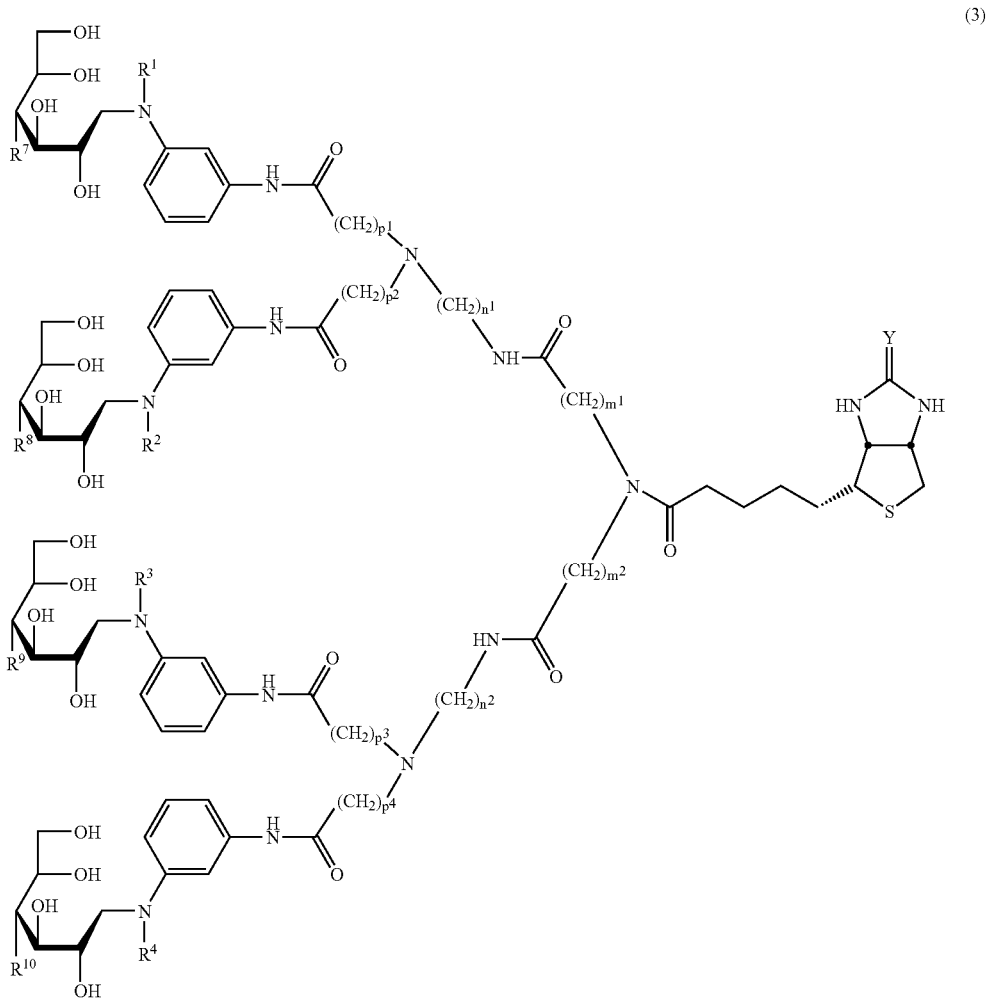

(3)

where Y has a structure represented by O or NH, and $R^1$, $R^2$, $R^3$, and $R^4$ independently has a structure represented by

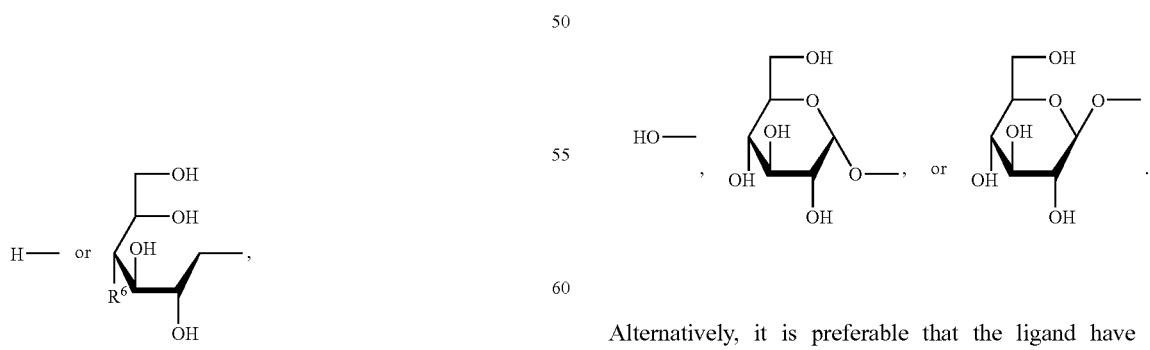

and $R^6$, $R^7$, $R^8$, $R^9$, and $R^{10}$ have a structure selected from the group consisting of Alternatively, it is preferable that the ligand have a structure represented by following general formula (4), wherein Y has a structure represented by O or NH, and $m^1$, $m^2$, $n^1$, $n^2$, $p^1$, $p^2$, $p^3$, and $p^4$ are independently an integer of 1 to 6.

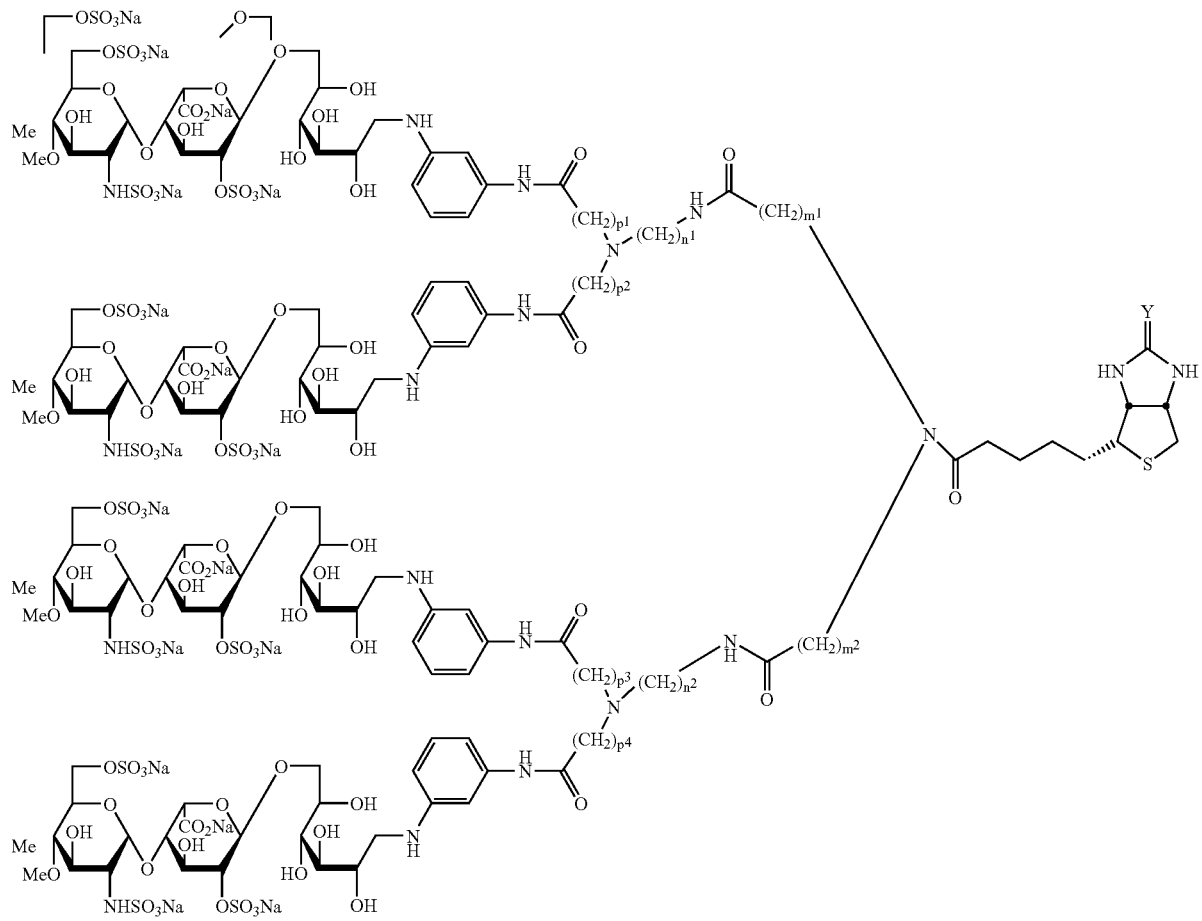

(4)

The use of any one of the ligands makes it possible to immobilize four (in case of a ligand having a structure represented by general formula (4)) or more (in case of a ligand having a structure represented by the general formula (3)) units of sugar molecules onto the surface of the protein-analyzing supporter. Also, since one ligand has four or more units of sugar molecules, the ligand can not only collect four or more units of sugar molecules two-dimensionally on the surface of the supporter but also arrange them with high reproducibility. Therefore, the use of the ligand makes it possible to effectively detect a specific interaction between various sugar molecules and a protein by SPR, affinity chromatography, a bioprobe, and the like.

Further, in order to solve the above problems, a producing method of a linker compound of the present invention includes the steps of: carrying out a condensation reaction between a biotin-containing compound and an amine compound including four branched chains each having an aromatic amino group end protected by a protecting group; and deprotecting the protecting group at the aromatic amino group end.

The biotin-containing compound is activated by the introduction of a substituent into a biotin structure or an iminobiotin structure so as to be able to react with a secondary amino group of an amine compound.

The above method makes it possible to obtain a linker compound of the present invention which has a biotin moiety and an aromatic amino group. The biotin moiety can be immobilized to a protein-analyzing supporter which includes avidin immobilized thereon. The aromatic amino group can easily introduce a sugar molecule.

Further, a producing method of a ligand of the present invention includes the step of carrying out a reductive amination reaction by using any one of the linker compounds and a sugar molecule.

The above method causes a reductive amination reaction to easily introduce a sugar molecule into a linker compound, thereby making it possible to obtain a ligand of the present invention.

Further, a sugar molecule introducing method of the present invention includes the step of causing a solution containing any one of the ligands to come into contact with a supporter including streptoavidin or avidin immobilized on a surface thereof.

The above method binds a biotin moiety or an iminobiotin moiety of the ligand (linker compound included in the ligand) to streptoavidin or avidin on the surface of the supporter so as to immobilize the ligand onto the surface of the supporter. Therefore, a sugar molecule binding to a linker compound can be arranged on a surface of a supporter by a simple method of causing a solution including a ligand to come into contact with a supporter.

Further, a ligand carrier of the present invention includes any one of the ligands immobilized on a surface of a supporter through a biotin-avidin bond formed between a biotin moiety or iminobiotin moiety and streptoavidin or avidin.

Since the above arrangement makes it possible to immobilize a ligand firmly onto a surface of a supporter through a biotin-avidin bond, i.e., a bonding of a biotin moiety or an iminobiotin moiety to streptoavidin or avidin, the above arrangement makes it possible to provide a ligand carrier which includes a plurality of sugar molecules arranged two-dimensionally on a surface of a supporter with high reproducibility. Therefore, the use of the ligand carrier makes it possible to observe with high reproducibility an interaction between the sugar molecules included in the ligand and substances such as proteins, thereby making it possible to quantitatively evaluate biological activities of the sugar molecules.

Further, a method for a measurement of surface plasmon resonance of the present invention detects an interaction of a sugar molecule by using a sensor chip which includes a supporter and a sugar molecule immobilized on a surface thereof, the method using at least two sensor chips including sugar molecules which have different end structures, the at least two sensor chips including: a first sensor chip, which has a first sugar molecule, immobilized on a surface of a supporter; and a second sensor chip, which has a second sugar molecule whose end structure is different from that of the first sugar molecule, immobilized on a surface of a supporter, wherein the method includes the step of measuring a difference between a detection result yielded by using the first sensor chip and a detection result yielded by using the second sensor chip.

Further, the method for a measurement of surface plasmon resonance of the present invention is a method for a measurement of surface plasmon resonance, wherein a linker compound of a structure is used to immobilize the sugar molecules on the sensor chips.

With the above method, a surface plasmon resonance (SPR) is measured using at least two sensor chips having a ligand of the same structure except a sugar molecule, a difference between interactions of the at least two sensor chips can be observed as resulting from the sugar molecule. Therefore, the use of the above method for a measurement reduces a nonspecific interaction between part except the sugar molecule and another substance, thereby making it possible to observe a specific interaction between the sugar molecule and the substance.

For a fuller understanding of the nature and advantages of the invention, reference should be made to the ensuing detailed description taken in conjunction with the accompanying drawings.

BEST MODE FOR CARRYING OUT THE INVENTION

Figure 1:
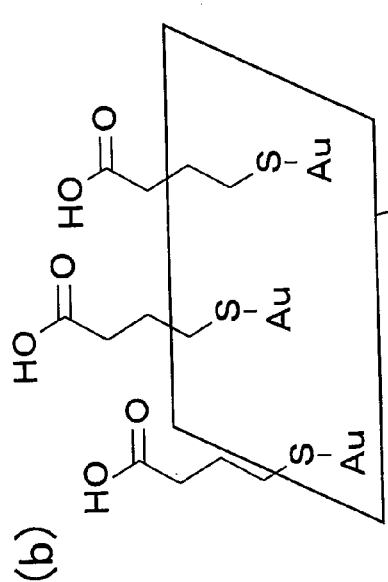
FIG. 1 is a perspective view showing a step of producing an avidin-immobilized sensor chip for surface plasmon resonance (SPR) for introducing a ligand of the present invention.
Figure 1:
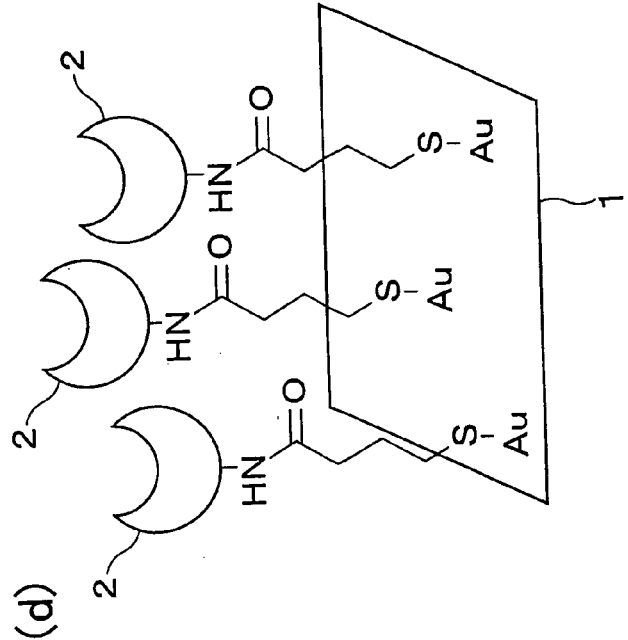
Figure 1:
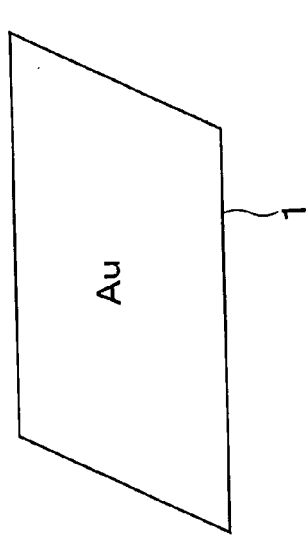
Figure 1:
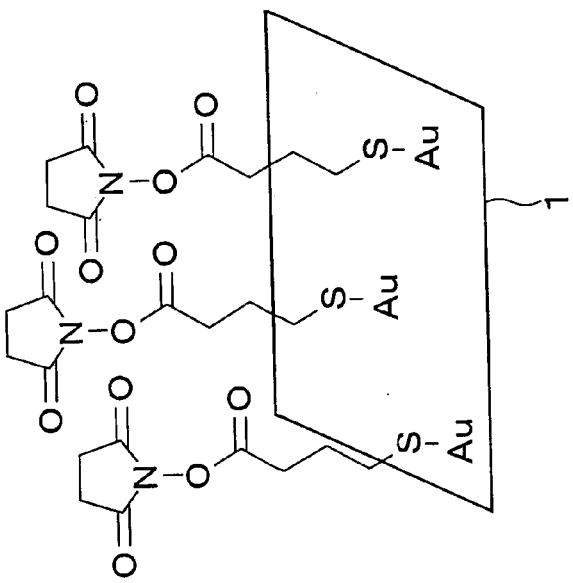

In the following, the present invention will be described in detail. However, the present invention is not to be limited by the following description.

A versatile linker compound of the present invention (hereinafter referred to as a linker compound) is used for suitably introducing a sugar molecule into a protein-analyzing supporter in order to detect and separate a protein which specifically interacts with a sugar molecule. For example, the linker compound is used for SPR and affinity chromatography, which utilizes a biological activity of a sugar (hereinafter referred to as a sugar molecule) such as an oligosaccharide, and a bioprobe in genetic engineering. Further, since the linker compound does not have a nonspecific interaction with a protein, the linker compound can be used suitably for detection and separation of a protein as noted above.

That is, a linker compound of the present invention, as specifically shown in general formula (1), has a biotin moiety or an iminobiotin moiety (hereinafter collectively referred to as a biotin moiety) serving as a moiety immobilizable onto the protein-analyzing supporter, and an aromatic amino group serving as a moiety capable of taking in a sugar molecule.

Biotin or iminobiotin (hereinafter collectively referred to as biotin) is known to specifically interact with streptoavidin or avidin (hereinafter collectively referred to as avidin), which is a basic glycoprotein. Therefore, when the linker compound having a biotin moiety is brought into contact with a surface of a supporter having avidin immobilized thereon, a biotin-avidin bond is formed, thereby easily immobilizing the linker compound onto the surface of the supporter.

Further, the linker compound, having a structure represented by X in following general formula (1), has a multi-branched moiety including four hydrocarbon derivative chains each of which have an aromatic amino group at an end thereof and may have a carbon-nitrogen bond in a backbone thereof. The amino group (—NH$_2$ group) of the aromatic amino group included in the multi-branched moiety reacts with an aldehyde group (—CHO group) or a ketone group (—CR'O group, R' meaning a hydrocarbon group) produced by an equilibration within a sugar molecule, thereby forming a Schiff base. A continuous reduction of the Schiff base causes the sugar molecule to be introduced into the aromatic amino group. Since X has four aromatic amino group ends, the linker compound, as described later, can take in four or more units of sugar molecules.

As specifically shown in general formula (2), X has two double-branched structures each formed by two hydrocarbon derivative chains bonding to a nitrogen atom (N) at the opposite end of the aromatic amino groups. The nitrogen atoms of the two double-branched structure bond to a single nitrogen atom (N) through the —CO— $(CH_2)_m$— group (where m is an integer of 1 to 6) to form a multi-branched structure. It is to be noted, in general formula (2), that $m^1$ and $m^2$ are not limited provided that they are an integer of 1 to 6. The integers represented by $m^1$ and $m^2$ may be mutually different or the same. Above all, in view of ease of production, it is preferable that $m^1$ to $m^2$ be mutually the same integer, 2 in particular. Further, $n^1$ and $n^2$ are not limited provided that they are an integer of 1 to 6. The integers represented by $n^1$ and $n^2$ may be mutually different or the same. Above all, in view of ease of production, it is preferable that $n^1$ and $n^2$ be mutually the same integer, 2 in particular. Further, $p^1$ to $p^4$ are not limited provided that they are an integer of 1 to 6. The integers represented by $p^1$ to $p^4$ may be mutually different, or may be the same either partly or completely. Above all, in view of ease of production of a compound having the multi-branched moiety, it is preferable that $p^1$ to $p^4$ be mutually the same integer, 2 in particular.

Thus, X has a structure serving as a multi-branched moiety which causes an atom such as carbon and nitrogen to bind the plurality of hydrocarbon derivative chains so as to form a branched structure. It is to be noted that although it is preferable that the plurality of hydrocarbon derivative chains included in X be all the same, they may have different structures so long as they have an aromatic amino group at an end thereof.

As described above, a linker compound having a structure represented by general formula (1) has a biotin moiety and an aromatic amino group end. Therefore, the linker compound makes it possible to easily and firmly bond a sugar molecule to the surface of the protein-analyzing supporter.

Further, the linker compound has a multi-branched moiety and aromatic amino groups at an end thereof. Therefore, with a ligand (to be mentioned later) which includes the linker compound and a sugar molecule introduced thereinto, four or more units of sugar molecules can be effectively collected on the surface of the supporter. Also, since four or more units of sugar molecules can be introduced into a single linker compound, a plurality of sugar molecules can be arranged with high reproducibility when the ligand is bound with a surface of a supporter.

Moreover, since the linker compound is hardly affected by a nonspecific interaction with a protein, the use of a linker compound of the present invention makes it possible to evaluate biological activities of sugar molecules with high reproducibility.

The linker compound is produced by a producing method described below. That is, the linker compound is produced by causing a condensation reaction of a biotin-containing compound with an amine compound including four branched chains each having an aromatic amino group end protected by a protecting group, and then by deprotecting the protecting group of the aromatic amino group end.

The biotin-containing compound is for example a compound which has a structure represented by following general formula (5). The biotin-containing compound is an ester compound which has a pentafluorophenyl group (Pfp) or a succinimide group (Su). Therefore, the biotin-containing compound, activated by these substituents, can react with a secondary amino group (—NH group) of an amino compound.

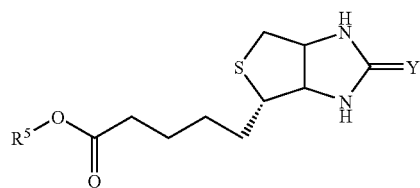

(5)

where Y has a structure represented by O or NH, and $R^5$ has a structure represented by

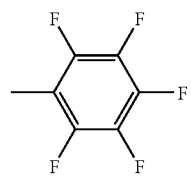

group (Pfp) or

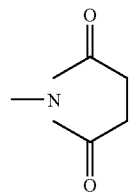

group (Su).

Further, the amino compound is not particularly limited if it includes a secondary amino group, and a branched chain which has an aromatic amino group end protected by a protecting group. The amino compound only needs to have a structure equivalent to the multi-branched moiety (X in general formula (1)) of the linker compound.

Therefore, the branched chain only needs to have a structure included in the hydrocarbon derivative chain except that the branched chain has the aromatic amino group end protected by a protecting group, instead of the aromatic amino group included in the hydrocarbon derivative chain. That is, the branched chain may be modified so that part of the carbon or hydrogen atoms in the hydrocarbon chain consisting of carbon and hydrogen atoms is replaced with other atoms or substituents. More specifically, the branched chain, having an aromatic amino group end protected by a protecting group, may be modified so that part of the carbon-carbon bonds constituting the backbone structure of the hydrocarbon chain is replaced with a carbon-nitrogen bond (C—N bond), a carbon-oxygen bond (C—O bond), or an amide bond (CO—NH bond).

Further, the protecting group is a substituent which is introduced to prevent an amino group of the aromatic amino group from undergoing the condensation reaction. Such a protecting group is not particularly limited provided that it is not affected when deprotecting a protecting group for a secondary amino group. The protecting group is for example a t-butoxycarbonyl group (—COOC(CH$_3$)$_3$ group; referred to as a Boc group), a benzyl group, or an arylcarbamate group (—COOCH$_2$CH═CH$_2$, Alloc group).

The amine compound is for example a compound which has a structure represented by following general formula (6). It is to be noted that a synthesis method of the amine compound will be described in detail in Examples to be mentioned later.

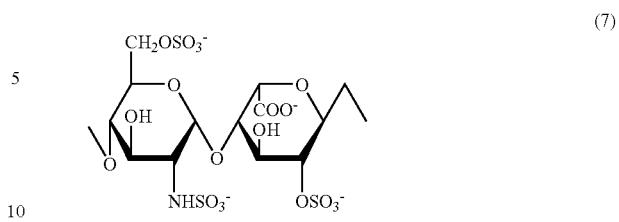
(7)

Another example is an oligosaccharide having a structure represented by following general formula (8), which is the sulfated oligosaccharide having incorporated a glucose at the reducing end.

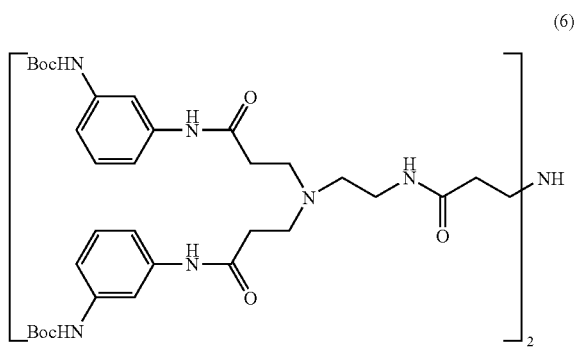
(6)

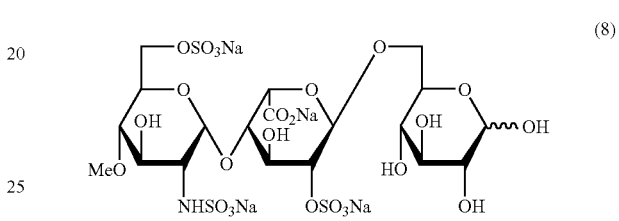
(8)

In the condensation reaction of the biotin-containing compound with the amine compound, a substituent such as Pfp or Su of the biotin-containing compound condenses with the secondary amino group to form an amide bond. Thereafter, a protecting group of the aromatic amino group end is deprotected and removed to free the aromatic amino group, thereby obtaining the linker compound.

Described in the following is a ligand which includes an aromatic amino group of the linker compound and a sugar molecule introduced thereinto. In a ligand of the present invention, a sugar molecule is introduced into the aromatic amino group. This is due to a continuous reduction of the Schiff base formed by the reaction of the amino group of the linker compound with the aldehyde group or ketone group produced by an equilibration within the sugar molecule.

The sugar molecule included in the ligand of the present invention is not particularly limited provided that it is a reducing sugar. The sugar molecule is for example a monosaccharide, an oligosaccharide, or a polysaccharide. The monosaccharide is for example a glucose, galactose, or mannose. The oligosaccharide is for example a maltose, lactose or a sulfated oligosaccharide to be mentioned later, having two to ten sugar molecules bonding to one another. The polysaccharide is for example a heparin, chondroitin sulfate, or heparan sulfate, having 11 or more sugar molecules including monosaccharides and oligosaccharides.

Further, the oligosaccharide is for example a sulfated oligosaccharide which has a specific partial disacharic structure (GlcNS6S-IdoA2S), represented by following general formula (7), which is contained in sulfated polysaccharic heparin known for having an anticoagulant activity.

It is to be noted that the oligosaccharide and the polysaccharide may be a homooligosaccharide or homopolysaccharide consisting of a single monosaccharide, or a complex carbohydrate consisting of different monosaccharides or derivatives thereof, or a conjugated polysaccharide including various monosaccharides or derivatives thereof, and oligosaccharides. Further, the sugar may be natural sugar obtained through isolation and purification from nature, or artificially synthesized sugar.

Specifically, a ligand of the present invention has a structure represented by general formula (3). The ligand having a structure represented by general formula (3) is obtained by adding a glucose, maltose, or lactose, serving as a sugar molecule, into a linker compound represented by general formula (1), where X has a structure represented by general formula (2). Since X represented by general formula (2) has a structure which includes four hydrocarbon derivative chains, one or two units of sugar molecules can be introduced into the aromatic amino group of each hydrocarbon derivative chain. Therefore, a ligand which has a structure represented by general formula (3) includes the linker compound and four to eight units of sugar molecules bound therewith. It is to be noted, in general formula (3), that $m^1$ and $m^2$, like $m^1$ and $m^2$ in general formula (2), are not limited provided that they are an integer of 1 to 6. The integers represented by $m^1$ and $m^2$ may be mutually different or the same. Further, $n^1$ and $n^2$, like $n^1$ and $n^2$ in general formula (2), are not limited provided that they are an integer of 1 to 6. The integers represented by $n^1$ and $n^2$ may be mutually different or the same. Further, $p^1$ to $p^4$, like $p^1$ to $p^4$ in general formula (2), are not limited provided that they are an integer of 1 to 6. The integers represented by $p^1$ to $p^4$ may be mutually different, or may be the same either partly or completely.

The sugar molecule to be introduced into the aromatic amino group of the hydrocarbon derivative chain of the linker compound is for example at least one sugar molecule selected from the group consisting of glucose, maltose, and lactose. Therefore, the ligand which has the structure represented by general formula (3) includes the linker compound and four to eight units of sugar molecules selected from the group consisting of glucose, maltose, and lactose depending on a structure of $R^7$ to $R^{10}$ in general formula (3).

It is to be noted that the sugar molecules to be introduced into the respective aromatic amino groups of the hydrocarbon derivative chains of the linker compound may be mutually different or may be the same either partly or completely. However, in view of ease of introduction of the sugar molecules, it is preferable that the sugar molecules be all the same. Therefore, when $m^1$, $m^2$, $n^1$, $n^2$, $p^1$, $p^2$, $p^3$, and $p^4$ are all 2 and four units of sugar molecules are introduced into the linker compound, a ligand represented by following general formula (16) is preferable for glucose. Similarly, a ligand represented by general formula (17) is preferable when the sugar molecules are maltose, and a ligand represented by general formula (18) is preferable when the sugar molecules are lactose.

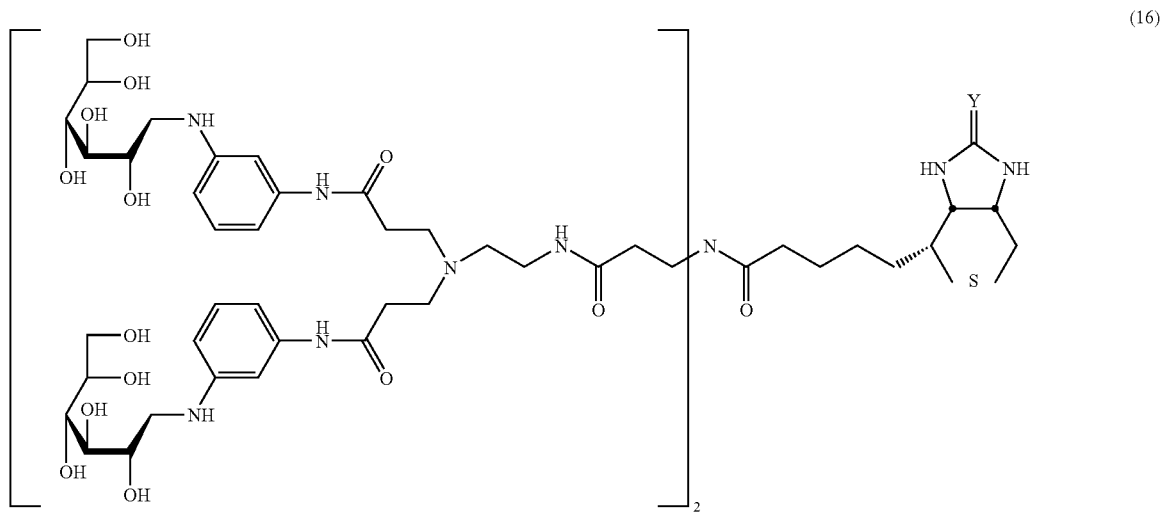

(16)

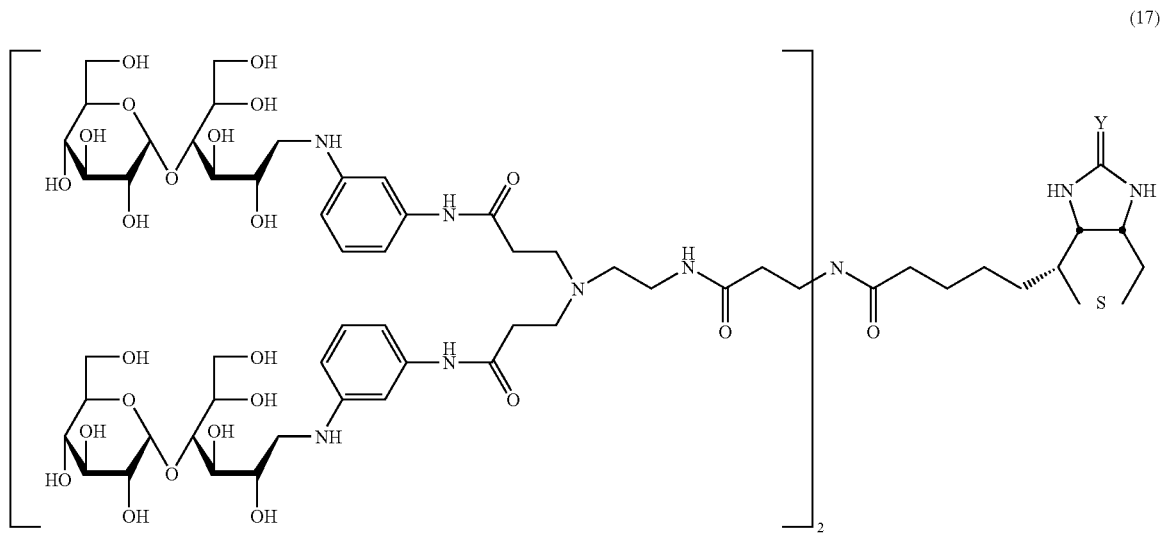

(17)

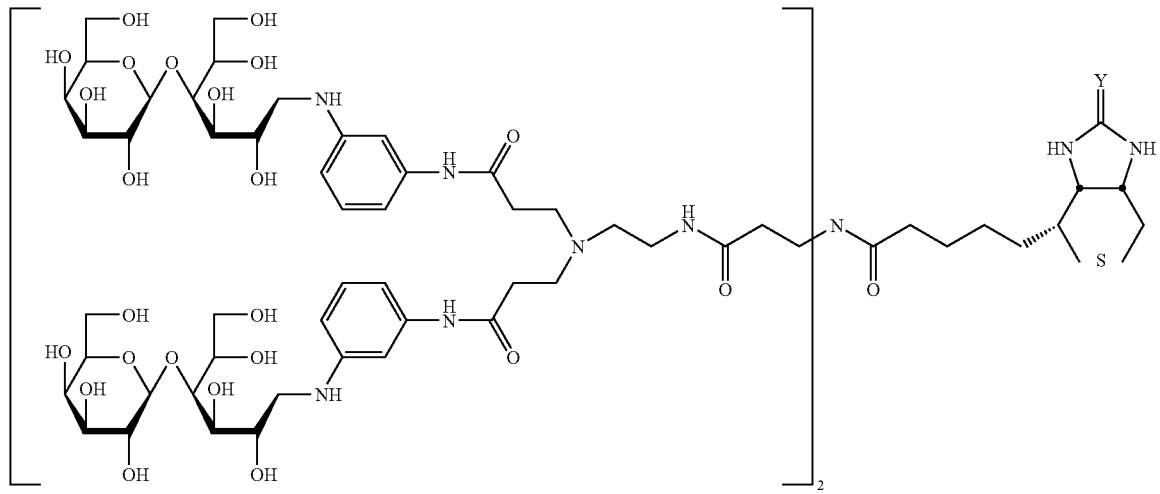

(18)

In general formulae (16) to (18), Y has a structure represented by O or NH.

Further, another ligand of the present invention has a structure represented by general formula (4). The ligand of the structure represented by general formula (4) is obtained by introducing a sugar molecule of a structure represented by general formula (8) to a linker compound represented by general formula (1), where X has a structure represented by general formula (2). Since X represented by general formula (2) has a structure which includes four hydrocarbon derivative chains, the ligand which has the structure represented by general formula (4) includes the linker compound and four units of sugar molecules bound therewith. It is to be noted, in general formula (4), that $m^1$ and $m^2$, like $m^1$ and $m^2$ in general formula (2), are not limited provided that they are an integer of 1 to 6. The integers represented by $m^1$ and $m^2$ may be mutually different or the same. Further, $n^1$ and $n^2$, like $n^1$ and $n^2$ in general formula (2), are not limited provided that they are an integer of 1 to 6. The integers represented by $n^1$ and $n^2$ may be mutually different or the same. Further, $p^1$ to $p^4$, like $p^1$ to $p^4$ in general formula (2), are not limited provided that they are an integer of 1 to 6. The integers represented by $p^1$ to $p^4$ may be mutually different, or may be the same either partly or completely.

Since the ligands include the linker compound and the sugar molecule introduced thereinto, the biotin moiety in the linker compound can bind to a protein-analyzing supporter including avidin by forming a biotin-avidin bond. This provides a ligand carrier including four units of sugar molecules collected and immobilized on the surface of the supporter through the biotin-avidin bond. With the ligand, a plurality of sugar molecules can be arranged for example on a surface of a protein-analyzing supporter with high reproducibility to obtain a ligand carrier. The use of the ligand carrier makes it possible to evaluate biological activities of the sugar molecules with high reproducibility. Therefore, the ligands of the present invention can be suitably used for easily introducing various sugar molecules in SPR, affinity chromatography, a bioprobe, and the like.

Thus, the present invention also includes a ligand carrier including the ligand of the present invention immobilized on a surface of a supporter through a biotin-avidin bond. The applicable field of the ligand carrier is not limited to the protein analysis. For example, the ligand carrier can be used for analyzing substances other than a protein so as to examine an interaction with sugar molecules.

The ligand can be introduced onto the surface of the protein-analyzing supporter by immersing, for a predetermined time period, an avidin-immobilized protein-analyzing supporter in a ligand solution containing the ligand, or by injecting the ligand solution into the supporter. The resultant ligand carrier has four or more units of sugar molecules collected and immobilized on the surface of the supporter.

For example, a sensor chip having avidin immobilized thereon is produced before obtaining a ligand carrier including the ligand-introduced thereinto. That is, as shown in FIG. 1(a), a glass substrate 1 whose surface is coated with gold (Au) is used. Then, as shown in FIG. 1(b), a gold-sulfur bond (Au—S bond) is utilized to immobilize, onto the glass substrate 1, 4-thiobutyric acid which has a structure represented by following general formula (9). It is to be noted that a substrate coated with a polymer having a carboxyl group may be used instead of the substrate 1 having 4-thiobutyric acid immobilized thereon.

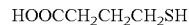  (9)

Figure 4:
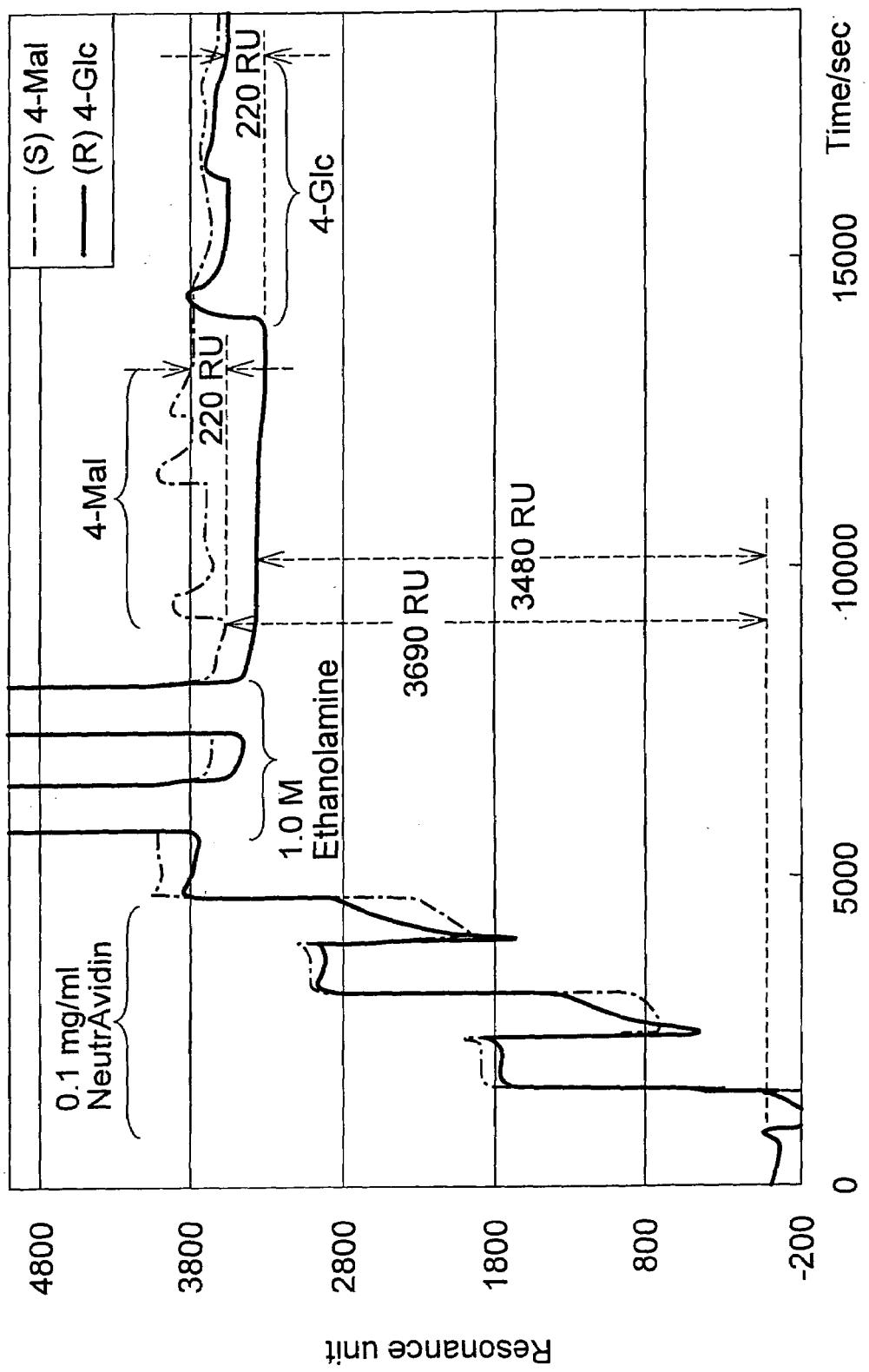
FIG. 4 is a graph showing a result of an SPR measurement in a step of obtaining a ligand carrier of the present invention.

Subsequently, as shown in FIG. 1(c), 4-thiobutyric acid immobilized on the glass substrate 1 is brought into reaction with N-hydroxysuccinimide in the presence of a carbodiimide reagent. Thereafter, an N-hydroxysuccinimide moiety and an end amino group of avidin 2 are condensed so as to immobilize the avidin 2 onto the glass substrate 1 as shown in FIG. 1(d). This makes it possible to obtain a sensor chip which includes the avidin immobilized onto the glass substrate 1.

Then, the sensor chip is brought into contact with a ligand solution including a ligand of the present invention. Specifically, the sensor chip is immersed in the ligand solution, or the ligand solution is flown onto a surface of the sensor chip. This makes it possible to obtain a ligand carrier 4 which includes a ligand 3 immobilized onto the sensor chip, as shown in FIG. 2(a), through a biotin-avidin bond known as a specific interaction.

It is to be noted that although a solvent used for the ligand solution is not particularly limited, a buffer solution such as a PBS (phosphate buffer solution) can be for example used. In case of immersion in the ligand solution, the duration of immersion only needs to be about 0.5 to 1.5 hours. In case of injection of the ligand solution, the amount of injection only needs to be 0.006 to 0.06 mg.

Figure 2:
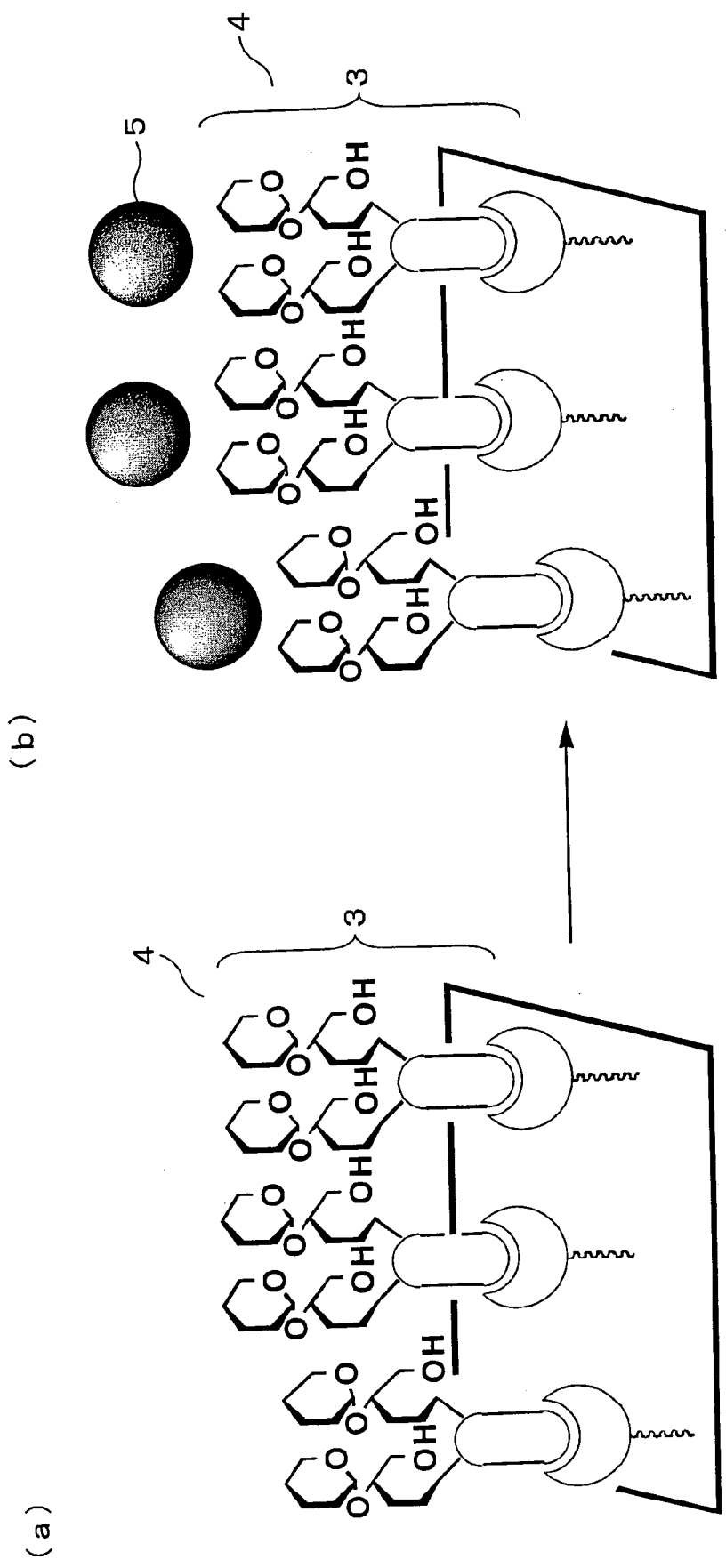
FIG. 2 is a perspective view of a ligand-introduced chip according to the present invention, wherein (a) represents a case in which there is no interaction with a protein, (b) represents a case in which there is an interaction with a protein.

As described above, if the ligand carrier 4 including the ligand 3 immobilized thereon is used to bring the ligand carrier into contact with a protein 5 (FIG. 2(b)) so as to measure a resonant angle with a surface plasmon resonance apparatus in the usual manner, the binding behavior of the ligand carrier with the protein 5 can be observed. It is to be noted that glass, plastic, or the like can be used to form a sensor chip used for an SPR measurement. Particularly, glass is suitably used. Further, a ligand carrier can be brought into contact with a protein by flowing a solution including a running buffer and a protein dissolved therein onto a surface of the ligand carrier, or by immersing the ligand carrier in the solution including the running buffer solution and the protein dissolved therein. The running buffer is for example a buffer solution such as a PBS.

Further, a column including avidin immobilized thereto is produced before obtaining a ligand carrier including the ligand introduced therein as an affinity column used for affinity chromatography. The column can be produced in the usual manner (e.g., cf. *Ligand Coupling Handbook*, Amersham Pharmacia Biotech Co., Ltd. ed. (2002)). For example, by flowing a solution containing avidin into a column filled with a carrier suitable to immobilizing a compound having an amino group (e.g., a column filled with a gel carrier including N-hydroxysuccinimide immobilized thereon), avidin can be immobilized onto the carrier. A ligand solution containing the ligand of the present invention is injected into the carrier including avidin immobilized thereon (hereinafter referred to as an avidin adduct). This makes it possible to obtain a ligand carrier which includes the avidin adduct and a ligand immobilized thereon through a biotin-avidin bond known as a specific interaction.

It is to be noted that a solvent used for the solution containing avidin is for example an aqueous solution of sodium acetate containing sodium chloride. Also, a solvent used for the ligand solution is for example a buffer solution such as a PBS.

Since the ligand of the present invention thus has a biotin moiety, the ligand carrier of the present invention can be obtained by taking in a sugar molecule with one step onto a surface of a protein-analyzing supporter for immobilization.

An affinity column having a ligand carrier which includes a ligand immobilized thereon as described above can be used to carry out affinity chromatography in a manner described below. That is, a protein solution is flown into an affinity column filled with a carrier (avidin adduct) including avidin immobilized thereon so as to perform affinity chromatography in the usual manner, thereby making it possible to separate a protein which binds to a ligand carrier from a protein which does not bind. It is to be noted that a solvent used for the protein solution is for example a buffer solution such as a PBS. Also, an eluting solution used for eluting a protein, which does not bind to a ligand carrier, from an affinity column is for example a buffer solution such as a PBS.

It is to be noted that the present invention also includes a method for introduction of a sugar molecule into a sensor chip of the SPR method and into a supporter such as an avidin adduct filled with an affinity column used for affinity column chromatography as described above.

As described above, since the ligand carrier of the present invention has the ligand, a plurality of sugar molecules can be arranged two-dimensionally on a surface of a supporter with high reproducibility. This makes it possible to observe a biological activity of a sugar molecule with high reproducibility, thereby making it possible to reveal a structure of a sugar molecule and quantitatively evaluate a biological activity of a sugar molecule.

Further, the present invention also includes an SPR measurement method for detecting a specific interaction of a sugar molecule by using a sensor chip including a sugar molecule immobilized on a surface of a supporter. With this method, an interaction between a sugar molecule and a substance such as a protein is observed by using at least two sensor chips including sugar molecules which have different end structures. It is to be noted that the end of a sugar molecule means the side not immobilized onto a sensor chip. Also, a substance whose interaction with a sugar molecule is observed is not limited to a protein.

An SPR measurement can be conducted as follows by using two sensor chips with different sugar molecules according to the above method. A first sugar molecule, immobilized on a surface of a supporter; and a second sensor chip, which has a second sugar molecule whose end structure is different from that of the first sugar molecule, immobilized on a surface of a supporter, are produced. The sensor chips can be obtained in the same manner as a ligand carrier (sensor chip) including a ligand immobilized on a sensor chip is produced. The sensor chips only need to be formed of ligands having different sugar molecules immobilized thereon. Sugar molecules to be compared with each other are for example lactose and glucose, maltose and glucose, and kojibiose and glucose. A ligand, in which the sugar molecules immobilized on the sensor chips are different, is for example a ligand shown in general formula (16) to (18). It is to be noted that not only a ligand of the present invention but also another ligand may be used.

For example, a protein which specifically interacts with the first sugar molecule is used to act on the two sensor chips under constant measurement conditions so as to observe resonant angles of the two sensor chips. By detecting a difference in resonance angle between the two sensor chips, a specific interaction between a sugar molecule and a protein or the like can be measured.

In the above arrangement, two kinds of sensor chips are simultaneously measured. However, this is not for limitation. More than two sensor chips may be measured and do not need to be measured simultaneously. Also, at least one sensor chip not including a sugar molecule introduced thereon may be used. For example, a sensor chip including only a linker compound immobilized thereon may be used.

Thus, the SPR measurement method of the present invention, suppressing a nonspecific interaction, makes it possible to measure a specific interaction of a sugar molecule with another object.

In the following, the present invention will be described further in detail according to Examples and Comparative Examples. It is to be noted, however, that they are not for limitation of the present invention.

It is to be noted, in the following examples, that the following instruments were used for a measurement of various types of spectrum, a measurement of optical rotation, and an electrophoresis.

Nuclear Magnetic Resonance (NMR) Spectrum: JEOL EX 270, JNM-LA 500 NMR spectrometer (product name).

Mass spectrometry: Mariner™ Biospectrometry™ Workstation (product name, ESI-TOF MS, PE Biosystems, Calif., USA) VOYAGER-DERP (product name, MALDI-TOF MS, PE Biosystems, Calif., USA).

Optical rotation: Perkin Elmer model 241 polarimeter (product name).
Ultraviolet visible spectrum photometer: JASCO V-530 UV/Vis spectrophotometer (product name).
Surface plasmon resonance biosensor: SPR670 (product name, Nippon Laser & Electronics LAB).
Electrophoresis apparatus: ATTO CompactPAGE AE-7300 (product name).
Ready-made gel for an electrophoresis: ATTO PAGEL-Compact AE-6000 (12.5%) Lot: 244S024 (product name).
Also, the following silica gels were used for chromatography.
Thin layer chromatography: Merck Silica gel 60 F254 (No. 5715) (product name).
Preparative thin layer chromatography: Merck Silica gel 60 F254 (No. 5744) (product name).
Medium-pressure column chromatography: Merck Silica gel 60 (No. 9385, 0.040–0.063 mm, 230–400 mesh) (product name).

EXAMPLE 1

Synthesis of a Linker Compound

A linker compound of the present invention was synthesized according to the following procedure. As shown in following general formula (10), benzylamine (Compound 1, Bn represents a benzyl group in the formula) was brought into reaction with methyl acrylate (6 equiv.) in methanol (in the formula, MeOH) at room temperature. Two units of methyl acrylate were added by Michael addition to the benzylamine to obtain Compound 2 at the yield of 93%. Thereafter, a large excess (50 equiv.) of ethylenediamine was added into methanol containing Compound 2 at room temperature. The ethylenediamine was condensed with Compound 2 to obtain Compound 3. It is to be noted that a large excess (50 equiv.) of ethylenediamine is added in order to prevent Compound 2 from condensing simultaneously with two amino groups of ethylenediamine.

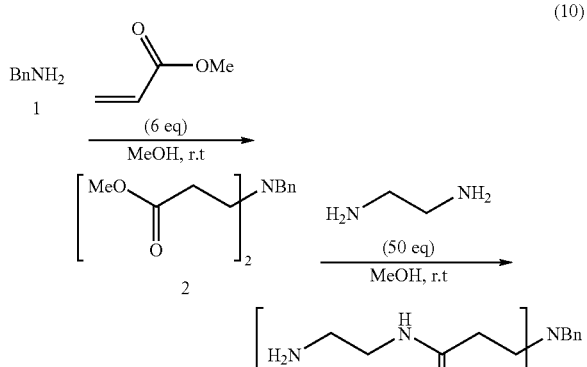

(10)

Compound 2 was obtained by the following procedure. A methanol solution (143 mL) of benzylamine (4.7 mL, 44.6 mmol) was mixed with methyl acrylate (8.52 mL, 104 mmol), stirred for 8 hours under nitrogen atmosphere at room temperature, further mixed with methyl acrylate (3.87 mL, 47 mmol), and stirred at room temperature for 12 hours. Thereafter, the stirred solution was further mixed with methyl acrylate (7047 mL, 94 mmol) and stirred overnight to obtain a reaction solution of methanol and methyl acrylate. The methanol/methyl acrylate reaction solution was concentrated under reduced pressure to obtain a residue. The residue was purified by medium-pressure silica gel chromatography (300 g, toluene:ethyl acetate=5:1 to 3:1) to obtain a colorless oily solution serving as Compound 2.

Compound 2 was obtained at the yield of 11.7 g (95%). Also, $^1$H NMR (400 MHz, CD$_3$OD) measurement was conducted on Compound 2 so obtained to find that δ7.28–7.20 (5H, m, aromatic), δ4.79 (6H, s, OMe*×2), δ3.57 (2H, d, J=4.6 Hz, NCH$_2$*Ph), δ2.76 (4H, td, J$_{gem}$=4.6, J$_{vic}$=6.8 Hz, CH$_2$*NBn), δ2.46 (4H, td, J$_{gem}$=4.6, J$_{vic}$=6.8 Hz, COCH$_2$*CH$_2$NBn). It is to be noted that each chemical shift δ indicates a measured value corresponding to a proton having a plurality of Hs marked with *, i.e., H*. The same applies to the following description. An ESI-MS (positive) measurement (time-of-flight mass spectrometer measurement) was conducted to find that the m/z (mass/charge) was 302.1 [(M+Na)+].

Subsequently, as shown in following general formula (11), methanol containing Compound 3 was mixed with methyl acrylate (11 equiv.) at room temperature. Four units of methyl acrylate were added to Compound 3 to obtain Compound 4 at the yield of 81%. Thereafter, under alkaline conditions with an aqueous solution of 2 M sodium hydroxide added to methanol, methyl ester of Compound 4 was hydrolyzed to obtain Compound 5, which has four units of carboxyl groups (—COOH group) at an end thereof, at the yield of 96%.

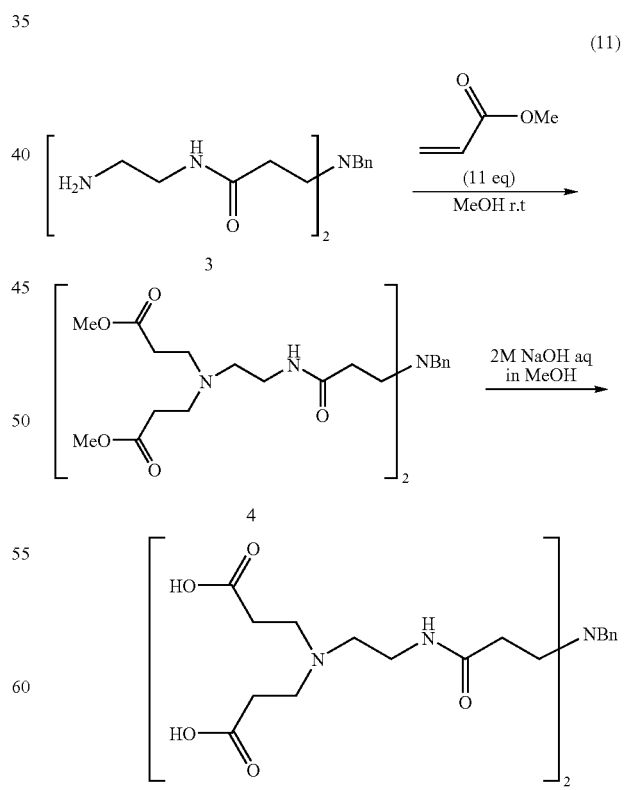

(11)

Compound 4 was obtained by the following procedure. Methanol (120 mL) containing Compound 2 (9.97 g, 35.7 mmol) dissolved therein was stirred for 5 minutes at 0° C. under nitrogen atmosphere, mixed with ethylenediamine anhydride (60 mL, 1.11 mol), stirred for 50 minutes at 0° C., stirred overnight at room temperature, further mixed with ethylenediamine anhydride (50 mL, 0.93 mol), and stirred overnight at room temperature to obtain a reaction solution of Compound 2 and ethylenediamine anhydride. The Compound 2/ethylenediamine anhydride reaction solution was concentrated to obtain a yellow oily residue. The yellow oily residue was dissolved in methanol (120 mL), mixed with methyl acrylate (19.3 mL, 234 mmol), stirred overnight at room temperature, further mixed with methyl acrylate (19.3 mL, 234 mmol), and stirred overnight at room temperature to obtain a reaction solution of yellow oily residue and methyl acrylate. The yellow oily residue/methyl acrylate reaction solution was concentrated under reduced pressure to obtain a residue. The residue was purified by medium-pressure silica gel chromatography (700 g, chloroform: methanol=20:1 to 7:1) to obtain a yellow oily solution serving as Compound 4.

Compound 4 was obtained at the yield of 24.5 g (81%). Also, $^1$H NMR (400 MHz, CD$_3$OD) measurement was conducted on Compound 4 so obtained to find that δ7.29–7.28 (5H, m, aromatic H), δ3.66 (12H, s, OMe*×4), δ3.27 (4H, q, J=6.1 Hz, CH$_2$*NHCO), δ2.81 (4H, t, J=6.8 Hz, CH$_2$*NBn), δ2.75 (8H, t, CH$_2$×4, J=6.8 Hz, CH$_2$*NCH$_2$), δ2.52 (4H, t, CH$_2$×2, J=5.9, 6.1 Hz, CH$_2$*CH$_2$NHCO), δ2.41 (12H, t, CH$_2$×(2+4), J=6.8, 6.6 Hz, NCOCH$_2$*CH$_2$NHCO, MeOCOCH$_2$*). Also, an ESI-MS (positive) measurement was conducted to find that the m/z was 680.4 [(M+H)$^+$].

Compound 5 was obtained by the following procedure. Compound 4 (1.0 mg, 1.47 mmol) was dissolved in methanol (7.4 mL). An aqueous solution of 4 M sodium hydroxide was added to the mixture and stirred for 2 hours at 0° C. under argon atmosphere to obtain a reaction solution of Compound 4 and sodium hydroxide. The Compound 4/sodium hydroxide reaction solution was mixed with 4 M hydrochloric acid (7 mL), confirmed to be at pH 3 with pH test paper, concentrated under reduced pressure to obtain a residual aqueous solution. The residual aqueous solution was freeze-dried to obtain a freeze-dried residue. The obtained freeze-dried residue was purified with HP-20 (300 mL, H$_2$O to H$_2$O:methanol=1:1 to methanol). A fraction eluted with H$_2$O/methanol was collected and concentrated under reduced pressure. Thereafter, the residue which had been concentrated under reduce pressure was freeze-dried to obtain a light yellow crystal serving as Compound 5.

Compound 5 was obtained at the yield of 878 mg (96%). Also, $^1$H NMR (400 MHz, CD$_3$OD) measurement was conducted on Compound 5 so obtained to find that δ7.54–7.38 (5H, m, aromatic H), δ3.60 (2H, s, NCH$_2$*Ph), δ3.58 (2H, t, J=6.1 Hz, CH$_2$*NHCO), δ3.34–3.24 (16H, m, CH$_2$×8, CH$_2$*NBn, MeOCOCH$_2$CH$_2$*N, NCH$_2$CH$_2$*NHCO), δ2.79 (4H, t, CH$_2$×2, J=7.0 Hz, COCH$_2$*CH$_2$NBn), δ2.60 (8H, t, CH$_2$×4, J=6.4 Hz, MeOCOCH$_2$*). An ESI-MS (positive) measurement was conducted to find that the m/z was 624.3 [(M+H)$^+$].

It is to be noted, in the present example, that Compound 5 includes four units of carboxyl groups synthesized thereinto. However, if necessary, it is possible to easily synthesize a scaffold structure which has 8, 16, and 32 units of carboxyl groups at an end thereof. This is done by continuing a reaction which condenses ethylenediamine again and adds methyl acrylate without hydrolyzing methyl ester of Compound 4.

Subsequently, as shown in the following formula (12), in N, N-dimethyl formamide (DMF), containing 1-hydroxybenzotriazole (in the formula, HOBt; 5 equiv.) and diisopropyl ethylamine (in the formula, DIPEA); 10 equiv.), under temperature change from 0° C. to 40° C. o-[7-azabenzotriazole-1-yl]-N,N,N',N'-tetramethyluranium hexafluorophosphate (in the formula, HATU) was used as an activator to condense a phenylenediamine derivative (Compound 6, 5 equiv.) including one amino group protected by a t-butoxycarbonyl group (Boc in the formula, hereinafter referred to as a Boc group) with a carboxyl group at an end of Compound 5, thereby obtaining Compound 7 at the yield of 57%. Subsequently, palladium (10% Pd—C) was used to perform a catalytic reduction of Compound 7 in methanol at 50° C. under hydrogen atmosphere so as to deprotect a benzyl group serving as a protecting group of a secondary amino group of Compound 7, thereby obtaining Compound 8 at the yield of 80%.

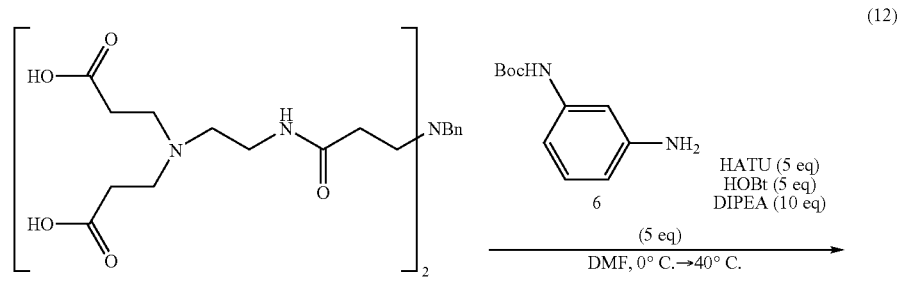

(12)

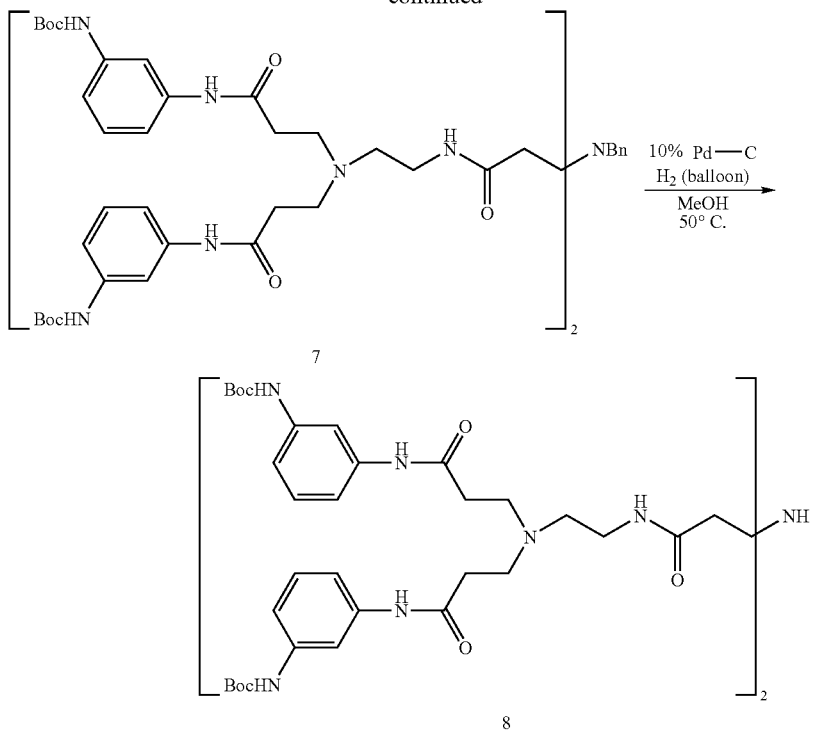

Compound 6 was obtained by the following procedure. In Methanol (240 mL), m-phenylenediamine (7.81 g, 72.2 mmol) was dissolved. To the mixture, di-t-butoxycarbonate (16.5 mL, 71.8 mmol) and triethylamine (10 mL, 71.5 mmol) were added. The mixture was stirred for 30 minutes at 0° C. in a shade under argon atmosphere and then stirred overnight at room temperature to obtain an m-phenylenediamine reaction solution. The m-phenylenediamine reaction solution was concentrated under reduced pressure to obtain a residue. The residue was purified by medium-pressure silica gel chromatography (500 g, chloroform:methanol=10:1 to 7:1) to obtain a yellowish white crystal serving as Compound 6.

Compound 6 was obtained at the yield of 13.3 g (88%). Also, a $^1$H NMR (400 MHz, CDCl$_3$) was conducted on Compound 6 so obtained to find that δ7.03 (1H, dd, J=7.8, 8.1 Hz, aromatic H), δ6.54 (1H, d, J=8.1 Hz, aromatic H), δ6.36 (1H, t, J=7.8 Hz, aromatic H), δ3.67 (2H, s, NH$_2$), δ1.51 (9H, m, CH$_3$×3 of BOC). An ESI-MS (positive) was conducted to find that the m/z was 209.1 [(M+H)$^+$].

Compound 7 was obtained by the following procedure. Compound 5 (54.8 mg, 87.9 μmol) and 1-hydroxybenzotriazole (66.4 mg, 492 μmol) were dissolved in anhydrous dimethyl formamide (0.9 mL) under nitrogen atmosphere and stirred for 15 minutes at 0° C. to obtain a reaction solution of Compound 5 and 1-hydroxybenzotriazole. The Compound 5/1-hydroxybenzotriazole reaction solution was mixed with HATU (168 mg, 441 μmol) and diisopropyl ethylamine (150 mL, 882 μmol) and Compound 6 (98.2 mg, 471 μmol), stirred overnight at room temperature, and stirred for 5 hours at 50° C. to obtain a reaction solution of Compound 5 and Compound 6. The Compound 5/Compound 6 reaction solution was concentrated under reduced pressure to obtain a residue. The residue was purified by medium-pressure silica gel chromatography (80 g, chloroform:methanol=15:1 to 5:1) to obtain a white crystal serving as Compound 7.

Compound 7 was obtained at the yield of 69.2 mg (57%). Also, $^1$H NMR (400 MHz, CDCl$_3$) was conducted on Compound 7 so obtained to find that δ7.39 (4H, s, 1H×4, aromatic H), δ7.39–6.53 (21H, m, aromatic H), δ3.63 (2H, s, NCH$_2$*Ph), δ3.15 (4H, d, CH$_2$×2, J=6.2 Hz, CH$_2$*NHCO), δ2.76 (8H, t, CH$_2$×4, J=6.2 Hz, MeOCOCH$_2$CH$_2$*N), δ2.49 (8H, t, CH$_2$×4, J=6.2 Hz, MeOCOCH$_2$*CH$_2$N), δ2.45 (4H, t, CH$_2$×2, J=6.4 Hz, CH$_2$*NBn), δ2.38 (4H, t, CH$_2$×2, J=6.6 Hz, NCH$_2$CH$_2$*NHCO), δ2.03 (4H, t, CH$_2$×2, J=6.4 Hz, NHCOCH$_2$*CH$_2$NBn), δ1.48 (36H, s, CH$_3$×12, Me of BOC). An ESI-MS (positive) was conducted to find that the m/z was 693.3[(M+2H)$^{2+}$].

Compound 8 was obtained by the following procedure. Compound 7 (49.8 mg, 36.0 μmol) was mixed with a methanol slurry of 10% Pd—C (70.2 mg) and stirred overnight at room temperature under hydrogen atmosphere to obtain a Compound 7 reaction solution. The Compound 7 reaction solution was filtered with a membrane filter to obtain a filtrate. The filtrate was concentrated under reduced pressure to obtain a white crystal serving as Compound 8.

Compound 8 was obtained at the yield of 36.8 mg (80%). Also, $^1$H NMR (400 MHz, CD$_3$CD) was conducted on Compound 8 so obtained to find that δ7.64 (4H, s, 1H×4, aromatic H), δ7.05–6.91 (12H, m, aromatic H), δ3.40 (4H, t, CH$_2$×2, J=5.4 Hz, CH$_2$*NHCO), δ3.19 (8H, br, CH$_2$×4, MeOCOCH$_2$CH$_2$*N), δ2.98 (4H, br, CH$_2$×2, NCH$_2$CH$_2$*NHCO), δ2.89 (4H, t, CH$_2$×2, J=5.6 Hz, CH$_2$CH$_2$*NH), δ2.71–2.70 (4H, br, CH$_2$×2, J=5.6 Hz, MeOCOCH$_2$*CH$_2$N), δ2.36 (4H, t, CH$_2$×2, J=5.4 Hz, NHCOCH$_2$*CH$_2$NBn), δ1.39 (36H, s, CH$_3$×12, Me of BOC). An ESI-MS (positive) measurement was conducted to find that the m/z was 647.9[(M+2H)$^{2+}$].

Next, as shown in following general formula (13), biotin activated by a pentafluorophenyl group (Pfp) was condensed with an amino group, deprotected to be free, of Compound 8 in DMF in the presence of triethylamine (in the formula, TEA) at 50° C. to obtain Compound 9 at the yield of 63%. Thereafter, Compound 9 was deprotected of a Boc group in CH$_2$Cl$_2$ containing trifluoroacetic acid (in the formula, TFA) at 0° C. to obtain Compound 10 serving as a linker compound of the present invention.

mixed with Compound 8 (70.6 mg, 54.5 mmol) and triethylamine (60 μL, 0.811 mmol) and stirred overnight at 50° C. to obtain a Compound 8 reaction solution. The Compound 8 reaction solution was concentrated under reduced pressure to obtain a residue. The residue was dissolved in 100 ml of ethyl acetate and washed with a saturated aqueous solution of sodium chloride (50 mL×3) to obtain an organic phase. The organic phase was mixed with sodium sulfate and dried. The drying agent was filtered out from the dried residue to obtain a filtrate. The filtrate was concentrated under reduced pressure to obtain a residue. The residue was purified by

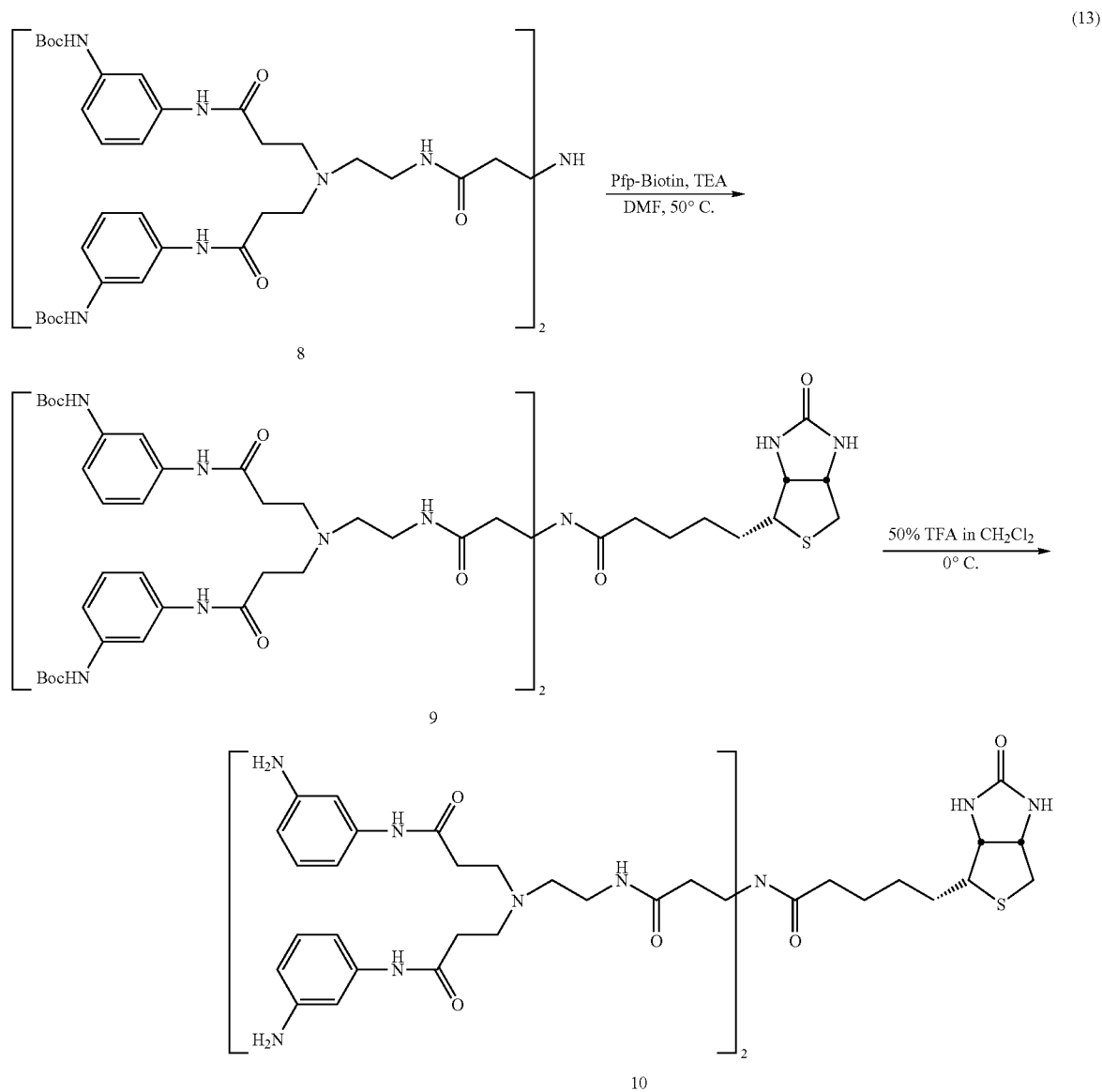

(13)

Compound 9 was obtained by the following procedure. Biotin (80.1 mg, 0.397 mmol) and dicyclohexylcarbodiimide (80.8 mg, 0.39 mmol) were dissolved in anhydrous dimethyl formamide (1 mL) under argon atmosphere, stirred for 4 hours at 50° C., mixed with pentafluorophenol (120 mg, 0.65 mmol), and stirred overnight at 50° C. to obtain a biotin reaction solution. The biotin reaction solution was medium-pressure silica gel chromatography (25 g, chloroform:methanol=10:1 to 5:1) to obtain a white crystal serving as Compound 9.

Compound 9 was obtained with a 52.3 mg (63%). Also, $^1$H NMR (400 MHz, CD$_3$OD) measurement was conducted on Compound 9 so obtained to find that δ7.61 (2H, s, aromatic H), δ7.57 (2H, s, aromatic H), δ7.06–6.95 (12H, m, aromatic), δ4.31 (1H, dd, $J_{B7/B6}$=4.3, $J_{B7/B3}$=6.6 Hz, Biotin NHCH*CH$_2$S), δ4.09 (1H, dd, $J_{B3/B4}$=4.5, $J_{B3/B7}$=6.6 Hz, Biotin NHCH*CHS), δ3.35 (4H, t, CH$_2$×2, J=6.8 Hz, CH$_2$CH$_2$*NCH$_2$CH$_2$CONHPh), δ3.19–3.17 (4H, m, CH$_2$× 2, NCH$_2$*CH$_2$CONHCH$_2$CH$_2$), δ2.98–2.93 (1H, m, $J_{B4/B3}$=4.5 Hz, Biotin NHCHCH*S), δ2.78–2.72 (9H, m, CH+CH$_2$×4, $J_{B6a/B6b}$=10 Hz, $J_{B6a/B7}$=4.3 Hz, Biotin NHCHCH$_2$*S, NCH$_2$*CH$_2$CONHPh), δ2.53–2.50 (4H, br, CH$_2$×2, CH$_2$*CH$_2$NCH$_2$CH$_2$CONHPh), δ2.44–2.40 (9H, m, CH+CH$_2$×4, $J_{B6b/B6a}$=10 Hz, Biotin NHCHCH$_2$*S, NCH$_2$CH$_2$CONHPh), δ2.20 (2H, t, $J_{B12/B11}$=7.6 Hz, Biotin CH$_2$CH$_2$CH$_2$CH$_2$*CO), δ2.16 (4H, t, CH$_2$×2, J=6.8 Hz, CH$_2$CH$_2$*N CH$_2$CH$_2$CONHPh), δ1.55–1.51 (4H, br, CH$_2$× 2, Biotin CH$_2$*CH$_2$CH$_2$*CH$_2$CO), δ1.40 (36H, s, CH$_3$×12, Me of BOC), δ1.28–1.24 (2H, m, CH$_2$×1, Biotin CH$_2$CH$_2$*CH$_2$CH$_2$CO). An ESI-MS (positive) measurement was conducted to find that the m/z was 761.4[(M+2H)$^{2+}$].

Compound 10 was obtained by the following procedure. Compound 9 (52.3 mg, 34.4 μmol) was dissolved in dichloromethane (1.5 mL), mixed with trifluoroacetic acid (1 mL), and stirred for 1 hour at 0° C. to obtain a reaction solution of Compound 9 and trifluoroacetic acid. The Compound 9/trifluoroacetic acid solution was concentrated under reduced pressure to obtain a residue. The residue was purified using LH20 (140 mL, elution by methanol) to obtain a yellow crystal serving as Compound 10.

Compound 10 was obtained at the yield of 50.9 mg (94%). Also, $^1$H NMR (400 MHz, CD$_3$OD) measurement was conducted on Compound 10 so obtained to find that δ7.51 (4H, s, aromatic H), 7.21 (8H, s; aromatic H), δ6.83–6.81 (4H, m, aromatic H), δ4.32 (1H, dd, $J_{B7/B6}$=4.3, $J_{B7/B3}$=8.0 Hz, Biotin NHCH*CH$_2$S), δ4.14 (1H, dd, $J_{B3/B4}$=4.4, $J_{B3/B7}$=8.0 Hz, Biotin NHCH*CHS), δ3.59–3.52 (12H, m, CH$_2$×6, NCH$_2$*CH$_2$CONHPh, CH$_2$*CH$_2$NCH$_2$CH$_2$CONHPh), δ3.47–3.37 (4H, m, CH$_2$× 2, CONCH$_2$*CH$_2$CONH), δ3.35–3.33 (4H, m, CH$_2$CH$_2$*NCH$_2$CH$_2$CONHPh), δ3.02 (1H, dt, $J_{B4/B9}$=4.9 Hz, Biotin NHCHCH*S), δ2.92–2.89 (8H, m, CH$_2$×4, NCH$_2$CH$_2$*CONHPh), δ2.79 (1H, dd, $J_{gem}$=12.8, $J_{vic}$=5.0 Hz, Biotin NHCHCH$_2$*S), δ2.58 (1H, d, $J_{gem}$=12.8 Hz, Biotin NHCHCH$_2$*S), δ2.37 (2H, t, J=7.0 Hz, CONCH$_2$CH$_2$*CONH), δ2.31 (2H, t, J=7.1 Hz, CONCH$_2$CH$_2$*CONH), δ2.21 (2H, t, CH$_2$×1, Biotin COCH$_2$*CH$_2$CH$_2$CH$_2$), δ1.48–1.19 (6H, br, CH$_2$×3, Biotin COCH$_2$CH$_2$*CH$_2$*CH$_2$*). An ESI-MS (positive) measurement was conducted to find that the m/z was 1142.6 [(M+Na)$^{2+}$]. It was also found that [a]$_D^{22}$=+0.947 (c 0.972, MeOH).

Compound 10 so obtained proved to be ESI-MS (positive) m/z=1120.62 [M+H]$^+$ and have a structure represented by general formula (13) as Compound 10. NMR data obtained from an NMR measurement also showed that Compound 10 has a structure represented as Compound 10.

EXAMPLE 2

Synthesis of a Ligand

The linker compound (Compound 10) obtained in Example 1 was used to synthesize a ligand having a structure represented by general formula (3) according to the following procedure.

As shown in following general formula (14), Compound 10 was mixed with maltose (9 equiv.) in water:acetic acid (AcOH):methanol=12:1:15 (5% acetic acid solution, pH 4) serving as a solvent and stirred for 5 days. Thereafter, after confirmation of the formation of four units of Schiff bases by a time-of-flight mass spectrometer, the resulting solution was mixed with NaBH$_3$CN (20 equiv.) serving as a reducing agent separately twice and stirred for 4 days at room temperature so as to cause a reductive amination reaction, thereby obtaining a compound. The compound so obtained was purified with HP-20 (DIAION®) to obtain Compound 11 at the yield of 89%. Compound 11 was obtained in the form of a mixture including 5 to 7 units of maltose collected.

(14)

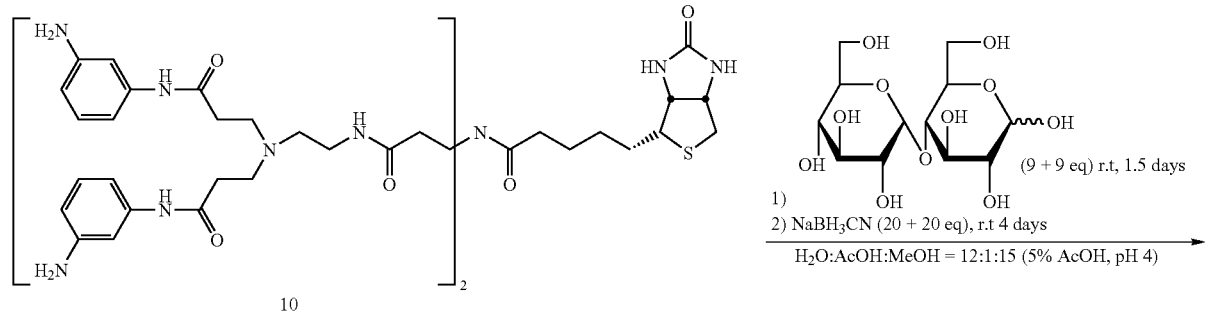

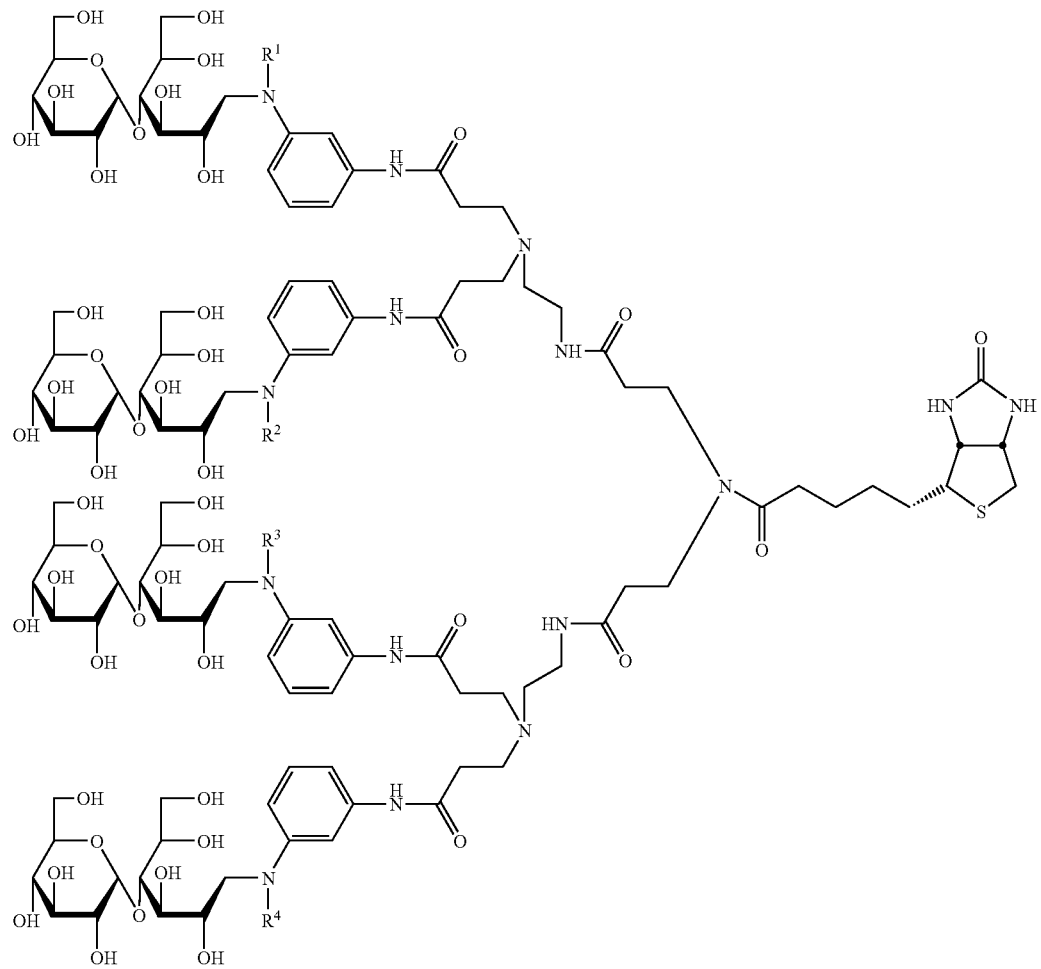

11 where $R^1$, $R^2$, $R^3$, and $R^4$ independently have a structure represented by

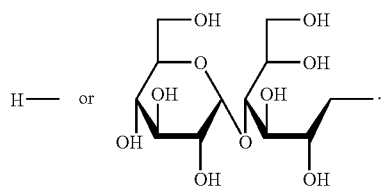

EXAMPLE 3

Synthesis of a Ligand

The linker compound (Compound 10) obtained in Example 2 was used to synthesize a ligand having a structure represented by general formula (5) according to the following procedure.

As shown in following general formula (15), Compound 12 was produced in the same procedure except that a sugar molecule represented by general formula (8) was used instead of maltose.

(15)

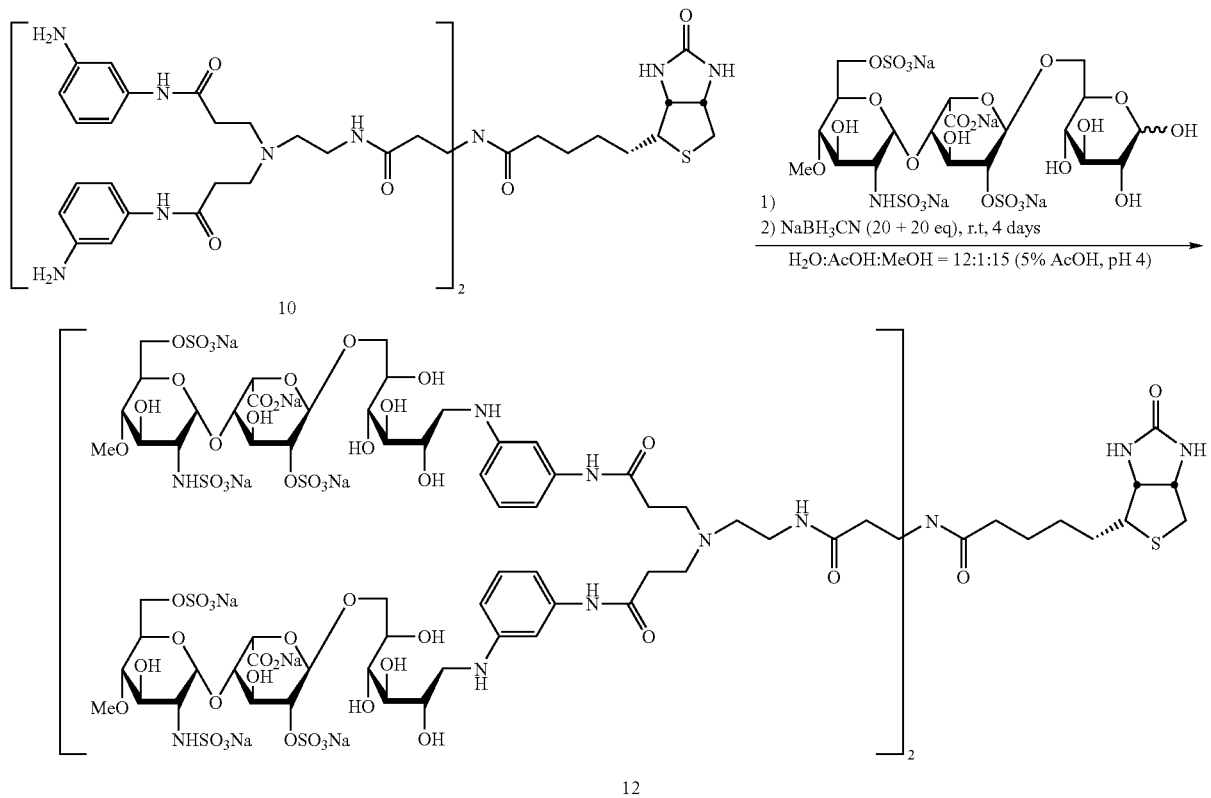

Compound 12 was obtained by the following procedure. Linker Compound 10 (2.4 mg, 2.1 μmol) and a sugar molecule (GlcNS6S-IdoA2S-Glc and substantially 11.0 mg, 12.8 μmol) represented by the general formula (8) were dissolved in a mixed solvent (water/acetic acid/methanol=12/1/15, 0.4 mL) and stirred for 2 days at room temperature to obtain a reaction solution of Linker Compound 10 and GlcNS6S-IdoA2S-Glc. The Linker Compound 10/GlcNS6S-IdoA2 S-Glc reaction solution was mixed with sodium cyanoborohydridesodium cyanoborohydride (approx. 3 mg, 40 μmol), stirred for 2 days at room temperature, mixed again with sodium cyanoborohydride (approx. 2 mg, 40 μmol), and stirred overnight at room temperature for reduction. The Linker Compound 10/GlcNS6S-IdoA2S-Glc reaction solution so reduced was concentrated under reduced pressure to obtain a residue. The residue was purified with SephadexG-50 fine [100 mL eluate: 0.85 M aqueous solution of sodium chloride+PBS (1/1 vol.) mixed solution], and a fraction found having UV absorption at 254 nm was collected and concentrated to obtain a residue. The residue was freeze-dried. The freeze-dried residue fraction so obtained was desalted with HP-20 (60 mL), and a fraction eluted by water/methanol=1/1 was collected, concentrated, and freeze-dried. The freeze-dried fraction so obtained was desalted again with SephadexG-10 (20 mL), and a fraction found having UV absorption at 254 nm was collected, concentrated, and freeze-dried to obtain a white crystal serving as Compound 12.

Compound 12 was obtained at the yield of 4.99 mg (42%). Also, $^1$H NMR (500 MHz, $D_2O$) was conducted on Compound 12 so obtained to find that δ7.14–7.12 (4H, br, aromatic H), δ6.91–6.59 (12H, br, aromatic H), δ5.36–5.34 (4H, br, H-1"), δ5.12 (4H, br, H-1'), δ4.51 (4H+1H, d, J=2.6 Hz, H-5', Biotin NHCH*CH$_2$S), δ4.29 (4H×2, d, $J_{gem}$=9.3 Hz, H-6"b, H-2), δ4.19 (4H×3, d, $J_{gem}$=9.3 Hz, H-6"a, H-3', Biotin NHCH*CHS), δ4.05 (4H, d, J=2.5 Hz, H-4'), δ4.00–3.93 (4H×3, m, H-5", H-1b, H-6b), δ3.86–3.85 (4H, m, H-5), δ3.78–3.72 (4H, m, H-4), δ3.70 (4H, t, H-3"), δ3.67–3.59 (4H ×2, m, H-3, H-6b), δ3.56–3.52 (4H, br, Link PhNHCOCH$_2$CH$_2$NCH$_2$CH$_2$*), δ3.42 (4H, t, J=6.6 Hz, Link COCH$_2$CH$_2$*NCO), δ3.36–3.30 (4H×2+8H, m, H-2, H-4", Link PhNHCOCH$_2$ $_{CH2}$*N), δ3.25 (4H, dd, J=10.3, 3.3 Hz, H-2"), δ3.18–3.05 (1H×2, br, H-1a, Biotin NHCHCH*S), δ2.93–2.90 (4H, br, Link PhNHCOCH$_2$CH$_2$NCH$_2$*CH$_2$), δ2.89 (1H, br, Biotin NHCHCH$_2$*S), δ2.82 (4H, t, J=6.6 Hz, Link COCH$_2$*CH$_2$NCO), δ2.72–2.70 (1H, br, Biotin NHCHCH$_2$*S), δ2.58 (8H, t, J=6.6 Hz, Link PhNHCOCH$_2$*CH$_2$N), δ2.05 (2H, br, Biotin COCH$_2$*CH$_2$CH$_2$CH$_2$), δ1.53 (2H, t, J=7.6 Hz, Biotin COCH$_2$CH$_2$CH$_2$*), δ1.30 (2H, t, J=6.9 Hz, Biotin COCH$_2$CH$_2$*CH$_2$CH$_2$), δ1.17 (2H, t, J=7.1 Hz, Biotin COCH$_2$CH$_2$CH$_2$*CH$_2$).

Thus, an NMR measurement was conducted at 500 MHz in deuterium oxide ($D_2O$) to identify the subject (Compound 12). A collecting rate of a sugar molecule was calculated from the intensity ratio of a first proton of an iduronic acid moiety of NMR to an aromatic proton (based on 16H) in a linker structure. It was estimated from their intensity ratio of 4.1:16 that 4.1 molecules of GlcNS6S-IdoA2S-Glc are collected on the average. The molecular weight (Mw) of a compound having n molecules of GlcNS6S-IdoA2S-Glc collected therein is represented by Formula ⑥ by using a molecular weight of 1120.4 of Compound 10 and a molecular weight increase of 840.97 at the time of one molecule of GlcNS6S-IdoA2S-Glc being collected.

$Mw = 1120.4 + 840.97n$ (Formula ⑥)

n=4.1 was substituted in Formula ⑥ to obtain a molecular weight of 4568.4, from which a yield was calculated to be 42% as described above.

EXAMPLE 4

Synthesis of a Ligand

As for Compound 10 (hereinafter referred to as Biotin Linker 10) serving as the linker compound obtained in Example 1, a ligand was synthesized in order to conduct an SPR measurement on an interaction with a lectin due to a difference in the collecting rate of a sugar molecule.

(4-1 Synthesis of a Ligand with Indefinite Units of Sugar Molecules)

Biotin Linker 10 was used to collect a sugar molecule to obtain a ligand. Since Biotin Linker 10 is soluble in methanol but insoluble in water, a mixed solvent of water, acetic acid, and methanol was used as a reductive amination reaction solvent for collecting a sugar molecule to cause a reaction at pH4.

First, glucose was selected as a sugar molecule to be collected in Biotin Linker 10. Next, a ligand represented by following general formula (19) was synthesized according to the following procedure.

As shown in following general formula (19), 8 equiv. of glucose (2 equiv. per 1-amino group, 8.0 mg, 44 µmol) was used in respect to Biotin Linker 10 obtained in Example 1. Both of them were dissolved in the mixed solvent and stirred overnight at room temperature to obtain a reaction solution of Biotin Linker 10 and glucose. The reaction was tracked by an ESI-MS measurement. A small amount of the Biotin Linker 10/glucose reaction solution under reaction was diluted with methanol to obtain a sample. The sample was measured to confirm the formation of a Schiff base. It was found as a result that the Biotin Linker 10 at this stage predominantly had free amino groups, the generation rate of the Schiff base was low. Accordingly, glucose was added sequentially to the Biotin Linker 10/glucose reaction solution to finally cause glucose (28 equiv.) to react, thereby finding that as a result of the ESI-MS measurement, Biotin Linker 10 exists in the form of a Schiff base. It is to be noted that it is not that all four amino residues became a Schiff base, but that there existed a compound in which only three, two, or one amino residue(s) became a Schiff base.

At this stage, sodium cyanoborohydride was added as a reducing agent to the Biotin Linker 10/glucose reaction solution to reduce the Schiff base. After the reduction reaction, the Biotin Linker 10/glucose solution so reduced was purified with HP-20 (product name) to obtain Compound 16 as a ligand of the present invention.

An ESI-MS measurement was conducted on Compound 16 so obtained to find that a compound including seven or eight molecules of glucose collected therein had been synthesized. This is because glucose further reacted with a secondary amino group resulting from the reduction of the Schiff base due to the addition of a large excess of glucose. A result of the ESI-MS measurement showed that Compound 16 is a ligand mixture having seven or eight units (molecules) of glucose. It is to be noted that Compound 16 was obtained at the yield of 42%, supposing that the compound is an aggregate of eight molecules. Compound 16 is hereinafter abbreviated to 8-Glc.

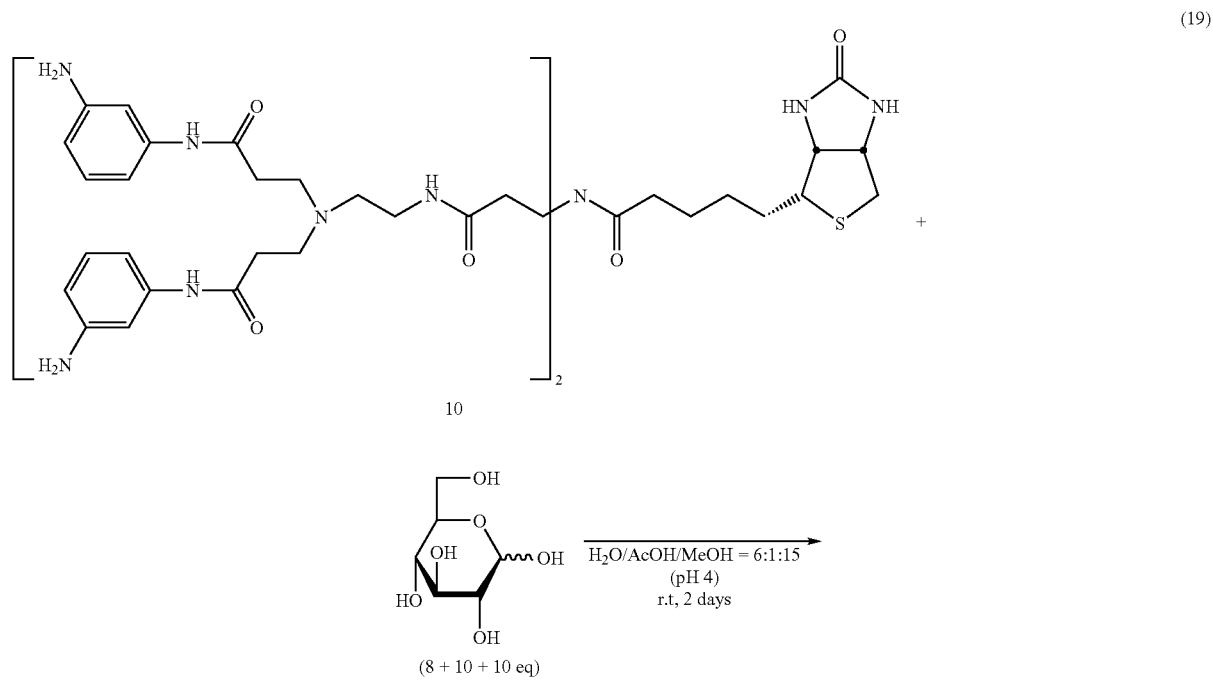

-continued

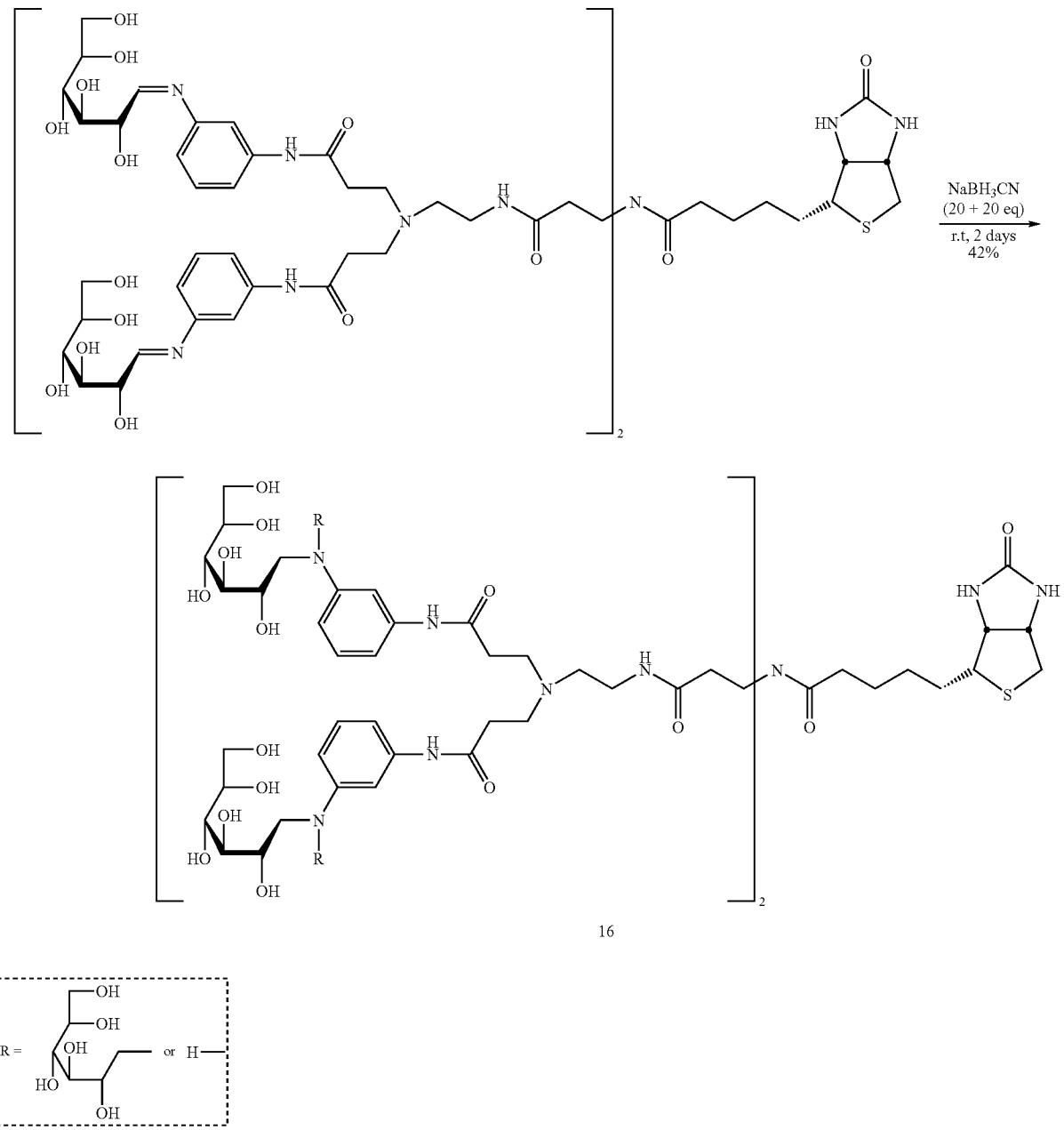

16

Compound 16 was obtained by the following procedure. Biotin Linker 10 (6.0 mg, 5.4 μmol) and glucose (8.0 mg, and 44 μmol) were dissolved in a mixed solvent (water/acetic acid/methanol=6/1/15, 0.4 μmol), stirred overnight at room temperature, further mixed with glucose (10 mg, 55 μmol), mixed again with glucose (10 mg, 55 μmol) after 6 hours, and stirred overnight to obtain a Biotin Linker 10/glucose reaction solution. The Biotin Linker 10/glucose reaction solution was mixed with sodium cyanoborohydride (10 mg, 160 μmol) and stirred overnight at room temperature for a reduction reaction. The Biotin Linker 10/glucose reaction solution so reduced was concentrated under reduced pressure to obtain a residue. The residue was purified with HP-20 (70 mL), and a fraction eluted with water/methanol=1/1 was collected, concentrated, and freeze-dried to obtain a white crystal serving as Compound 16.

Compound 16 was obtained at the yield of 5.1 mg (42%, calculated as 8 substitution products). Also, $^1$H NMR (400 MHz, D$_2$O) measurement was conducted on Compound 16 so obtained to find that δ6.92 (4H, d, J=7.6 Hz, aromatic H), δ6.73 (4H, s, aromatic H), δ6.50–6.45 (8H, br, aromatic H), δ4.30–4.27 (1H, m, Biotin NHCH*CH$_2$S), δ4.05–4.02 (1H, br, Biotin NHCH*CHS), δ3.95–3.91 (8H, m, H-2), δ3.76–3.71 (8H, m, H-5), δ3.65–3.59 (8H×2, m, H-3', H-6'b), δ3.58–3.45 (8H×3, m, H-6'a, H-4', H-1'b), δ3.25 (8H, dd, $J_{gem}$=15.0, $J_{vic}$=9.6 Hz, H-1'a), δ3.19–3.16 (8H, br, Link CH$_2$*CH$_2$NCH$_2$CH$_2$CONHPh, NHCOCH$_2$CH$_2$*NCO), δ2.96–2.86 (1H, m, Biotin NHCHCH*S), δ2.72–2.68 (9H, br, CH$_2$×4+1H, Link NCH$_2$*CH$_2$NHCOPh, Biotin NHCHCH$_2$*S), δ2.54–2.49 (5H, br, CH$_2$×2+1H, Link CH$_2$*NCH$_2$CH$_2$NHCOPh, Biotin NHCHCH$_2$*S), δ2.41 (8H, br, CH$_2$×4, Link NHCOCH$_2$CH$_2$*NCO), δ2.07 (2H, br, Biotin COCH$_2$*CH$_2$CH$_2$CH$_2$), δ2.00 (4H, br, Link NHCOCH$_2$CH$_2$*NCO), δ1.32 (4H, br, Biotin COCH$_2$CH$_2$*CH$_2$CH$_2$*), δ1.17–1.16 (2H, br, Biotin COCH$_2$CH$_2$*CH$_2$CH$_2$). Also, an ESI-MS (positive) measurement was conducted to find that the m/z was 1217.5 [(M8+2H)$^{2+}$], 1135.0 [(M7+2H)$^{2+}$]. It is to be noted that M7 is the molecular weight of a ligand having seven glucose molecules, and M8 is the molecular weight of a ligand having eight glucose molecules.

Next, maltose was collected in Biotin Linker 10 to obtain a ligand.

Biotin Linker 10 obtained in Example 1 was used to synthesize a ligand having a structure represented by general formula (14) according to the following procedure.

As shown in general formula (14), Compound 11 was obtained as a ligand of the present invention by the same procedure as in Example 2 except that an equivalent of maltose (first 9 equiv. and then 9 equiv.) was used.

The collecting rate of maltose in Compound 11 so obtained was calculated from the intensity ratio of a maltose nonreducing end first proton to an aromatic proton (based on 16H) in a linker. It was estimated from their intensity ratio of 5.3:16 that 5.3 maltose molecules are collected on the average. The molecular weight (Mw) of a compound having n maltose molecules collected therein is represented by Formula ① by using a molecular weight of 1120.4 of Compound 10 and a molecular weight increase of 326.3 at the time of one maltose molecule being collected.

$$Mw=1120.4+326.3n \quad \text{(Formula ①)}$$

n=5.3 is substituted in Formula ① to obtain a molecular weight of 2849.8, from which the yield of Compound 11 was calculated to be 88%. Compound 11 is hereinafter abbreviated to 5.3-Mal.

Compound 11 was obtained by the following procedure. Biotin Linker 10 (3.2 mg, 2.9 μmol) and maltose (9.4 mg, 26 μmol) were dissolved in a mixed solvent (water/acetic acid/methanol=6/1/15, 0.2 mL), stirred for 8 hours at room temperature, further mixed with maltose (9.3 mg, 26 μmol), and stirred overnight at room temperature to obtain a reaction solution of Biotin Linker 10 and maltose. The Biotin Linker 10/maltose reaction solution was mixed with sodium cyanoborohydride (approx. 5 mg, 80 μmol), stirred overnight at room temperature, mixed again with sodium cyanoborohydride (approx. 5 mg, 80 μmol), and stirred overnight at room temperature for reduction. The Biotin Linker 10/maltose reaction solution so reduced was concentrated under reduced pressure to obtain a residue. The residue was purified with HP-20 (70 mL), and a fraction eluted with water/methanol=1/1 was collected and concentrated to obtain a residue. The residue was freeze-dried to obtain a white crystal serving as Compound 11.

Compound 11 was obtained at the yield of 7.81 mg (89%, converted as 5.3 substitution products). Also, $^1$H NMR (500 MHz, D$_2$O) measurement was conducted on Compound 11 so obtained to find that δ7.31–6.51 (16H, br, aromatic H), δ5.05 (1H×5.3, br, H-1), δ4.56–4.44 (1H, br, Biotin NHCH*CH$_2$S), δ4.25–4.20 (1H, br, Biotin NHCH*CHS), δ3.92–3.91 (1H×5.3, br, H-2'), δ3.84–3.82 (1H×5.3×3, br, H-5, H-5', H-6b), δ3.78 (1H×5.3×2, dd, $J_{gem}$=13.7, $J_{vic}$=4.5 Hz, H-6a, H-6'b), δ3.72–3.69 (1H×5.3×3, br, $J_{3/4}$=8.2 Hz, H-6'a, H-3', H-3), δ3.67–3.62 (1H×5.3, br, H-4'), δ3.53 (1H×5.3, d, $J_{2/1}$=10.0 Hz, H-2), δ3.41 (1H×5.3, t, $J_{4/3}$=9.5 Hz, H-4), δ3.37–3.36 (4H, br, Link CH$_2$*CH$_2$NCH$_2$CH$_2$CONHPh), δ3.33–3.30 (4H, br, Link NHCOCH$_2$CH$_2$*NCO), δ3.27–3.24 (1H×5.3, br, H-1'b), δ3.17–3.05 (1H×5.3+1H, m, $J_{gem}$=13.1, $J_{vic}$=6.2 Hz, H-1'a, Biotin NHCHCH*S), δ2.88–2.84 (9H, br, CH$_2$×4+1H, Link NCH$_2$*CH$_2$NHCOPh, Biotin NHCHCH$_2$*S), δ2.77–2.70 (1H, br, Biotin NHCHCH$_2$*S), δ2.60–2.65 (4H, br, Link NHCOCH$_2$*CH$_2$NCO), δ2.56 (8H, br, CH$_2$×4, Link NCH$_2$CH$_2$*CONHPh), δ2.20 (2H, t, $J_{B12/B11}$=5.0 Hz, Biotin COCH$_2$*CH$_2$CH$_2$CH$_2$) δ2.18–2.13 (4H, br, Link CH$_2$CH$_2$*NCH$_2$CH$_2$NHCOPh), δ1.59–1.55 (2H, br, Biotin COCH$_2$CH$_2$*CH$_2$CH$_2$), δ1.54–1.43 (2H, br, Biotin COCH$_2$CH$_2$CH$_2$CH$_2$*), δ1.28–1.27 (2H, br, Biotin COCH$_2$CH$_2$CH$_2$*CH$_2$). Also, an ESI-MS (positive) measurement was conducted to find that the m/z was 1702.2 [(M8+2H)$^{2+}$], 1540.3 [(M7+2H)$^{2+}$], 1376.9 [(M6+2H)$^{2+}$]. It is to be noted that M6 is the molecular weight of a ligand having six maltose molecules, M7 is the molecular weight of a ligand having seven maltose molecules, and M8 is the molecular weight of a ligand having eight maltose molecules.

(4–2 Synthesis of a Ligand with Four Units of Sugar Molecules)

In the above example, since a large excess of sugar to be collected was added to Biotin Linker 10, a heterogeneous aggregate including excessive sugar collected therein was obtained. Accordingly, in order to obtain as an object a ligand with four units (molecules) of sugar molecules, an equivalent of a sugar molecule to be added was produced. Glucose, maltose, and lactose were selected as a sugar molecule to be collected.

First, Biotin Linker 10 obtained in Example 1 was used to synthesize a ligand having a structure, wherein Y is represented by O in general formula (16), according to the following procedure.

As shown in following general formula (20), Compound 19 was obtained as a ligand of the present invention in the same procedure as in (4-1) of Example 4 except that when 6 equiv. of glucose was added to Biotin Linker 10 and then glucose was sequentially added to amount 12 equiv. in total, a reducing agent was added even with an unreacted linker still remaining.

(20)
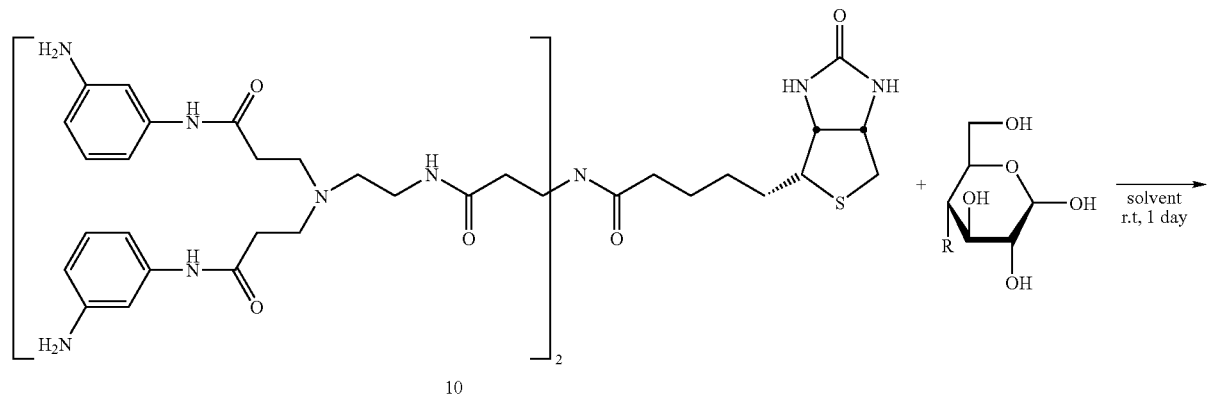
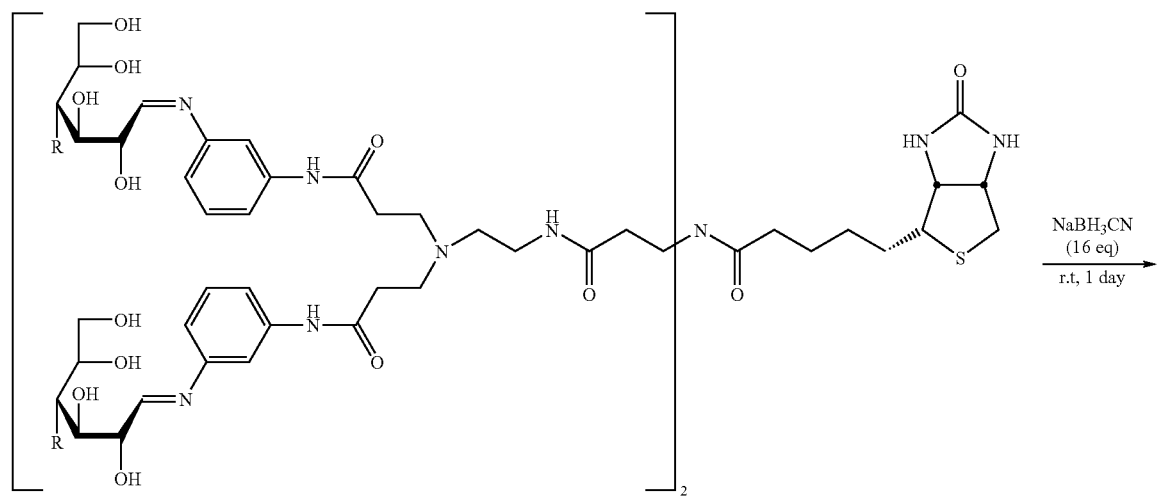
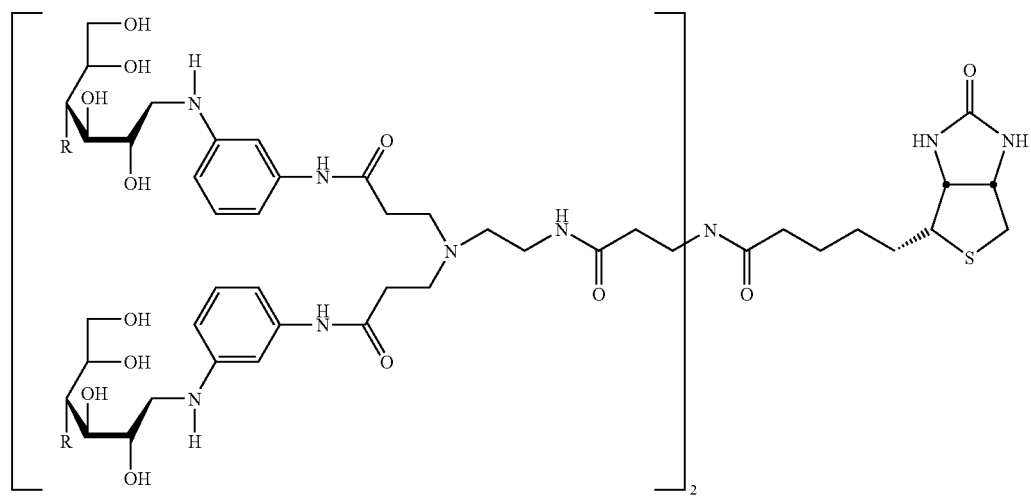

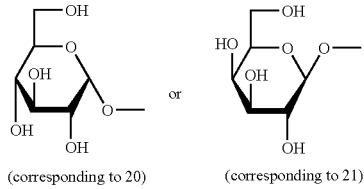

where R = HO— (corresponding to 19) or (corresponding to 20) or (corresponding to 21)

The Biotin Linker 10/glucose reaction solution which had been reduced overnight was purified with HP-20 in the same manner to obtain a product. It is confirmed by an ESI-MS measurement that the product was a mixture of a compound including four or five glucose molecules collected. An NMR measurement being conducted on the product, the collecting rate of glucose was calculated from the intensity ratio of a first proton of glucitol serving as a glucose reductant to an aromatic proton (based on 16H) in a linker. It was estimated from their intensity ratio of 4.2:16 that 4.2 glucose molecules are collected on the average. The molecular weight (Mw) of a compound having n glucose molecules collected therein is represented by Formula ② by using a molecular weight of 1120.4 of Compound 10 and a molecular weight increase of 164.1 at the time of one glucose molecule being collected.

$$Mw = 1120.4 + 164.1n \quad \text{(Formula ②)}$$

n=4.2 is substituted for Formula ② to obtain a molecular weight of 1809.2, from which the yield of Compound 19 was calculated to be 24%. The yield was low because of a loss incurred in purification by HP-20. An equivalent was thus adjusted to synthesize a compound including approximately four glucose molecules collected. Compound 19, which has 4.2 molecules of a glucitol compound at an end thereof, is hereinafter abbreviated to 4-Glc.

Compound 19 was obtained by the following procedure. Biotin Linker 10 (4.91 mg, 3.11 mmol) and glucose (3.45 mg, 19.2 mmol) were dissolved in a mixed solvent (water/acetic acid/methanol=12/1/15, 0.2 mL) and stirred for 8 hours at room temperature to obtain a Biotin Linker 10/glucose reaction solution. The Biotin Linker 10/glucose reaction solution was further mixed with glucose (1.64 mg, 9.1 mmol), stirred overnight at room temperature, mixed with sodium cyanoborohydride (4 mg, 48 mmol), and stirred overnight at room temperature for reduction. The Biotin Linker 10/glucose solution so reduced was concentrated under reduced pressure to obtain a residue. The residue was purified with HP-20 (70 mL), and a fraction eluted with methanol was collected and concentrated to obtain a residue. The residue was freeze-dried to obtain a white crystal serving as Compound 19.

Compound 19 was obtained at the yield of 2.77 mg (35%). Also, $^1$H NMR (500 MHz, $D_2O$) measurement was conducted on Compound 19 so obtained to find that δ7.05–7.02 (4H, m, aromatic H), δ6.86–6.52 (12H, m, aromatic H), δ4.44 (1H, dd, $J_{B7/B6}$=5.3, $J_{B7/B3}$=7.5 Hz, Biotin NHCH*CH$_2$S), δ4.17 (1H, dd, $J_{B3/B4}$=4.5, $J_{B3/B7}$=7.9 Hz, Biotin NHCH*CHS), δ3.92 (4H, td, J=8.6, 4.7 Hz, H-2), δ3.80–3.73 (12H, m, H-3, 6b, 5), δ3.68–3.60 (8H, m, 1H×4×2, H-6a, 4), δ3.30–3.25 (20H, m, 1HΔ4+CH$_2$×2×2, H1a, Link CH$_2$*CH$_2$NCH$_2$CH$_2$CONHPh, CONCH$_2$*CH$_2$CONH), δ3.07 (4H, 1H×4, dd, $J_{gem}$=13.2, $J_{vic}$=8.2 Hz, H1b), δ3.06–3.04 (1H, m, Biotin NHCHCH*S), δ2.86–2.83 (8H, CH$_2$×4, br, Link NCH$_2$*CH$_2$CONHPh), δ2.63–2.61 (4H, m, 2H×2, Link CONCH$_2$CH$_2$*CONH), δ2.54–2.53 (8H, br, CH$_2$×4, Link NCH$_2$CH$_2$*CONHPh), δ2.21–2.06 (6H, br, CH$_2$×3, Link CH$_2$CH$_2$*NCH$_2$CH$_2$CONHPh, Biotin COCH$_2$*CH$_2$CH$_2$CH$_2$), δ1.55 (2H, br, CH$_2$×1, Biotin COCH$_2$CH$_2$*CH$_2$CH$_2$), δ1.43–1.42 (2H, br, CH$_2$×1, Biotin COCH$_2$CH$_2$CH$_2$*CH$_2$), δ1.30–1.23 (2H, br, CH$_2$×1, Biotin COCH$_2$CH$_2$CH$_2$CH$_2$*). Also, an ESI-MS (positive) measurement was conducted to find that the m/z was 911.4 $[(M+2Na)^{2+}]$. It was also found that $[a]_D^{22}$=+0.373 (c 0.0295, $H_2O$).

Next, Biotin Liker 10 obtained in Example 1 was used to synthesize a ligand having a structure, wherein Y is represented by O in general formula (17), according to the following procedure.

As shown in general formula (20), Compound 20 was obtained as a ligand of the present invention in the same procedure as in (4-1) of Example 4 except that 8 equiv. of maltose was used instead of glucose. Compound 20 so obtained has an intensity ratio of 4.1:16 of an end glucose first proton in NMR to an aromatic proton. It was therefore estimated that Compound 20 is a compound including 4.1 maltose molecules collected on the average. The yield of Compound 20 was 69%, calculated by substituting the collecting rate 4.1 for Formula ① in the same manner as in the case of Compound 19. Compound 20, which has 4.1 α-glucose molecules at an end thereof, is hereinafter abbreviated to 4-Mal.

Compound 20 was obtained by the following procedure. Biotin linker 10 (25.0 mg, 15.8 μmol) and maltose (34.3 mg, 95.1 μmol) were dissolved in a mixed solvent (water/acetic acid/methanol=15/1/15, 0.55 mL) and stirred for 9 hours at room temperature to obtain a Biotin Linker 10/maltose reaction solution. The Biotin Linker 10/maltose solution was further mixed with maltose (10.7 mg, 29.7 μmol), stirred overnight at room temperature, mixed with sodium cyanoborohydride (15 mg, 240 μmol), and stirred overnight at room temperature for reduction. The Biotin Linker 10/maltose reaction solution so reduced was concentrated under reduced pressure to obtain a residue. The residue was purified with HP-20 (70 mL), and a fraction eluted with water/methanol=1/1 and methanol was collected and concentrated to obtain a residue. The residue was freeze-dried to obtain a white crystal serving as Compound 20.

Compound 20 was obtained at the yield of 26.7 mg (70%). Also, $^1$H NMR (500 MHz, D$_2$O) measurement was conducted on Compound 20 so obtained to find that δ7.06–7.01 (4H, m, aromatic H), δ6.78–6.77 (4H, m, aromatic H), δ6.70–6.66 (4H, m, aromatic H), δ6.51–6.50 (4H, m, aromatic H), δ5.04 (4H, d, 1H×4, $J_{vic}$=2.7 Hz, H-1), δ4.43 (1H, dd, $J_{B7/B6}$=8.0, $J_{B7/B3}$=4.9 Hz, Biotin NHCH*CH$_2$S), δ4.19–4.17 (1H, br, Biotin NHCH*CHS), δ3.92–3.90 (8H, m, CH×4×2, H-2',5'), δ3.83–3.80 (8H, m, CH×4×2, H-5, 6'a), δ3.73 (8H, dd, CH×4×2, $J_{3/2}$=5.2, $J_{3'/2'}$=5.0 Hz, H-3, 3'), δ3.60 (4H, dd, CH×4, J=7.4, 11.7 Hz, H-4'), δ3.53 (4H, dd, CH×4, $J_{2/3}$=8.0, $J_{2/1}$=3.7 Hz, H-2), δ3.41 (4H, t, CH×4, J=9.5 Hz, H-4), δ3.30–3.22 (12H, m, 1H×4 +CH$_2$×2×2, H1'b, Link CH$_2$*CH$_2$NCH$_2$CH$_2$CONHPh, CONCH$_2$*CH$_2$CONH), δ3.14 (4H, dd, 1H×4, $J_{gem}$=12.9, $J_{vic}$=8.0 Hz, H1'a), δ3.06 (1H, m, Biotin NHCHCH*S), δ2.84–2.83 (9H, br, CH+CH$_2$×4, Link NCH$_2$*CH$_2$CONHPh, Biotin NHCHCH$_2$*S), δ2.70–2.66 (5H, br, CH+CH$_2$×4, Link CONCH$_2$*CH$_2$CONH, Biotin NHCHCH$_2$*S), δ2.62–2.60 (4H, br, CH$_2$×2, Link CONCH$_2$CH$_2$*CONH), δ2.53–2.52 (8H, br, CH$_2$×4, Link NCH$_2$CH$_2$*CONHPh), δ2.20–2.04 (6H, br, CH$_2$×3, Link CH$_2$CH$_2$*NCH$_2$CH$_2$CONHPh, Biotin COCH$_2$*CH$_2$CH$_2$CH$_2$), δ1.55 (2H, br, CH$_2$×1, Biotin COCH$_2$CH$_2$*CH$_2$CH$_2$), δ1.43–1.42 (2H, br, CH$_2$×1, Biotin COCH$_2$CH$_2$CH$_2$*CH$_2$), δ1.30–1.23 (2H, br, CH$_2$×1, Biotin COCH$_2$CH$_2$CH$_2$CH$_2$*). Also, an ESI-MS (positive) measurement was conducted to find that the m/z was 817.0[(M+3H)$^{3+}$]. It was also found that [a]$_D^{22}$=+5.11 (c 0.243, H$_2$O). Calcd for C$_{104}$H$_{165}$N$_{15}$O$_{48}$S.11.9 H$_2$O: C, 47.30; H7.16; N, 7.96%. Found: C, 47.30; H, 6.88; N, 7.86%.

Next, Biotin Linker 10 obtained in Example 1 was used to synthesize a ligand having a structure, wherein Y is represented by O in general formula (18), according to the following procedure.

As shown in general formula (20), Compound 21 was obtained as a ligand of the present invention in the same procedure as in (4-1) except that 8 equiv. of lactose was used instead of glucose. Compound 21 so obtained has an intensity ratio of 4.2:16 of a galactose first proton in NMR to an aromatic proton. It was therefore estimated that Compound 21 is a compound including 4.2 lactose molecules collected on the average. A mass weight can be calculated according to Formula ① also in this case. The collecting rate of 4.2 was substituted to obtain a mass weight of 2477.8, from which a yield was calculated to be 57%. Compound 21, which has 4.2 β-galactose molecules at an end thereof, is hereinafter abbreviated to 4-Lac.

Compound 21 was obtained by the following procedure. Biotin Linker 10 (7.88 mg, 5.0 μmol) and lactose (10.6 mg, 29.4 μmol) were dissolved in a mixed solvent (water/acetic acid/methanol=20/1/15, 0.4 mL) and stirred for 10 hours at room temperature to obtain a reaction solution of Biotin Linker 10 and lactose. The Biotin Linker 10/lactose reaction solution was further mixed with lactose (3.59 mg, 10.0 μmol), stirred overnight at room temperature, mixed with sodium cyanoborohydride (5 mg, 80 μmol), and stirred overnight at room temperature for reduction. The Biotin Linker 10/lactose solution so reduced was concentrated under reduced pressure to obtain a residue. The residue was purified with HP-20 (70 mL), and a fraction eluted with water/methanol=1/1 and methanol was collected and concentrated to obtain a residue. The residue was freeze-dried to obtain a white crystal serving as Compound 21.

Compound 21 was obtained at the yield of 7.08 mg (59%). Also, $^1$H NMR (600 MHz, D$_2$O) measurement was conducted on Compound 21 so obtained to find that δ6.99 (4H, d, J=8.3 Hz, aromatic H), δ6.72 (4H, d, J=6.9 Hz, aromatic H.), δ6.65 (4H, d, J=8.3 Hz, aromatic H), δ6.47 (4H, t, J=6.2 Hz, aromatic H), δ4.38 (4H, d, 1H×4, $J_{vic}$=7.7 Hz, H-1), δ4.35 (1H, m, Biotin NHCH*CH$_2$S), δ4.09 (1H, dd, $J_{B3/B4}$=4.4, $J_{B3/B7}$=7.9 Hz, Biotin NHCH*CHS), δ3.97–3.94 (4H, m, CH×4, H-2'), δ3.84–3.81 (8H, m, CH×4×2, H-5, 5'), δ3.79 (8H, d, CH×4×2, $J_{4/3}$=3.0 Hz, H-4, 6a), δ3.75–3.73 (12H, m, CH×4×3, H-3', 6'a, 6b), δ3.63 (4H, dd, CH×4, $J_{4'/3'}$=6.1 Hz, H-4', 6'b), δ3.57–3.56 (4H, m, CH$_2$×4, Link CH$_2$*CH$_2$NCH$_2$CH$_2$CONHPh), δ3.52 (4H, dd, $J_{3/2}$=10.0, $J_{3/4}$=3.5 Hz, H-3), δ3.49 (4H, t, CH$_2$×2, J=6.3 Hz, Link CH$_2$CH$_2$*NCH$_2$CH$_2$CONHPh), δ3.46 (4H, dd, $J_{2/1}$=7.7, $J_{2/3}$=10.0 Hz, H-2), δ3.29–3.19 (12H, br, CH×4+CH$_2$×4, Link NCH$_2$*CH$_2$CONHPh, H-1'b), δ3.02–2.98 (5H, m, Biotin NHCHCH*S, H-1'a), δ2.81–2.75 (9H, br, CH+CH$_2$× 4, Link NCH$_2$*CH$_2$CONHPh, Biotin NHCHCH$_2$*S), 82.59 (1H, d, $J_{gem}$=13.2 Hz, Biotin NHCHCH$_2$*S), δ2.48 (8H, br, Link NCH$_2$CH$_2$*CONHPh), δ2.13–2.03 (6H, br, Link CONCH$_2$CH$_2$*CONH, Biotin COCH$_2$*CH$_2$CH$_2$CH$_2$), δ1.47 (2H, br, CH$_2$×1, Biotin COCH$_2$CH$_2$*CH$_2$CH$_2$), δ1.35 (2H, br, CH$_2$×1, Biotin COCH$_2$CH$_2$CH$_2$*), δ1.18 (2H, br, CH$_2$×1, Biotin COCH$_2$CH$_2$CH$_2$*CH$_2$). Also, an ESI-MS (positive) measurement was conducted to find that the m/z was 831.3 [(M+3Na)$^{3+}$]. It was also found that [a]$_D^{22}$=−11.3 (c 0.292, H$_2$O). Calcd for C$_{104}$H$_{165}$N$_{15}$O$_{48}$S.10.4H$_2$O: C, 47.78; H, 7.12; N, 8.04%. Found: C, 47.78; H, 6.95; N, 8.00%.

COMPARATIVE EXAMPLE 1

A Ligand Using an Acetyl Linker

In the present example, a linker compound including an acetyl group, instead of biotin, introduced therein was synthesized as a control compound. That is, as shown in following general formula (21), acetic anhydride in pyridine was brought into reaction with Compound 8, i.e., a secondary amine before introduction of biotin for acetylation to obtain Compound 14. Thereafter, a Boc group at an end of Compound 14 was deprotected under the same condition as mentioned before to quantitatively obtain Compound 15. Compound 15 is hereinafter abbreviated to Acetyl Linker 15.

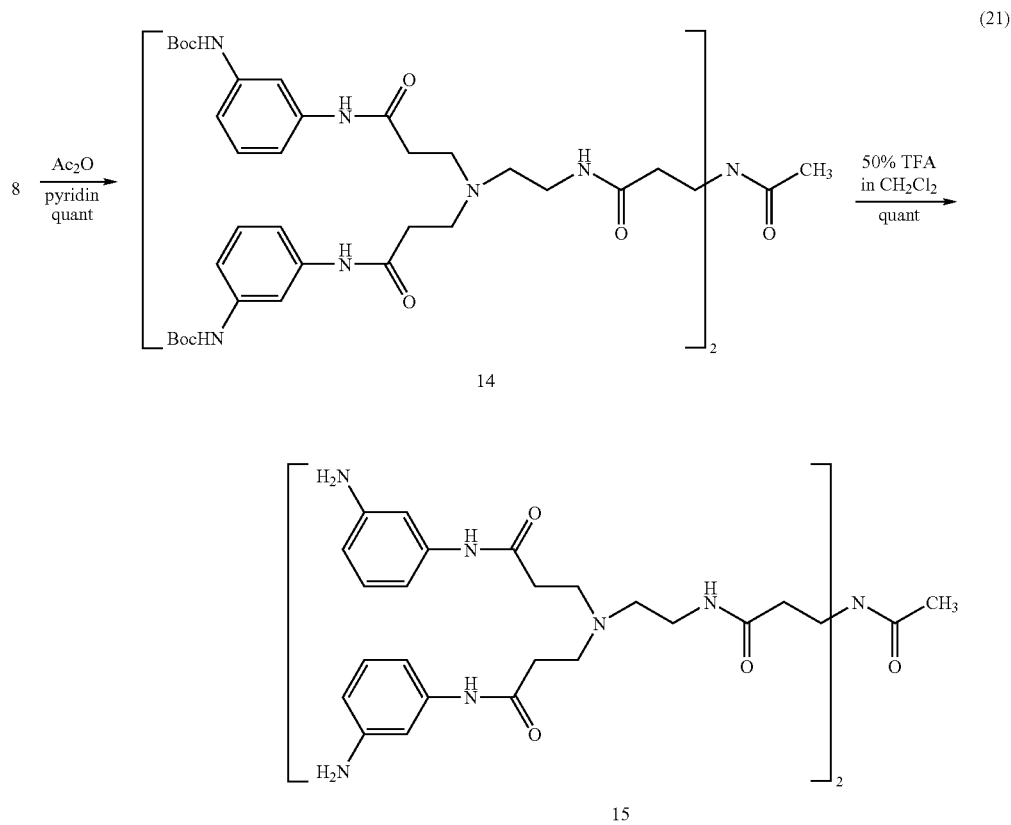

(21)

Compound 14 was obtained by the following procedure. Compound 8 (13.1 mg, 54.5 μmol) was dissolved in pyridine (0.5 mL). The resulting solution was mixed with acetic anhydride (0.5 mL, 5.3 mmol) and stirred for 4 hours at room temperature to obtain a solution. The solution was concentrated under reduced pressure and boiled twice together with toluene to obtain a residue. The residue was purified by medium-pressure silica gel chromatography (5 g, chloroform:methanol=10:1 to 5:1) to obtain a yellow crystal serving as Compound 14.

Compound 14 was obtained at the yield of 12.8 mg (95%). Also, $^1$H NMR (400 MHz, CD$_3$OD) measurement was conducted on Compound 14 so obtained to find that δ7.60 (4H, s, aromatic H), 7.09–6.97 (12H, m, aromatic H), δ3.32 (4H, t, J=6.6 Hz, AceNCH$_2$*CH$_2$CONH), δ3.19–3.17 (4H, br, AceNCH$_2$CH$_2$CONHCH$_2$*), δ2.77 (8H, t, J=6.1 Hz, NCH$_2$CH$_2$*CONHPh), δ2.52 (4H, t, J=6.4 Hz, AceNCH$_2$CH$_2$CONHCH$_2$CH$_2$*), δ2.42 (8H, d, J=6.1 Hz, NCH$_2$*CH$_2$CONHPh), δ2.12 (4H, t, J=6.6 Hz, AceNCH$_2$CH$_2$*CONH), δ1.90 (s, 3H, Me of Ace), δ1.40 (s, 36H, Me of Boc). Also, an ESI-MS (positive) measurement was conducted to find that the m/z was 668.9 [(M+2H)$^{2+}$].

Acetyl Linker 15 was obtained by the following procedure. Compound 14 (12.8 mg, 9.6 μmol) was dissolved in dichloromethane (0.5 mL), mixed with trifluoroacetic acid (0.5 mL), and stirred for 1 hour at 0° C. to obtain a reaction solution of Compound 14 and trifluoroacetic acid. The Compound 14/trifluoroacetic acid reaction solution was concentrated under reduced pressure to obtain a residue. The residue was purified with LH20 (140 mL, eluted by methanol) to obtain a yellow crystal serving as Acetyl Linker 15.

Acetyl Linker 15 was obtained at the yield of 14.9 mg (100%). Also, $^1$H NMR (400 MHz, CD$_3$OD) measurement was conducted on Compound 15 so obtained to find that δ7.50 (4H, s, aromatic H), δ7.27–7.19 (8H, m, aromatic H), δ6.86–6.81 (4H, m, aromatic H), δ3.57–3.51 (12H, br, AceNCH$_2$CH$_2$CONHCH$_2$*, NCH$_2$*CH$_2$CONHPh), δ3.40 (4H, dd, J=6.4 Hz, AceNCH$_2$*CH$_2$CONH), δ3.35–3.32 (4H, br, J$_{5/4}$=5.1 Hz, AceNCH$_2$CH$_2$CONHCH$_2$CH$_2$*), δ2.91 (4H, t, J$_{7/6}$=6.1 Hz, NCH$_2$CH$_2$*CONHPh), δ1.88 (s, 3H, Me of Ace). Also, an ESI-MS (positive) measurement was conducted to find that the m/z was 647.8 [(M+2H)$^{2+}$].

Acetyl Linker 15 obtained as described above was used to collect maltose so as to obtain a ligand. As shown in following general formula (22), Compound 18 was obtained in the same procedure as in (4-1) of Example 4 except that 27 equiv. of maltose was in total brought into reaction with Acetyl Linker 15 instead of glucose being brought into reaction with Biotin Linker 10.

(22)
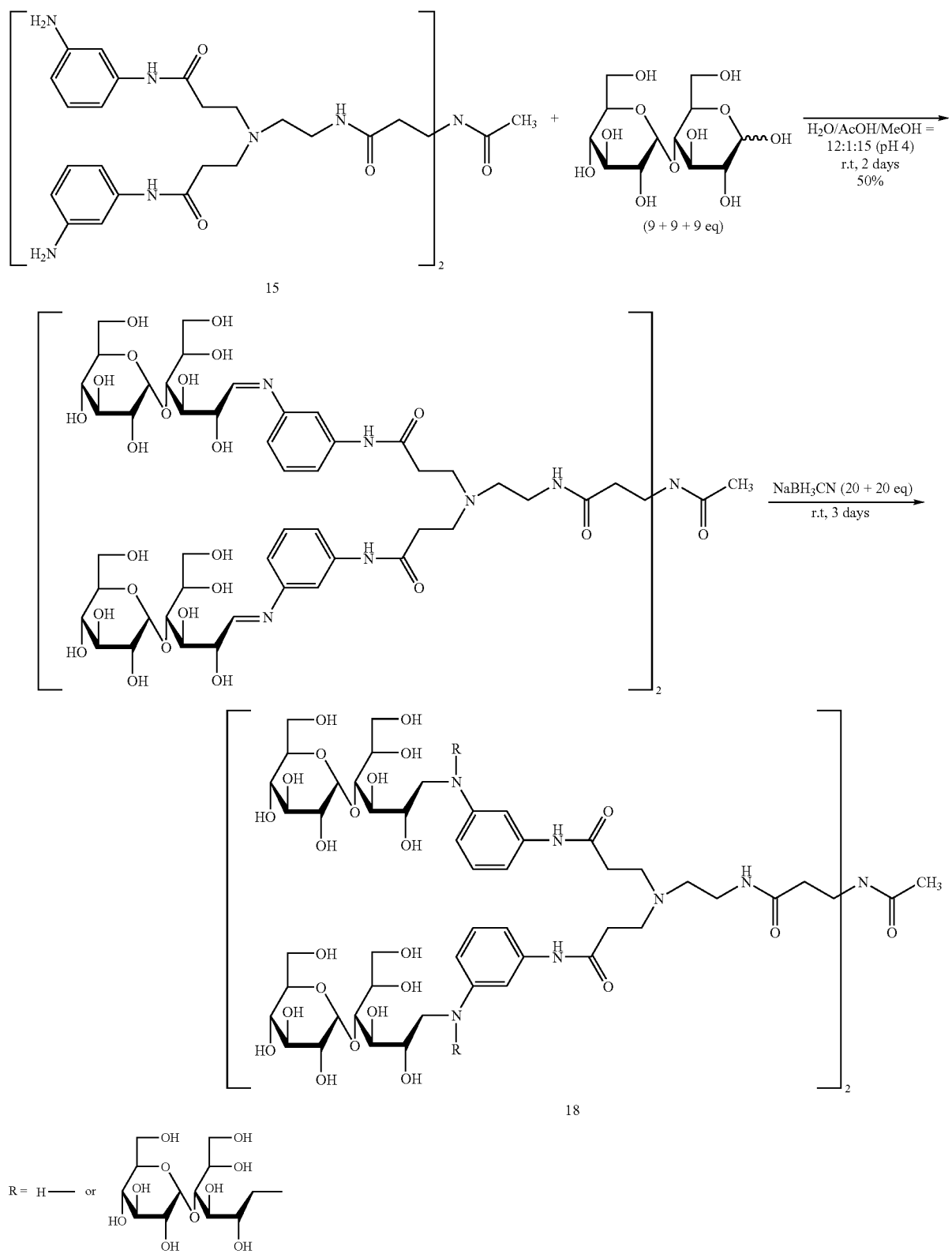

Compound 18 so obtained has an intensity ratio of 7.9:16 of a maltose nonreducing end first proton to an aromatic proton deriving from a linker. It is therefore estimated that Compound 18 is a compound including 7.9 maltose molecules collected on the average. The mass weight (Mw) of a compound including n maltose molecules collected therein is represented by Formula ③ by using a molecular weight of 936.1 of Compound 15 and a molecular weight increase of 326.3 at the time of one maltose molecule being collected.

$$Mw=936.1+326.3n \qquad \text{(Formula ③)}$$

n=7.9 is substituted for Formula ③ to obtain a molecular weight of 3562.8, from which the yield of Compound 18 was calculated to be 50%. Compound 18 is hereinafter abbreviated to Ace-8-Mal.

Compound 18 was obtained by the following procedure. Acetyl Linker 15 (3.73 mg, 7.3 μmol) and maltose (11.5 mg, 33.6 μmol) were dissolved in a mixed solvent (water/acetic acid/methanol=6/1/15, 0.25 mL), stirred overnight at room temperature, further mixed with maltose (13.0 mg, 38.0 μmol), stirred at room temperature, mixed again with maltose (14.7 mg, 42.9 μmol) after 7 hours, and mixed with sodium cyanoborohydride (20 mg, 320 μmol), and stirred overnight at room temperature to obtain a reaction solution. The reaction solution was mixed again with sodium cyanoborohydride (20 mg, 320 μmol) and stirred overnight at room temperature. The solution so mixed again with sodium cyanoborohydride was concentrated under reduce pressure to obtain a residue. The residue was purified with HP-20 (70 mL), and a fraction eluted with water/methanol=1/1 was collected and concentrated to obtain a residue. The residue was freeze-dried to obtain a white crystal serving as Compound 18.

Compound 18 was obtained at the yield of 7.02 mg (50%, converted as 8 substitution products). Also, $^1$H NMR (500 MHz, D$_2$O) measurement was conducted on Compound 18 so obtained to find that δ7.09–7.04 (4H, br, J=7.6 Hz, aromatic H), δ6.93–6.91 (4H, br, aromatic H), δ6.65–6.58 (8H, br, aromatic H), δ5.05 (1H×8, d, J$_{1/2}$=2.3 Hz, H-1), δ3.88 (1H×8×2, br, H-2', 5'), δ3.83 (1H×8, br, H-5), δ3.82 (1H×8, br, H-6b), δ3.74 (1H×8×2, dd, J$_{gem}$=12.4, J$_{vic}$×5.5 Hz, H-6'b, H-6a), δ3.69 (1H×8, br, J$_{3/4}$=9.4 Hz, H-3), δ3.67–3.64 (1H×8×2, br, H-3', 6'a), δ3.59–3.57 (1H×8, br, H-4'), δ3.53 (1H×8, dd, J$_{2/1}$=9.9, J$_{2/3}$=3.5 Hz, H-2), δ3.41 (1H×8, t, J$_{4/3}$=9.6 Hz, H-4), δ3.30 (8H, br, Link CH$_2$*CH$_2$NCH$_2$CH$_2$CONHPh, NHCOCH$_2$CH$_2$*NCO), δ3.24 (1H×8, br, H-1'b), δ3.15 (1H×8, br, H-1'a), δ2.87–2.82 (8H, br, Link NCH$_2$*CH$_2$CONHPh), δ2.66 (4H, br, J=8.0 Hz, Link CH$_2$CH$_2$*NCH$_2$CH$_2$CONHPh), δ2.57 (8H, br, Link NCH$_2$CH$_2$*CONHPh), δ2.10–2.08 (4H, br, J=7.1 Hz, Link NHCOCH$_2$*CH$_2$NCO), δ1.88 (3H, s, Me of Ace). Also, an ESI-MS (positive) measurement was conducted to find that the m/z was 1190.4 [(M8+2Na+H)$^{3+}$], 1081.1 [(M7+2H+Na)$^{3+}$]. It is to be noted that M7 is the molecular weight of a ligand having seven maltose molecules, and M8 is the molecular weight of a ligand having eight maltose molecules.

COMPARATIVE EXAMPLE 2

A Ligand Using a Biotin Linker Having Two Aromatic Amino Residues

For the purpose of comparison, as shown in following general formula (23), Linker Compound 22 (divalent type, referred to as Biotin Linker 22), described in Patent Document 2, which has two aromatic amino residues at an end thereof, was used to collect two units (molecules) of sugar molecules so as to synthesize a ligand.

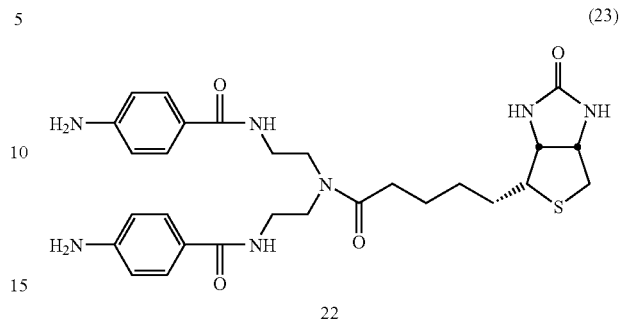

(23)

22

In the same manner as in the case of the ligand, including four units of sugar molecules collected therein, which was obtained in (4-2) of Example 4, Biotin Linker 22 was used to synthesize a ligand including two units of sugar molecules collected therein. It is to be noted that glucose and maltose were chosen as a sugar for assembling two units.

First, glucose was collected in Biotin Linker 22 to obtain Compound 23 serving as a ligand. As shown in following general formula (24), Compound 23 was obtained in the same procedure as in (4-1) of Example 4 except that 4 equiv. of glucose was brought into reaction with Biotin Linker 22 instead of glucose being brought into reaction with Biotin Linker 10. The collecting rate of Compound 23 was calculated from the intensity ratio of a glucitol first proton serving as a glucose reductant to an aromatic proton in Biotin Linker 22 (based on 8H) in an NMR measurement of Compound 23. It was estimated from their intensity ratio of 2.1:8 that Compound 23 includes 2.1 glucose molecules collected on the average. The molecular weight (Mw) of a compound including n glucose molecules collected therein is represented by Formula ④ by using a molecular weight of 567.7 of Biotin Linker 22 and a molecular weight increase of 164.1 at the time of one glucose molecule being collected.

$$Mw=567.7+164.1n \qquad \text{(Formula ④)}$$

n=2.1 is substituted for Formula ④ to obtain a molecular weight of 912.3, from which the yield of Compound 23 was calculated to be 73%. Compound 23 is hereinafter abbreviated to 2-Glc.

Next, maltose was collected in Biotin Linker 22 to obtain Compound 24 serving as a ligand. As shown in following general formula (24), Compound 23 was obtained in the same procedure as Compound 23 had been obtained except that maltose was used instead of glucose. It was found in an NMR measurement of Compound 24 that the intensity ratio of an end glucose first proton to an aromatic proton in Biotin Linker 22 (based on 8H) was 2.0:8. It was therefore estimated that Compound 24 includes 2.0 maltose molecules collected on the average. The molecular weight (Mw) of a compound including n maltose molecules collected therein is represented by Formula ⑤ by using the molecular weight of 567.7 of Biotin Linker 22 and the molecular weight increase of 326.3 at the time of one maltose molecule being collected.

$$Mw=567.7+326.3n \qquad \text{(Formula ⑤)}$$

n=2.0 is substituted for Formula ⑤ to obtain a molecular weight of 1207.2, from which the yield of Compound 24 was calculated to be 76%. Compound 24 is hereinafter abbreviated to 2-Mal.

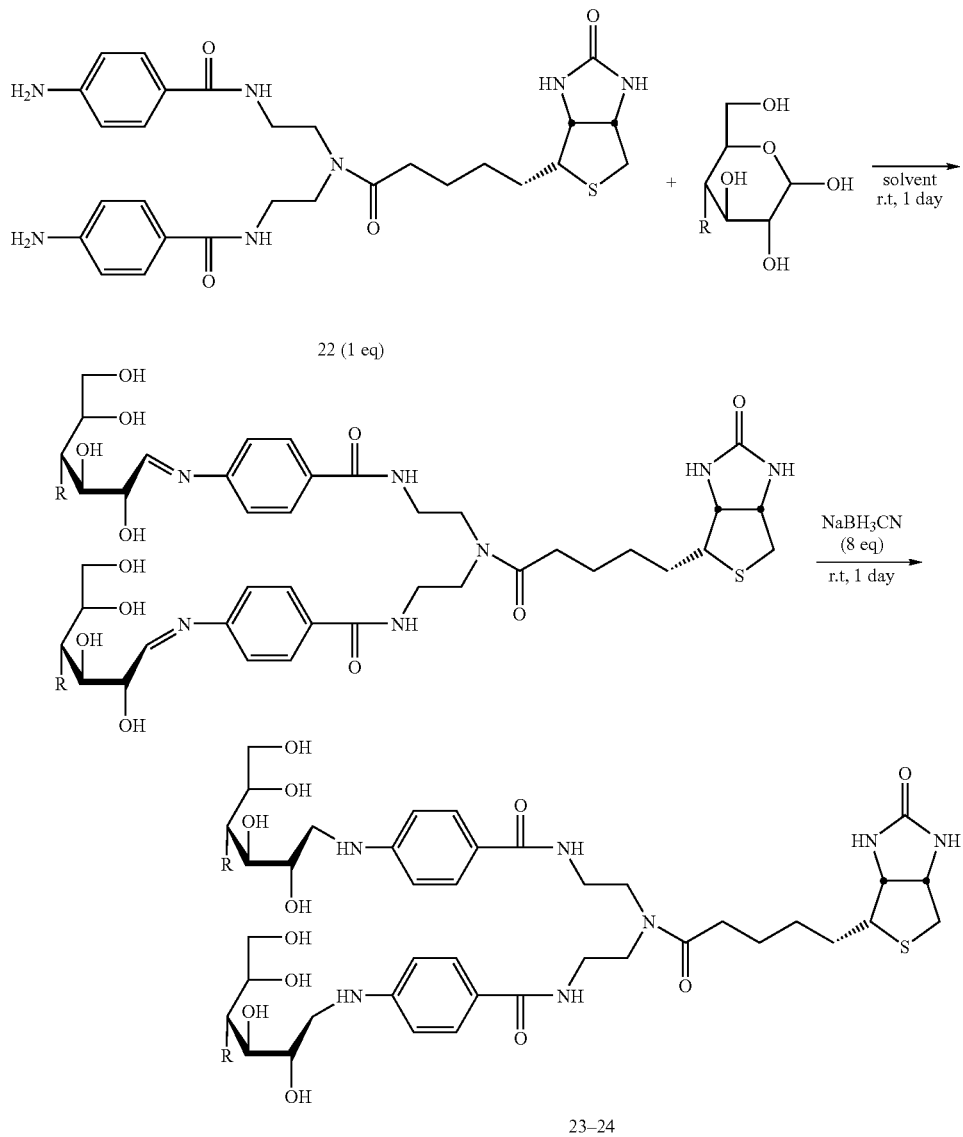

(24)

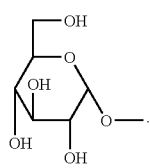

(corresponding to 24)

Compound 23 was obtained by the following procedure. Biotin Linker 22 (4.14 mg, 7.3 μmol) and glucose (3.84 mg, 21.3 μmol) were dissolved in a mixed solvent (water/acetic acid/methanol=6/1/15, 0.25 mL) and stirred for 6 hours at room temperature to obtain a reaction solution of Biotin Linker 22 and glucose. The Biotin Linker 22/glucose reaction solution was further mixed with glucose (1.38 mg, 7.66 μmol), stirred overnight at room temperature, mixed with sodium cyanoborohydride (6 mg, 96 μmol), and stirred overnight at room temperature for reduction. The Biotin Linker 22/glucose solution so reduced was concentrated under reduced pressure to obtain a residue. The residue was purified with HP-20 (70 mL), and a fraction eluted with water/methanol=1/1 was collected and concentrated to obtain a residue. The residue was freeze-dried to obtain a white crystal serving as Compound 23.

Compound 23 was obtained at the yield of 4.84 mg (74%). Also, $^1$H NMR (600 MHz, D$_2$O) measurement was conducted on Compound 23 so obtained to find that δ7.51 (4H, d, J=6.6 Hz, aromatic H), δ6.62 (4H, d, J=9.1 Hz, aromatic H), δ4.33 (1H, dd, $J_{B7/B4}$=3.0, $J_{B7/B6}$=5.0 Hz, Biotin NHCH*CH$_2$S), δ3.88 (2H, dd, $J_{2/1}$=4.4, $J_{2/3}$=4.9 Hz, H-2), δ3.84 (1H, dd, $J_{B3/B4}$=4.4, $J_{B3/B7}$=3.7 Hz, Biotin NHCH*CHS), δ3.75 (2H, dd, $J_{3/2}$=4.9, $J_{3/4}$=3.2 Hz, H-3), δ3.74–3.72 (2H, m, H-6b), δ3.72–3.69 (4H, br, CH$_2$×2, Link NCH$_2$CH$_2$*NHCOPh), δ3.69–3.67 (2H, m, H-5), δ3.64 (4H, t, CH$_2$×2, J=4.6 Hz, Link NCH$_2$*CH$_2$NHCOPh), δ3.60 (2H, dt, $J_{4/3}$=2.5, $J_{4/5}$=7.7 Hz, H-4), δ3.53 (2H, dd, J=2.2, 6.0 Hz, H-6a), δ3.33–3.29 (2H, dt, $J_{gem}$=13.7, $J_{vic}$=4.7 Hz, H-1a), δ3.11 (2H, dt, $J_{gem}$=11.2, $J_{vic}$=3.3 Hz, H-1b), δ2.72 (1H, dd, $J_{gem}$=12.9, $J_{vic}$=5.0 Hz, Biotin NHCHCH$_2$*S), δ2.57 (1H, d, $J_{gem}$=13.2 Hz, Biotin NHCHCH$_2$*S), δ2.55–2.53 (1H, m, J=3.3 Hz, Biotin NHCHCH*S), δ2.14 (2H, t, $J_{B12/B11}$=7.0 Hz, Biotin COCH$_2$*CH$_2$CH$_2$CH$_2$), δ1.22–1.10 (4H, m, CH$_2$×2, Biotin COCH$_2$CH$_2$*CH$_2$CH$_2$*). Also, an ESI-MS (positive) measurement was conducted to find that the m/z was 470.7 [(M+2Na)$^{2+}$]. It was also found that [a]$_D^{22}$=+6.61 (c 0.145, H2O). Calcd for C$_{40}$H$_{61}$N$_7$O$_4$S.6.5H$_2$O: C, 47.45; H, 7.31; N, 9.69%. Found: C, 47.44; H, 6.580; N, 9.60%.

Compound 24 was obtained by the following procedure. Biotin Linker 22 (4.12 mg, 7.3 μmol) and maltose (7.9 mg, 22.1 μmol) were dissolved in a mixed solvent (water/acetic acid/methanol=12/1/15, 0.25 mL) and stirred overnight at room temperature to obtain a reaction solution of Biotin Linker 22 and maltose. Thereafter, the Biotin Linker 22/maltose reaction solution was mixed with sodium cyanoborohydride (6 mg, 96 μmol), stirred overnight at room temperature, and reduced. The Biotin Linker 22/maltose reaction solution so reduced was concentrated under reduce pressure to obtain a residue. The residue was purified with HP-20 (70 mL), and a fraction eluted with water/methanol=1/1 was collected and concentrated to obtain a residue. The residue was freeze-dried to obtain a white crystal serving as Compound 24.

Compound 24 was obtained at the yield of 6.71 mg (75%). Also, $^1$H NMR (500 MHz, D$_2$O) measurement was conducted on Compound 23 so obtained to find that δ7.60 (4H, d, J=4.5 Hz, aromatic H), δ6.74 (4H, d, J=8.8 Hz, aromatic H), δ5.09 (2H, d, $J_{1/2}$=3.7 Hz, H-1), δ4.44 (1H, dd, $J_{B7/B6}$=4.8, $J_{B7/3}$=3.1 Hz, Biotin NHCH*CH$_2$S), δ3.95–3.93 (2H, br, H-2'), δ3.91–3.90 (2H, br, H-5'), δ3.90–3.89 (2H+1H, br, Biotin NHCH*CHS, H-3'), δ3.87–3.86 (2H, br, H-5), δ3.82 (2H, d, $J_{gem}$=12.7 Hz, H-6a), δ3.76 (2H, dd, $J_{gem}$=12.5, $J_{vic}$=5.2 Hz, H-6b), δ3.72 (4H, m, 1H×2×2, $J_{gem}$=12.1, $J_{3/4}$=9.3 Hz, H-6'a, H-3), δ3.66 (4H, br, CH$_2$×2, Link NCH$_2$CH$_2$*NHCOPh), δ3.62 (4H, d, $J_{gem}$=11.8 Hz, H-6'b, H-4'), δ3.58–3.54 (6H, m, CH$_2$×2+1H×2, Link NCH$_2$*CH$_2$NHCOPh, H-2), δ3.42 (2H, t, $J_{4/3}$=9.6 Hz, H-4), δ3.37 (2H, dt, $J_{gem}$=13.7, $J_{vic}$=4.8 Hz, H-1'b), δ3.29 (2H, td, $J_{gem}$=7.4, $J_{vic}$=3.0 Hz, H-1'a), δ2.83 (2H, dd, $J_{gem}$=13.0, $J_{vic}$=5.1 Hz, Biotin NHCHCH$_2$*S), δ2.67 (2H, d, $J_{gem}$=12.8 Hz, Biotin NHCHCH$_2$*S), δ2.65–2.62 (2H, m, Biotin NHCHCH*S), δ2.24 (2H, t, $J_{B12/B11}$=7.0 Hz, Biotin COCH$_2$*CH$_2$CH$_2$CH$_2$), δ1.31–1.19 (4H, m, CH$_2$×2, $J_{B11/B12}$=7.0, $J_{B9/B10}$=7.4 Hz, Biotin COCH$_2$CH$_2$*CH$_2$CH$_2$*), δ0.95–0.91 (2H, m, Biotin COCH$_2$CH$_2$CH$_2$*CH$_2$). Also, an ESI-MS (positive) measurement was conducted to find that the m/z was 632.8 [(M+2Na)$^{2+}$]. It was also found that [a]$_D^{22}$=+6.95 (c 0.222, H$_2$O). Calcd for C$_{52}$H$_{81}$N$_7$O$_{24}$S.9.1H$_2$O: C, 45.13; H, 7.17; N, 7.09%. Found: C, 45.13; H, 6.63; N, 7.37%.

As described above, ligands including four or two units of sugar molecules collected therein was synthesized respectively. The ligands were used to analyze an interaction with a protein by an SPR measurement.

EXAMPLE 5

A Specific Interaction Between a Sugar Molecule and a Protein Using the SPR Method In most SPR measurements, an analyte nonspecifically interacts with a molecule other than a ligand. Therefore, in an actual measurement, the sum of a resonant angle change caused by a specific interaction and a nonspecific interaction is observed. The biggest problem for measurement is to observe a specific interaction while suppressing a nonspecific interaction. The inventors thought that the problem could be solved by the following method (referred to as a 2-channel analysis method).

Figure 3:
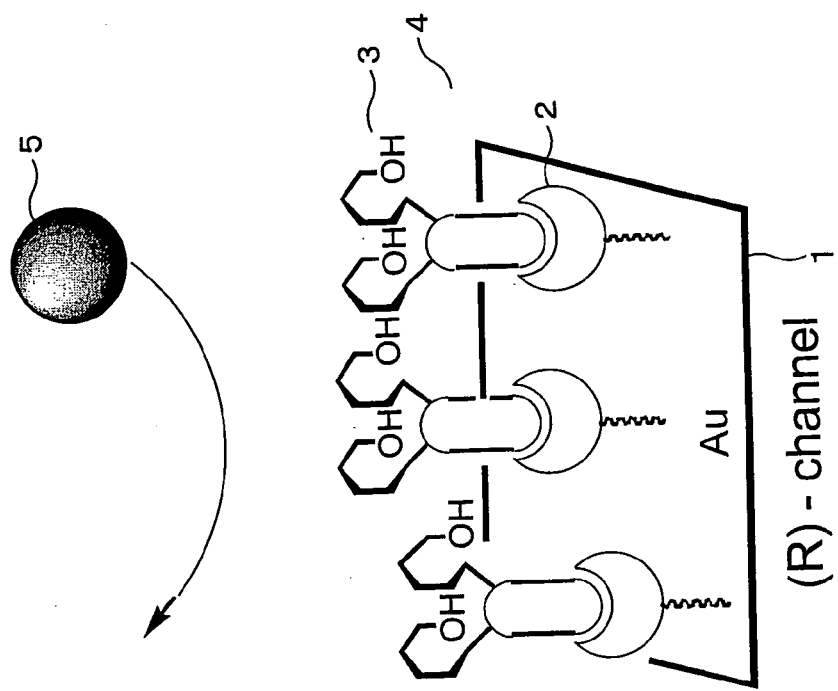
FIG. 3 is a schematic diagram showing a "2-channel analyzing method" used for an SPR measurement of a ligand of the present invention.
Figure 3:
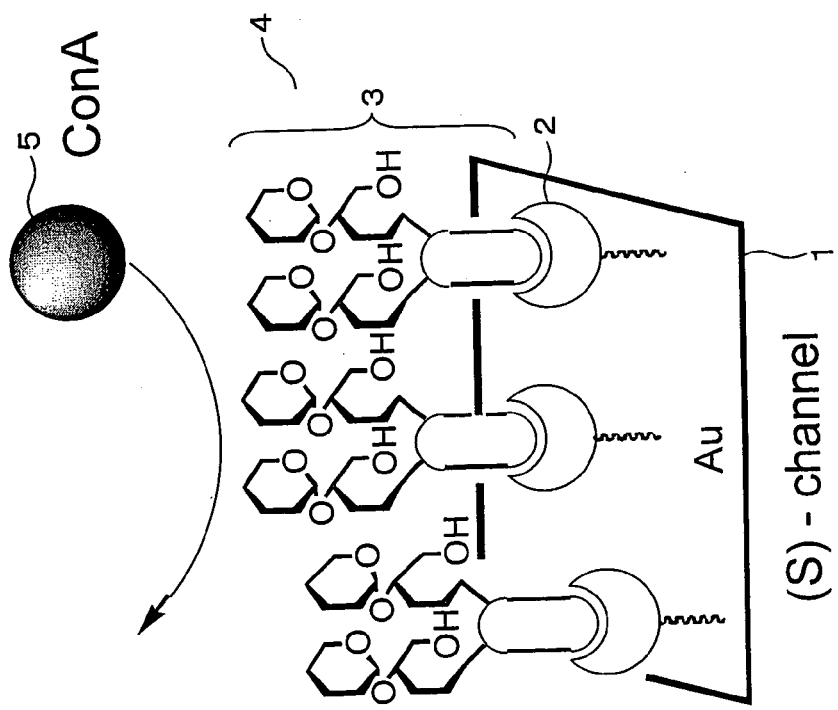

SPR670 (product name, Nippon Laser & Electronics LAB), which is an apparatus, used in the present example, for conducting an STR measurement, has two channels (S) and (R) and makes it possible, as shown in FIG. 3, to simultaneously observe interactions between a ligand on respective surfaces and an analyte. For example, supposing that concanavalin A (Con A) serving as a lectin which binds to glucose is simultaneously flown onto the two surfaces under the same conditions with 4-Mal immobilized on one surface and 4-Glc on the other, Con A may bind to glucopyranose present at an end of 4-Mal but may hardly bind to 4-Glc, which does not have glucopyranose. Since 4-Mal and 4-Glc have the same structure except for the presence or absence of a sugar at an end thereof, a difference between the interactions with Con A can be attributed to glucopyranose. That is, the observed difference between resonant angle changes between (S) and (R) is equivalent to a specific interaction between glucopyranose and Con A.

Thus, the inventor found that a specific interaction between a sugar molecule and a protein can be detected by using, as ligands, compounds which have the same structure except the presence of a sugar at an end thereof through application of a conventional method for observation of a difference in interaction between two different types of ligand immobilized onto (S) and (R) respectively.

(5–1 Preparation of a Ligand-introduced Chip)

In the beginning, a ligand was immobilized onto a sensor chip in order to analyze an interaction between a sugar molecule and a protein by an SPR measurement. That is, the ligand synthesized in Example 4 was immobilized onto the chip through a biotin-avidin bond to obtain a ligand-introduced chip (ligand carrier). It is to be noted that the ligand was immobilized after avidin had been immobilized onto the SPR sensor chip.

The ligand-introduced chip was obtained by the following procedure. In the beginning, a sensor chip (manufactured by Japan Laser Electronics Co., Ltd.), prepared by depositing a gold thin film of 50 nm thick on a glass substrate of 13 mm×20 mm×0.7 mm, was placed in a UV ozone cleaner (product name: NL-UV253, Japan Laser Electronics Co., Ltd.) and was exposed to ultraviolet rays for 20 minutes so as to wash the surface of the sensor chip with ozone. Next, the sensor chip was immersed in a 4,4'-methanol dithiobutyrate solution (100 μM) in a Petri dish and gently shaken for 30 minutes at room temperature (product name: Bio Dancer, New Brunswick Scientific Co., Ltd.). 4-thiobutyric acid was immobilized onto the chip through a gold-sulfur bond. The chip was washed three times with ethanol. Thereafter, the chip was immersed in a mixed solution of an aqueous solution (1 mL) of 160 mM carbodiimide and 9 mL of 13 mM N-hydroxysuccinimide 1,4-Dioxan solution (9 mL) in a Petri dish and gently shaken for 30 minute at room temperature. Water (10 mL) was added to the Petri dish and shaken for 5 minutes at room temperature to terminate the activation reaction. The chip was washed with water four times, air-dried, and then mounted on a sensor chip cartridge of SPR670. A running buffer was flown onto the chip mounted on the sensor chip cartridge. A laser beam was irradiated onto the gold film. A surface plasmon resonant angle change then observed was monitored. It is to be noted that a phosphate buffer solution (PBS) at pH 7.4 was used as the running buffer, and the running buffer was flown onto the chip at a flow rate of 5 mL/min except when a sample was flown. Also, all SPR measurements were conducted at a constant temperature (25° C.). All sample solutions used in the measurements were used after filtration by a syringe filter (© Whatman PURADISC™ 25TF 0.2 mm PTFE Membrane filter).

After the running buffer had been flown onto the chip and the resonant angle change had become constant, 60 μL of aqueous solution of 0.1 mg/mL neutroavidin (PIERCE, NeutrAvidin™, CA47105) sodium acetate (10 mM, pH 5.5) was flown three times at a flow rate of 5 μL/min. After a sample solution was flown in SPR, the solution was switched from the sample solution to a buffer solution so as to wash away an excess sample. After a resonant angle change became constant, the next operation was performed. In order to inactivate (capping) residual active ester, 60 μL of PBS solution (pH 8.5) containing 1.0 M aminoethanol was flown twice at a flow rate of 5 μL/min to obtain an avidin additive chip (avidin adduct).

Subsequently, PBS solutions of various concentrations of the ligands obtained in Example 4 were sequentially flown by 60 μL at a flow rate of 10 μL/min so as to immobilize the ligands onto the avidin additive chip, thereby obtaining a ligand-introduced chip (ligand carrier). It is to be noted that the immobilization of the ligands had been repeated until an increase in resonance unit was not recognized in an SPR sensorgram.

FIG. 4 shows one example of the SPR sensorgram until the immobilization of the ligands. It is to be noted here that 4-Mal, which had been obtained in (4-3) of Example 4, was immobilized onto the S channel (hereinafter referred to as (S)), and 4-Glc was immobilized onto the R channel (hereinafter referred to as (R)). The horizontal axis of the sensorgram represents time; the vertical axis of the sensorgram represents resonant angle change (Response (RU; Response Unit)).

Except when an analyte is added, a phosphate buffer solution (pH 7.4, hereinafter referred to as a PBS) serving as a running buffer is constantly flown onto a chip at a flow rate of 5 μL/min. When the addition of the analyte onto the chip was completed, the PBS was arranged to be automatically flown to wash an excess analyte which had not been involved in the binding. When a 0.1 mg/mL neutroavidin sodium acetate solution (10 mM sodium acetate, ph 5.5) was flown by 60 μL at a flow rate of 5 μL/min, an increase in resonant angle was observed. It was therefore found that neutroavidin had been immobilized onto the chip.

In order to cap active ester remaining on the chip thereafter, a PBS solution containing 1.0 M ethanolamine was flown by 60 μL at a flow rate of 5 μL/min. After the capping, a resonant angle change quantity between a point of time when the resonant angle change had become constant and a point of time before and after the flowing of the neutroavidin solution was defined as an immobilization quantity. In this sensorgram, the immobilization quantity in (S) was 3690 RU and that in (R) was 3480 RU.

Next, 4.9 μM, 16.3 μM, and 49 μM 4-Mal solutions were flown onto (S) by 60 μL at a flow rate of 10 μL/min for immobilization; 0.49 μM and 4.9 μM 4-Glc solutions were flown onto (R) by 60 μL at a flow rate of 10 μL/min for immobilization. An excess ligand which had not been immobilized was washed away. A resonant angle change quantity between a point of time when the resonant angle change had become constant and a point of time before the immobilization was defined as a immobilization quantity. It is to be noted that the immobilization of the ligands had been repeated until a state was achieved in which a flowing of an aggregate does not increase the immobilization quantity. In this sensorgram, the immobilization quantity of 4-Mal was 220 RU and that of 4-Gcl was 220 RU. Thus, ligand-introduced chips including two different ligands respectively immobilized to the same extent were produced. In the same manner, various ligand-introduced chips including different ligands were produced.

(5–2 Verification of the Immobilization of a Ligand)

Compound 18 was used to verify whether a synthesized ligand is immobilized on a chip through a biotin-neutroavidin bond. Compound 18 includes maltose collected by Acetyl Linker 15, not having biotin, which was obtained in Example 1. That is, under the same conditions as 5.3-Mal, Ace-8-Mal was flown onto a chip having neutroavidin immobilized thereon. If Ace-8-Mal is not immobilized, it can be confirmed that there is no immobilization of a nonspecific ligand.

Figure 5:
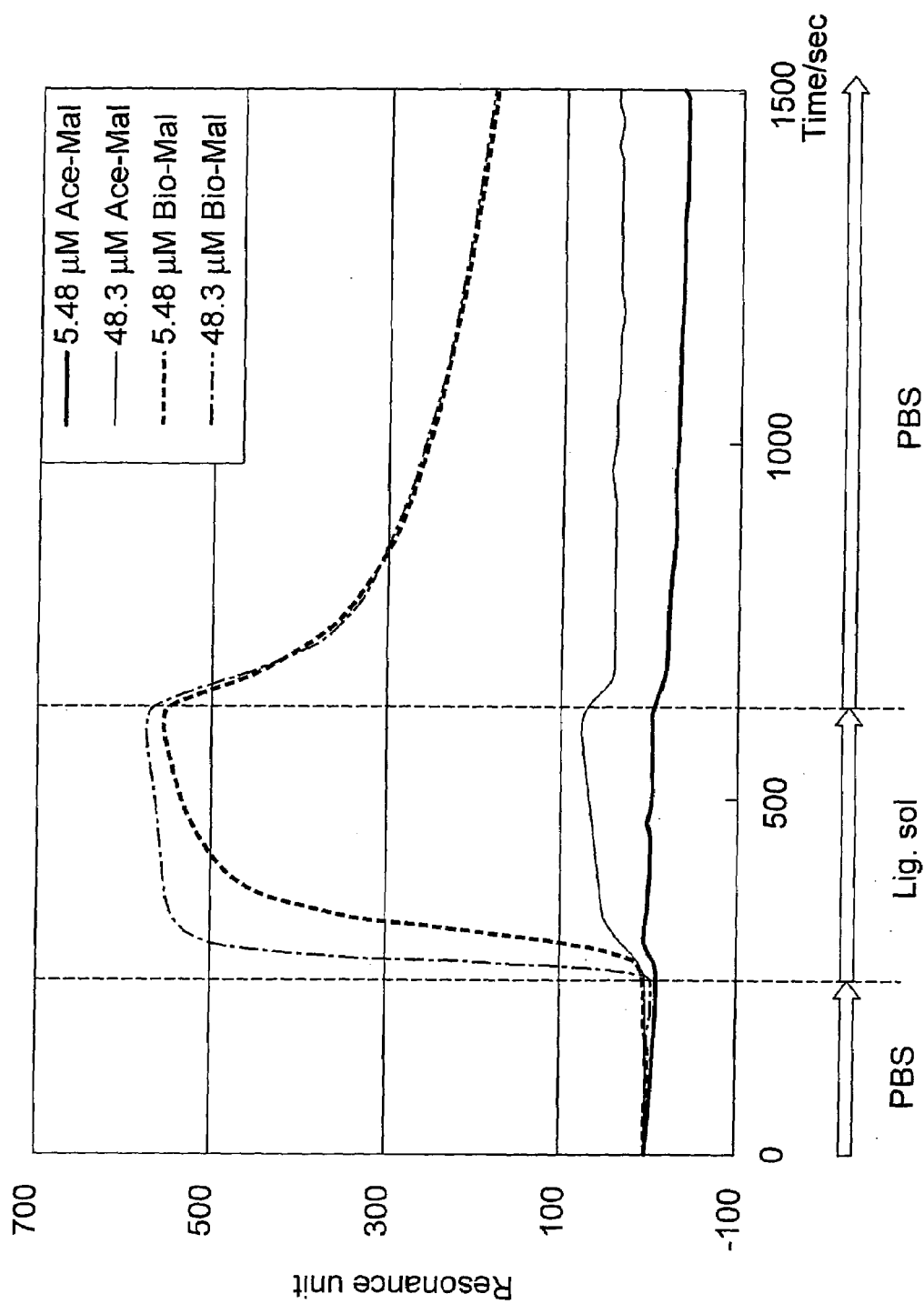
FIG. 5 is a graph showing a result of an SPR measurement showing an interaction between a ligand (Mal-Bio) of the present invention and a ligand (Ace-Mal) of Comparative Example.

In the beginning, an avidin additive chip including neutroavidin immobilized in the same manners as in (5–1) was produced. At this time, the neutroavidin immobilization quantity in (S) was 6620 RU and that in (R) was 6330 RU. An Ace-8-Mal solution (0.61 μM), an Ace-8-Mal solution (5.48 μM), a 5.3-Mal solution (0.61 μM), and a 5.3-Mal solution (5.48 μM) were sequentially flown onto (S) of the chip by 60 μL at a flow rate of 10 μL/min; only a PBS was constantly flown onto (R). FIG. 5 is a sensorgram, drawn in a superposition manner, of (D) corresponding to a difference between (S) and (R). It is to be noted in FIG. 5 that Ace-8-Mal is referred to as Ace-Mal and 5.3-Mal is referred to as Bio-Mal.

As shown in FIG. 5, it was found from an SPR measurement result that while 5.3-Mal containing biotin was specifically immobilized onto the chip, Ace-8-Mal not containing biotin was not immobilized at all. Therefore, a compound (ligand) using a biotin linker to collect a sugar molecule could be specifically immobilized onto the chip through the biotin-avidin (neutroavidin) bond.

(5-3 An Interaction Between a Sugar Molecule and a Lectin Using a Ligand-introduced Chip)

PBS solutions containing proteins of various concentrations were flown onto the ligand-introduced chip obtained in (5-1) by 60 μL at a flow rate of 20 μL/min so as to observe the binding and dissociating behavior of the ligand-introduced chip with each protein by an SPR measurement.

The following proteins were used.

BSA (SIGMA ALUBMUN, BOVINE)
Concanavalin A (SEIKAGAKU KOGYO)
Pea Lectin (SEIKAGAKU KOGYO)
Peanut Lectin (SEIKAGAKU KOGYO)
$RCA_{120}$ (SEIKAGAKU KOGYO)

It is to be noted that an aqueous solution of sodium hydroxide (10 mM) was flown onto a surface of the ligand chip, which includes the protein introduced thereinto, by 60 μL at a flow rate of 60 μL/min for dissociation, recycling, and reuse. This operation had also been repeated one to three times until the resonance unit value (Response (RU; Response Unit)) before the flowing of a lectin in the sensorgram was achieved.

First, an interaction with Con A was examined by the ligand-introduced chips, obtained in (5-1), onto which 5.3-Mal and 8-Glc were immobilized. Neutroavidin was immobilized onto the chip in the same manner as in (5-1) to obtain an avidin additive chip. At this time, the neutroavidin immobilization quantity of neutroavidin of (S) was 5470 RU and that of (R) was 4380 RU. Thereafter, 5.3-Mal was immobilized onto (S) of the avidin additive chip and 8-Glc was immobilized onto (R) of the avidin additive chip to obtain ligand-introduced chips. It is to be noted that (S) had a ligand immobilization quantity of 390 RU and (R) had a ligand immobilization quantity of 390 RU.

Figure 6:
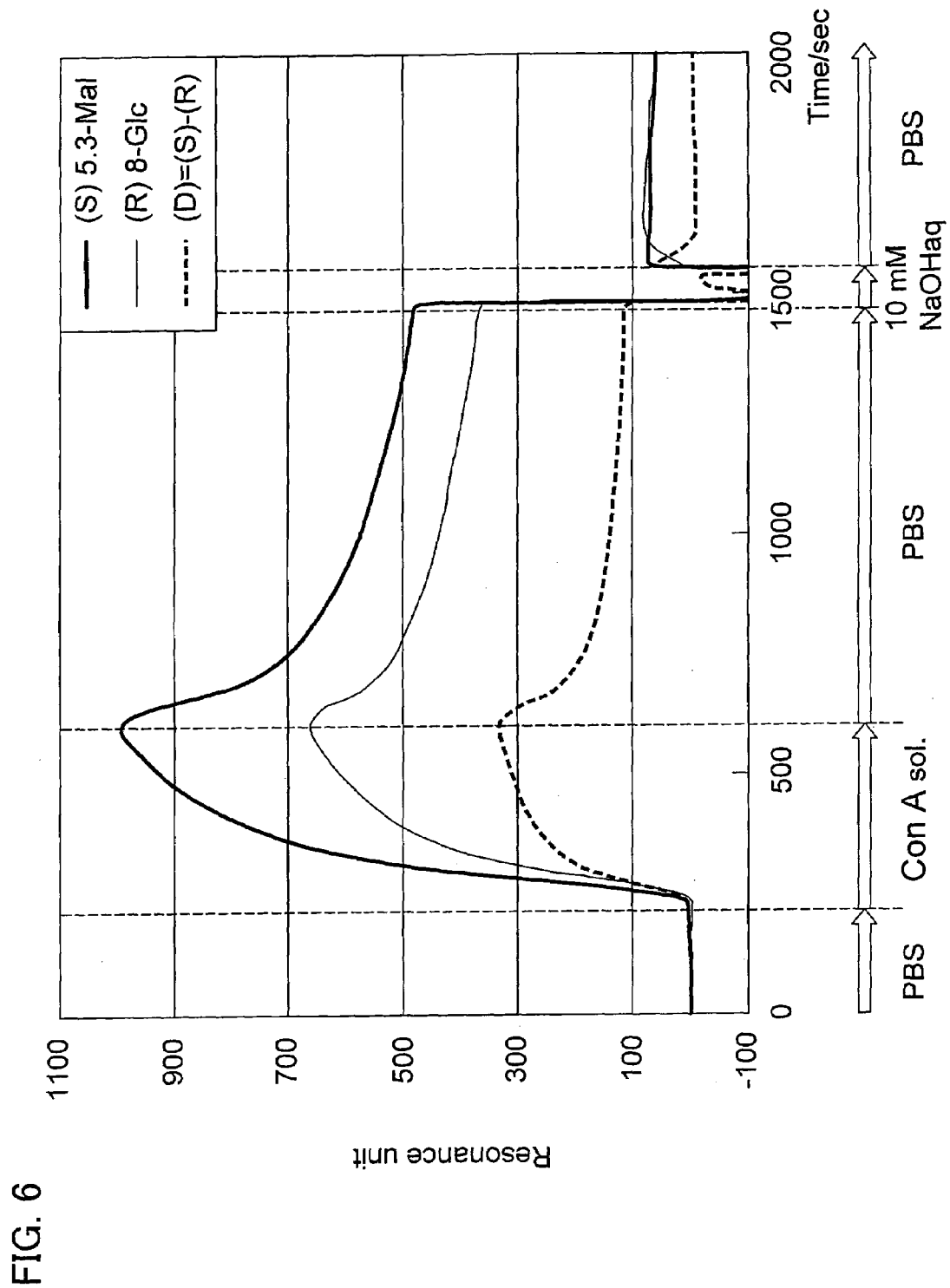
FIG. 6 is a graph showing a result of an SPR measurement showing an interaction between a ligand 5.3-Mal and 8-Glc of the present invention and concanavalin A.

Onto the ligand-introduced chips thus produced, a Con A solution (1.0 M) was flown by 60 μL at a flow rate of 10 μL/min. FIG. 6 shows a resonant angle change in (S), that in (R), and that in (D) corresponding to a difference between (S) and (R). As shown in FIG. 6, the flowing of the Con A solution caused the ligand on the ligand-introduced chip to bind to Con A, so that the resonant angles increased in both (S) and (R). Next, Con A which had not been involved in the binding was washed away, and a PBS was flown for 1000 seconds at a flow rate of 10 μL/min. Thereafter, an aqueous solution of sodium hydroxide (10 mM) was flown by 60 μL at a flow rate of 60 μL/min so as to dissociate Con A binding to the ligand. From the fact that the dissociation caused the resonant angle to suddenly decrease to become constant at the same level as the baseline before the flowing of Con A, it was found that Con A was completely dissociated. (D) in FIG. 6 became the same as a typical SPR sensorgram representing binding and dissociation. That is, the system made it possible to observe a specific interaction between Con A and glucopyranose.

Moreover, Con A of various concentrations was acted on the ligand-introduced chip so as to conduct an SPR measurement on an interaction. Also, an SPR measurement was also conducted on an interaction with BSA and PSA so as to observe a resonant angle change.

From the result, it became apparent that a ligand which includes a sugar molecule collected thereon by a synthesized biotin linker can be immobilized onto a chip which includes avidin (neutroavidin) immobilized thereon and makes it possible to analyze a specific interaction between Con A and glucopyranose.

Further, it was concluded that the "2-channel analysis method" using a ligand-introduced chip makes it possible to cancel out a nonspecific interaction with a protein. Also, as is the case with Con A, from the fact that PSA serving as a glucopyranose recognition lectin had not specifically interacted, it was found that even a lectin capable of recognizing a sugar differs in binding degree from a sugar molecule immobilized onto a chip.

Further, ligand-introduced chips were produced which includes 4-Mal and 4-Glc of the present invention and 2-Mal and 2-Glc serving as a comparative example immobilized thereon. Con A, BSA, PSA, $RCA_{120}$, and PNA solutions of various concentrations were flown onto the ligand-introduced chips so as to observe a resonant angle change by an SPR measurement.

Table 1 shows differences in interaction with a lectin due to the collecting degrees of the sugar molecules.

| Ligand | Protein | $K_D$/μM | $k_a$/$s^{-1}M^{-1}$ × $10^4$ | $k_d$/$s^{-1}$ × $10^{-2}$ |
|---|---|---|---|---|
| 4-Mal, 4-Glc | 1.0 μM Con A | 0.59 ± 0.06 | 1.2 ± 0.12 | 0.72 ± 0.021 |
| 2-Mal, 2-Glc | 1.0 μM Con A | 0.96 ± 0.05 | 1.5 ± 0.86 | 1.4 ± 0.86 |

$K_D$ ($k_d/k_a$): dissociation constant,
$k_a$: binding velocity constant,
$k_d$: dissociation velocity constant Table 1 shows that the smaller the dissociation constant ($K_D$) value is, the stronger the intermolecular binding affinity is. Comparison of the dissociation constants in respect to the same analyte by Table 1 indicates that the system including four units of sugar molecules collected therein has about ⅔ times as large a numerical value as the system including two units of sugar molecules collected therein. That is, it was confirmed that the bonding with Con A became stronger by collecting more sugars.

The binding velocity constant ($k_a$) and dissociation velocity constant ($k_d$) of Con A and those of the ligands were compared for a further detailed examination, so that the following became apparent. It was found that whereas there was not a difference in binding velocity between Con A and the ligands, there was a comparatively big difference in dissociation velocity in that the ligand having four units of sugar molecules has about ½ times as high dissociation velocity as the ligand having two units of sugar molecules. That is, it was found that the ligand having four units of sugar molecules is less prone to dissociate Con A binding thereto. When the number of sugar molecules to be collected was increased, there was not a change in binding velocity. However, this gave Con A more opportunities to rebind to the ligand after dissociation, thereby lowering dissociation velocity. It is conceivable that this caused the dissociation constant to have a small numerical value. From the result, it was confirmed that a linker compound of the present invention collects a sugar molecule and causes a cluster effect to strengthen the bonding with a molecule which interacts.

Next, the sugar molecule being changed, an interaction between galactose and a galactose recognition lection was analyzed. A ligand-introduced chip was used which includes a neutroavidin chip and 4-Lac and 4-Gal immobilized thereon. 4-Lac and 4-Gal differ from each other in the presence of the end galactose obtained in (5-1). $RCA_{120}$ of different concentrations and PNA were used to conduct the same SPR measurement as described above. Con A, BSA, PSA, $RCA_{120}$, and PNA solutions of various concentrations were flown onto the ligand-introduced chips, onto which 4-Lac and 4-Glc were respectively immobilized, to conduct an SPR measurement so as to observe a resonant angle change (D). From the observation results, it became apparent that the use of a ligand including lactose collected thereon makes it possible to analyze a specific interaction of galactose with a galactose-binding lectin $RCA_{120}$ and PNA.

The following can be said from the SPR measurement result obtained above.
1) A ligand including a sugar molecule collected thereon by a linker synthesized in the present research could be immobilized onto an SPR sensor chip through a biotin-avidin (neutroavidin) bond.
2) The "2-channel analysis method", i.e., a method which uses control ligands having the same structure except a sugar molecule at an end thereof, made it possible to cancel out a nonspecific interaction, which makes the biggest problem in an SPR measurement, so as to detect a specific interaction between a sugar and a protein.
3) The use of a sugar chip including sugar ligands of different collecting rates immobilized thereon made it possible to observe the reinforcement of the bonding of a sugar molecule with a lectin by a cluster effect.

As described above, a linker compound of the present invention collecting a sugar molecule, an aggregate to be obtained (ligand-introduced chip) can be sufficiently applied to analyzing an interaction between a lectin and a sugar molecule by an SPR measurement.

EXAMPLE 6

Affinity Chromatography (6–1 Preparation of an Affinity Column)

The ligand obtained in Example 4 was used to produce an affinity column.

Following a general producing method of an affinity column, an affinity column including the ligand 4-Mal, obtained in Example 4, immobilized thereto. As a column carrier, Hitrap NHS-activated Hp (column volume 1 mL; manufactured by Amersham Co., Ltd.) was used. The column carrier, including a gel matrix and N-hydroxysuccinimide serving as an active group immobilized thereon through a spacer (10 mmol NHS group per 1 mL gel), is suitable to immobilizing onto a carrier a compound having an amino group. FIG. 6 is a schematic diagram showing the steps for preparation of an affinity column.

Solutions were manually flown into a column with a syringe of 1 mL or 5 mL (product name: Terumo Syringe, sterilized by gamma rays 1 mL, 5 mL) so that the solutions were flown from a bottom edge of the column at a flow rate of one drop per second. Also, all the solutions were used after filtration by a syringe filter (Millex-GS Syringe Drive Filter Unit 0.22 μm). The following solutions 1 to 3 were produced as a buffer.

1) Neutroavidin coupling buffer (an aqueous solution of 10 mM sodium acetate pH 5.5 containing 0.5 M sodium chloride)

2) Blocking buffer (an aqueous solution of 0.1 M ethanolamine pH 8.3 containing 0.5 M sodium chloride)

3) Washing buffer (an aqueous solution of 0.1 mM sodium acetate pH 4.0 containing 0.5 M sodium chloride)

Through an activating column (Hitrap NHS-activated HP; manufactured by Amasharm Co., Ltd.) filled with a gel carrier including N-hydroxysuccinimide immobilized thereon, ice-cooled 1 mM hydrochloric acid (1 mL) was flown so as to remove isopropanol which had been filled in the column. Right after that, the 2.0 mg/mL neutroavidin coupling buffer solution (1 mL) was flown through the column. The column was sealed and left for 30 minutes at room temperature. Then, the blocking buffer solution (6.0 mL) was flown through the column. The column was sealed and left for 30 minutes at room temperature. Then, the washing buffer solution (6 mL), the blocking buffer solution (6 mL), and the PBS (6 mL) were sequentially flown. Thereafter, a 0.5 mg/mL ligand (4-Mal, 1 mL) PBS solution was flown through the column. The column was sealed and left for 30 minutes at room temperature. Thereafter, the PBS (5 mL) was flown so as to wash away an excess ligand.

(6–2 Affinity Chromatography)

The affinity column obtained in (6–1) was used to separate a protein which interacts with a ligand from a protein which does not interact with the ligand. The following three kinds of protein were used.

BSA (SIGMA ALUBMUN, BOVINE)
Concanavalin A (Con A, SEIKAGAKU KOGYO)
Pea Lectin (PSA, SEIKAGAKU KOGYO)

It is known from the SPR measurement result in (5-3) of Example 5 that Con A firmly binds to 4-Mal and dissociated by an aqueous solution of sodium hydroxide. It is also known that PSA and BSA do not specifically interact with 4-Mal.

Figure 7:
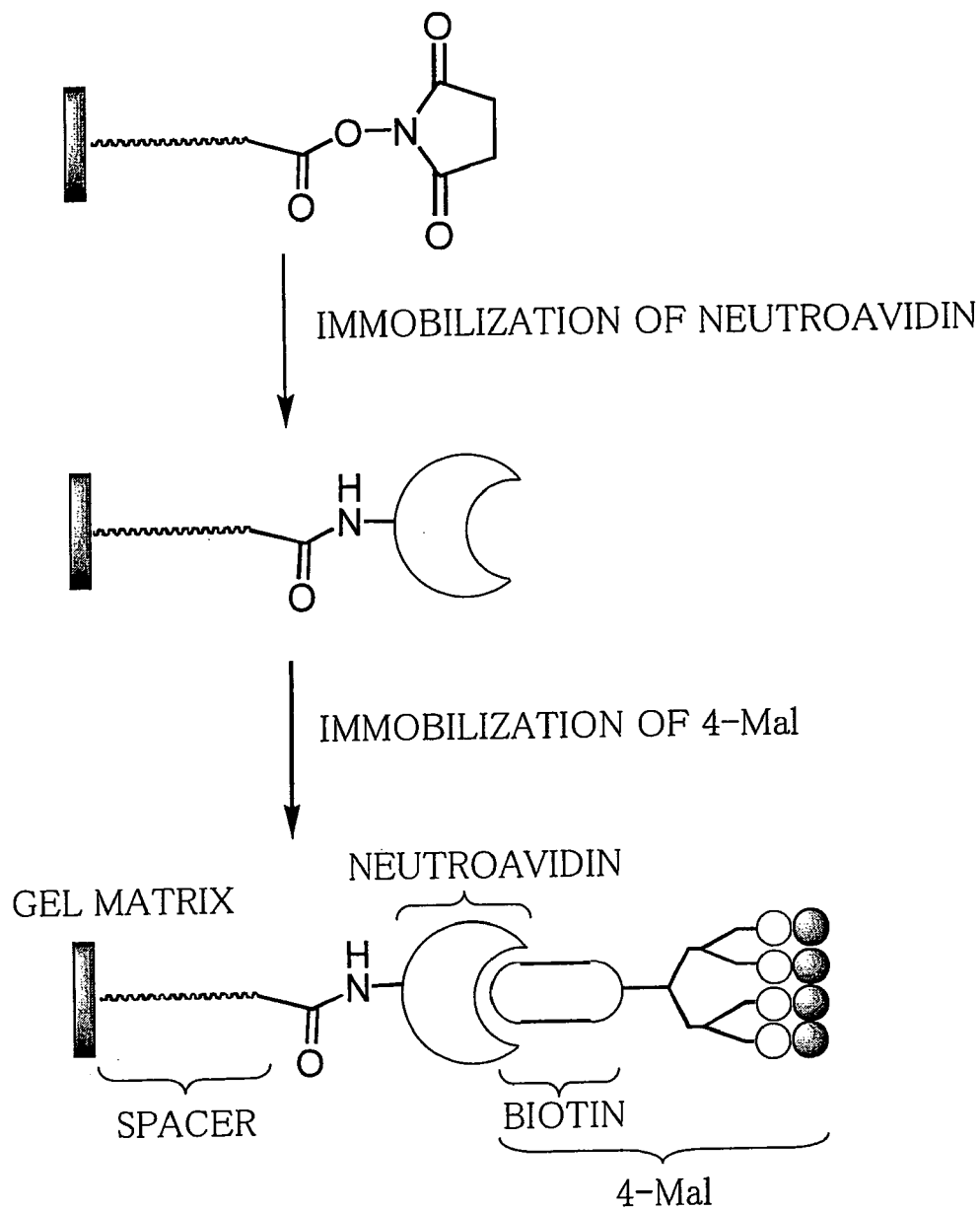
FIG. 7 is a diagram showing a step of making an affinity column which has a ligand carrier of the present invention.

It was expected from this that when a mixed solution of the proteins is flown through the affinity column, only Con A binds to 4-Mal to be retained by the column and the others pass through the column without stopping and are eluted. The retained Con A may be eluted by flowing a PBS solution containing sodium hydroxide through the column, or may be eluted by flowing a glucose solution serving as a binding-blocking reagent through the column. It is to be noted that the steps for affinity chromatography are shown in FIG. 7.

First, 1 mL of a protein-mixed PBS solution, so produced that the final concentration of each protein is 1 mM, was flown through the column produced in (6-1). The column was sealed and left for 5 minutes at room temperature.

Subsequently, PBS (5 mL) was flown through the column, and the elution thereof was collected by 1 mL (Mix-1.2.3.4.5). Next, 0.1 mM, 1.0 mM, 10 mM, and 1 M glucose PBS solutions serving as a dissociation reagent were sequentially flown by 5 mL, and the elution of each was collected by 1 mL (0.1 Glc-1 to 5, 1 Glc-1 to 5, 10 Glc-1 to 5, and 1000 Glc-1 to 5 in order). PBS (5 mL) was flown through the column so as to wash the column. Thereafter, a 10 mM sodium hydroxide PBS solution (5 mL) was flown through the column, and the elution thereof was collected by 1 mL (NaOH-1.2.3.4.5).

(6–3 Identification of a Protein)

Absorbance of the fractions collected by the affinity chromatography in (6-2) was measured at a wavelength of 280 nm using an ultraviolet spectrometer. The fractions in which absorption was recognized were subjected to SDS-PAGE.

First, the following solutions were produced. It is to be noted that all the solutions were used after filtration by a syringe filter (Millex-GS Syringe Driver Filter Unit 0.22 mm).

0.5 M Tris-HCl buffer solution pH 6.8
Electrophoretic-cell buffer solution (using an electrophoresis buffer solution manufactured by nacalai tesque)
Sample-adjusting buffer (SDS 0.3 mg, 2-mercaptoethanol 0.3 mL, glycerin 6 mL, 50 mM Tris-HCl buffer solution 3 mL, ion exchanged water 1 mL)
Marker pigment solution (bromphenol blue 1 mg, glycerin 0.1 mL, ion exchanged water 0.9 mL)
Coomassie brilliant blue stain solution (using a rapid stain CBB Kit manufactured by nacalai tesque)

The fractions (1 mL) so collected were freeze-dried and then mixed with the ion exchanged water (100 μL) so as to dissolve the fractions again. The resultant solution (20 μL) and a sample-adjusting buffer (10 μL) were mixed and heated at 95° C. for 10 minutes to adjust a sample solution. A ready-made gel (ATTO PAGEL-Compact AE-6000 (containing SDS 12.5%)) was set in an electrophoretic cell filled with the electrophoresis buffer solution. The marker pigment solution (1 μL) and the denatured sample solution (10 μL) were applied on each lane and electrophorased at a constant current of 20 mA. As a standard, Prestained protein marker. Low range (manufactured by nacalai tesque) was electrophorased simultaneously. The gel was taken out after the electrophoresis, immersed in the Coomassie brilliant blue stain solution, and shaken for 50 minutes at room temperature (using a Bio Dancer manufactured by New Brunswick Scientific Co., Ltd.). After the shaking, the gel was washed with the ion exchanged water and further immersed in the ion exchanged water at 60° C. for destaining. The gel so detained was dried for preservation.

Figure 8:
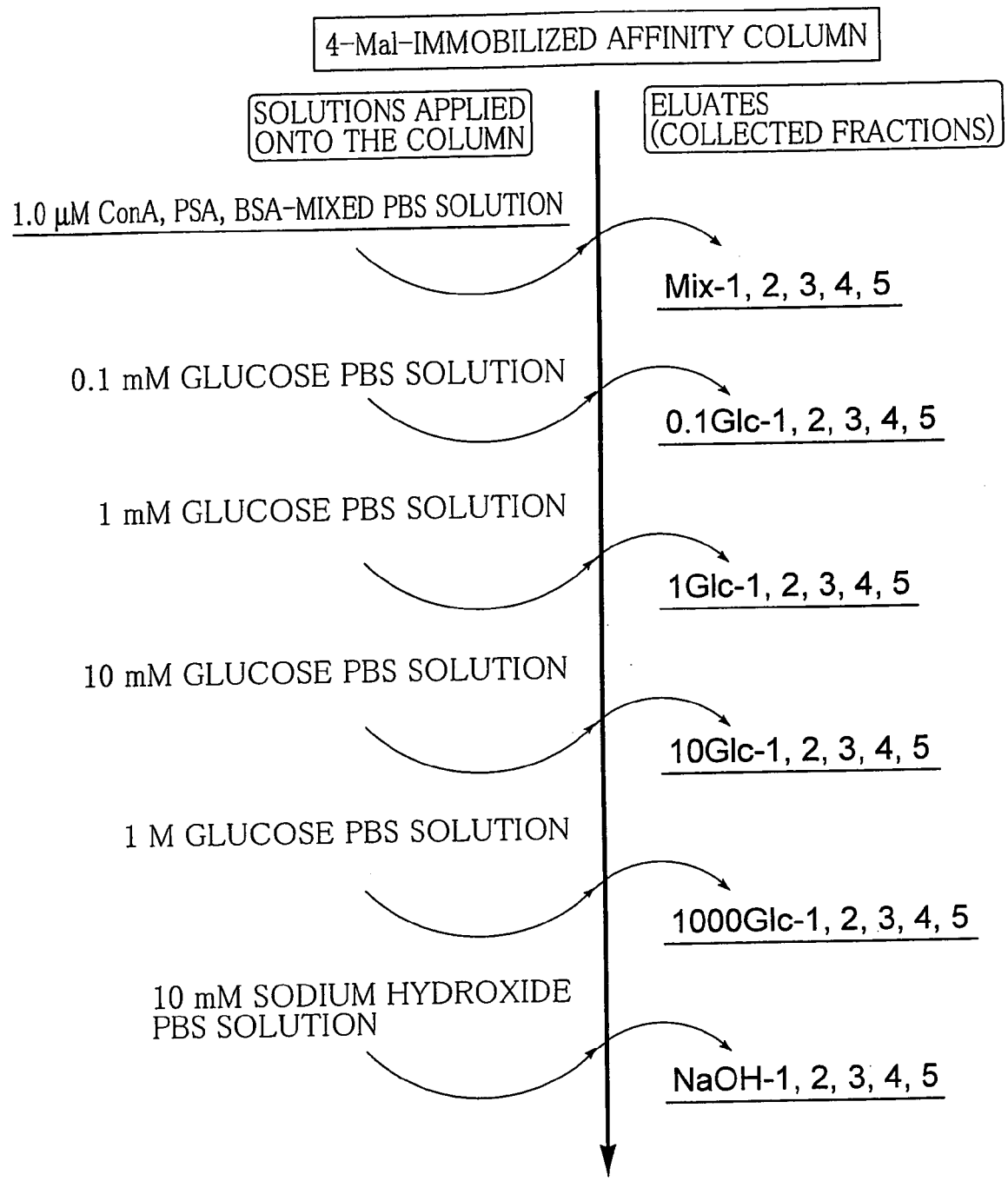
FIG. 8 is a diagram showing procedures for affinity chromatography.
Figure 9:
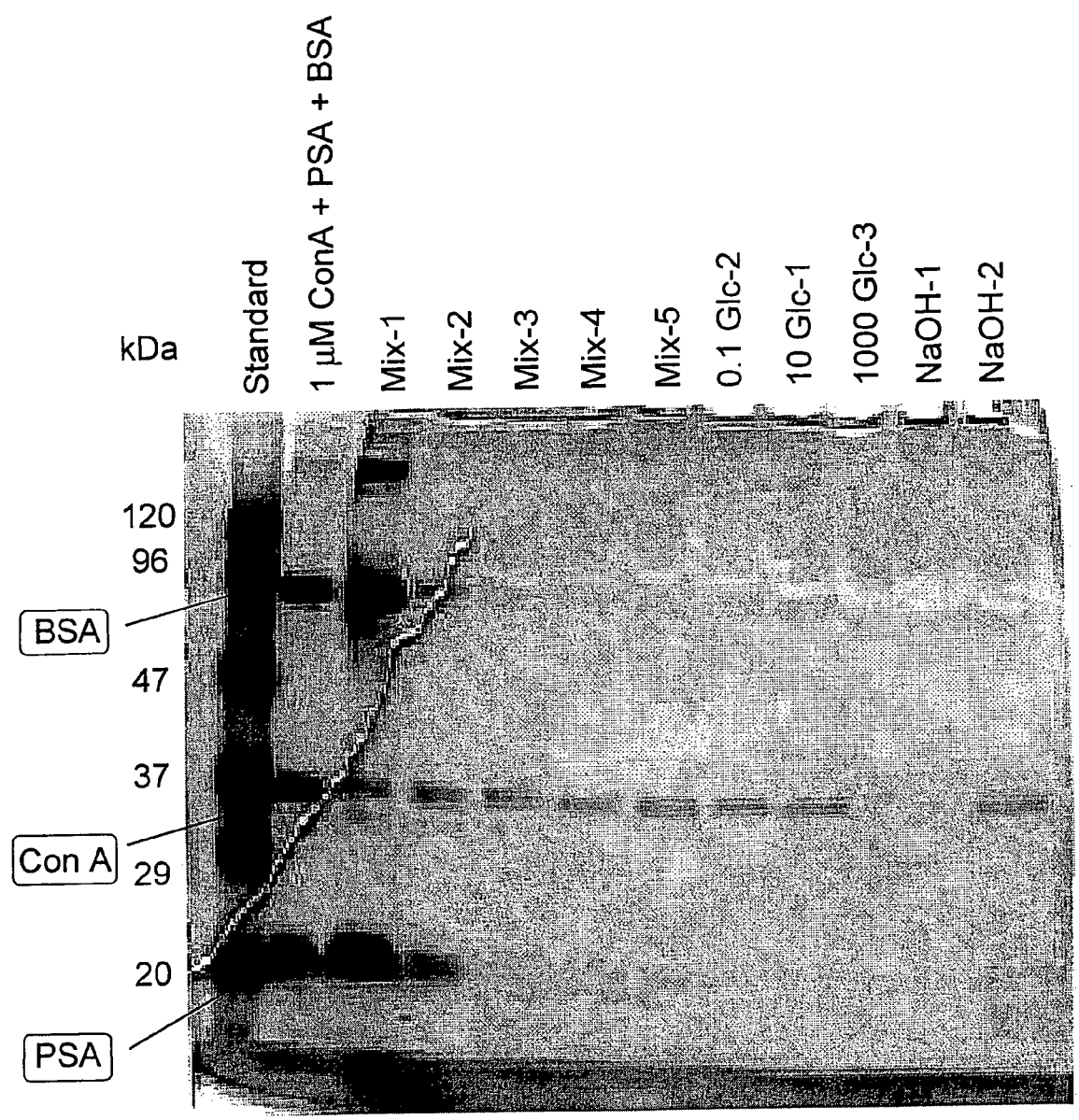
FIG. 9 is a diagram showing a result of SDS-PAGE for a bonding of 4-Mal with a protein.

Specifically, 12.5% acrylamide gel (ATTO PAGEL-Compact AE-6000) was used to perform SDS-PAGE, and Coomassie brilliant blue was used for dyeing, the result of which is shown in FIG. 8. FIG. 8 shows that three bands, Con A band, PSA band, and BSA band are detected in up to the Mix-2 fraction, and therefore indicates that Con A, PSA and BSA bands were eluted. In the Mix-3 fraction, BSA and PSA bands disappeared and only Con A band was detected. In the subsequent fractions, BSA and PSA bands were not detected, and Con A band was detected in all of the Mix-4, Mix-5, 10 Glc-1, and NaOH-2 fractions. The result yielded two findings.

(1) BSA and PSA passed through the column without being adsorbed. (Part of Con A, which was supposed to be absorbed, was eluted because the protein was applied in excess, and all the three proteins were detected also in the Mix-2 fraction.)

(2) A majority of Con A was retained by binding to 4-Mal on the carrier, and eluted from the column with an eluent.

As can be seen from the above result, an affinity column including 4-Mal immobilized thereon was used to selectively separate only Con A from a mixed solution of Con A, PSA, and BSA.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

As described above, a linker compound of the present invention has four aromatic amino groups serving as a moiety capable of taking in four or more units of sugar molecules, and has a biotin moiety or a iminobiotin moiety serving as a moiety capable of forming a bond with a protein-analyzing supporter used to detect and separate a protein which specifically interacts with a sugar molecule. Also, the linker compound is hardly affected by a nonspecific interaction with a protein.

Further, a ligand of the present invention includes the linker compound and a sugar molecule introduced thereinto.

Therefore, the present invention, using the linker compound and ligand, can be applied to the biotechnology industry to detect interactions of biomolecules. The present invention is particularly useful in fields where chip technology and an affinity column are used. The present invention is also useful in fields where a bioprobe and a biosensor are used. Other applicable fields of the invention include the pharmaceutical industry, and medical technology for diagnosis and inspections.

The invention claimed is:

1. A linker compound comprising a structure represented by following general formula (1),

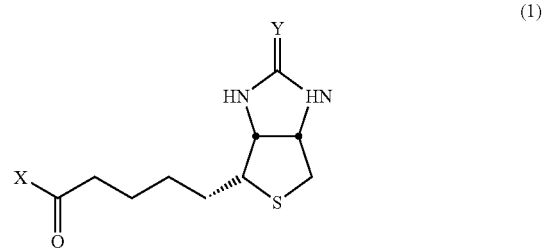

wherein Y has a structure represented by O or NH, and X has a structure represented by following general formula (2),

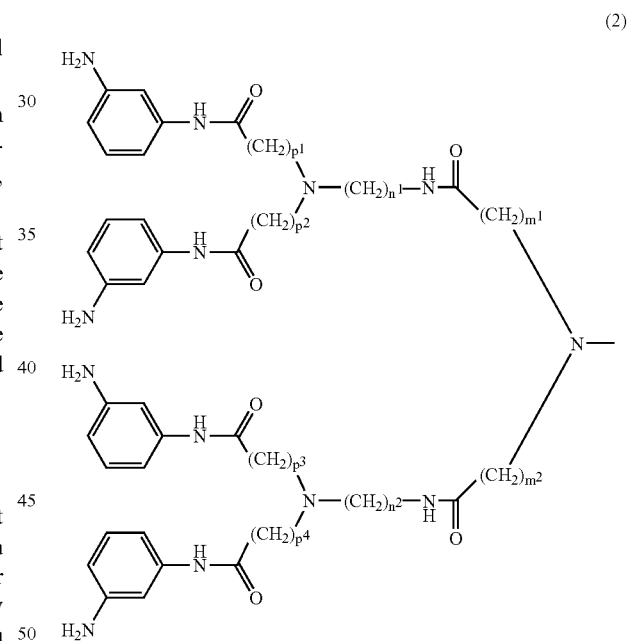

wherein $m^1$, $m^2$, $n^1$, $n^2$, $p^1$, $p^2$, $p^3$, and $p^4$ are independently integers of 1 to 6.

2. The linker compound according to claim 1, where $m^1$, $m^2$, $n^1$, $n^2$, $p^1$, $p^2$, $p^3$, and $p^4$ are all represented by 2 in the general formula (2).

3. A ligand which comprises the linker compound of claim 1 wherein a sugar molecule is linked to the aromatic amino group.

4. The ligand according to claim 3, wherein said sugar molecule is selected from the group consisting of a monosaccharide, an oligosaccharide, and a polysaccharide.

5. A ligand of a structure represented by following general formula (3), where $m^1$, $m^2$, $n^1$, $n^2$, $p^1$, $p^2$, $p^3$, and $p^4$ are independently integers of 1 to 6,

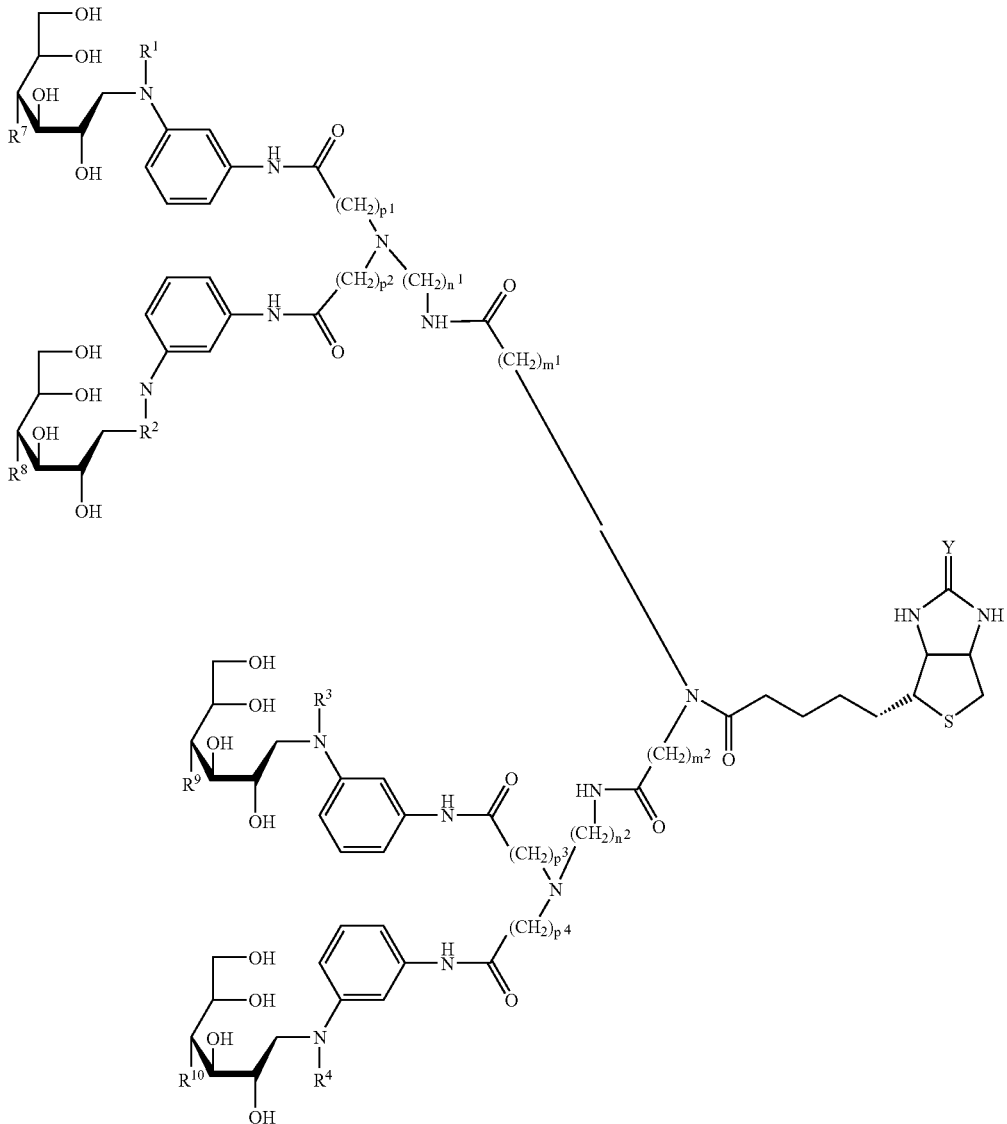
(3)
wherein Y has a structure represented by O or NH, and R¹, R², R³, and R⁴ independently have a structure represented by
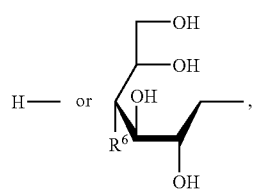
and R⁶, R⁷, R⁸, R⁹, and R¹⁰ have a structure selected from the group consisting of
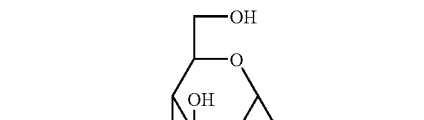
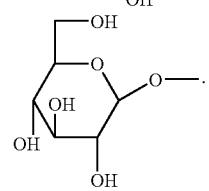

6. A ligand of a structure represented by following general formula (4), where Y has a structure represented by O or NH, and $m^1$, $m^2$, $n^1$, $n^2$, $p^1$, $p^2$, $p^3$, and $p^4$ are independently integers of 1 to 6.

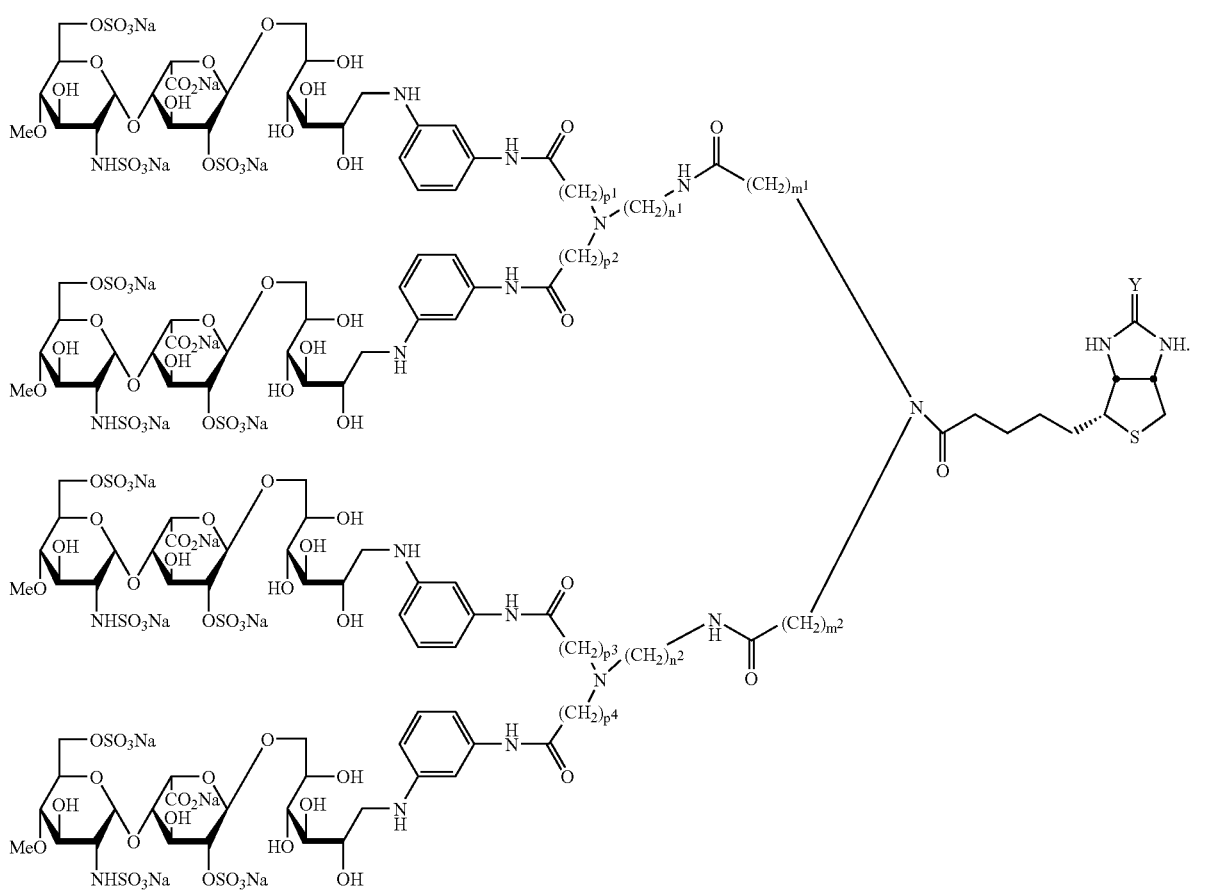

(4)

7. A method of immobilizing a ligand on a surface of a support, which comprises the step of allowing a solution containing the ligand of claim 3 to come into contact with the surface of the support having streptoavidin or avidin immobilized thereon.

8. A ligand carrier which comprises the ligand of claim 3 immobilized on a surface of a support having streptoavidin or avidin immobilized thereon.

9. The ligand carrier according to claim 8, wherein the support is a sensor chip for a surface plasmon resonance measurement.

10. The ligand carrier according to claim 8, wherein the support is an affinity chromatography carrier.

11. A method of immobilizing a ligand on a surface of a support, which comprises the step of allowing a solution containing the ligand of claim 5 to come into contact with the surface of the support having streptoavidin or avidin immobilized thereon.

12. A ligand carrier which comprises the ligand of claim 5 immobilized on a surface of a support having streptoavidin or avidin immobilized thereon.

13. The ligand carrier according to claim 12, wherein the support is a sensor chip for a surface plasmon resonance measurement.

14. The ligand carrier according to claim 12, wherein the support is an affinity chromatography carrier.

15. A method of immobilizing a ligand on a surface of a support, which comprises the step of allowing a solution containing the ligand of claim 5 to come into contact with the surface of the support having streptavidin or avidin immobilized thereon.

16. A ligand carrier which comprises the ligand of claim 5 immobilized on a surface of a support having streptoavidin or avidin immobilized thereon.

17. The ligand carrier according to claim 16, wherein the support is a sensor chip for a surface plasmon resonance measurement.

18. The ligand carrier according to claim 16, wherein the support is an affinity chromatography carrier.

* * * * *

UNITED STATES PATENT AND TRADEMARK OFFICE
CERTIFICATE OF CORRECTION

PATENT NO. : 7,183,067 B2
APPLICATION NO. : 10/526938
DATED : February 27, 2007
INVENTOR(S) : Yasuo Suda et al.

It is certified that error appears in the above-identified patent and that said Letters Patent is hereby corrected as shown below:

Col. 65, line 1, Formula (3) in claim 5 should be corrected as follows:

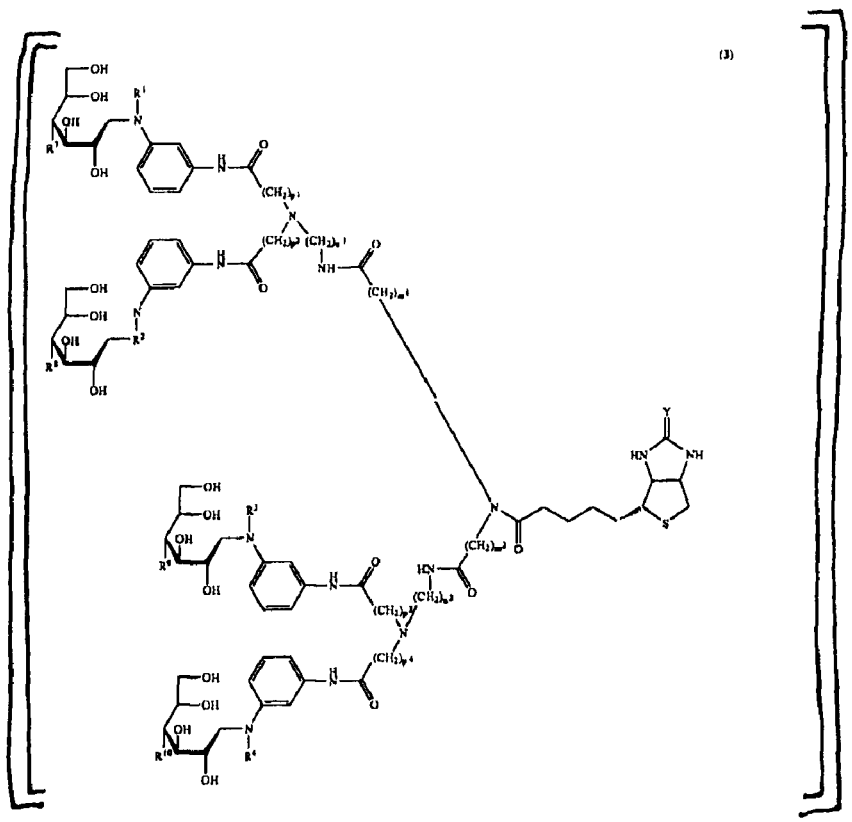

Signed and Sealed this

Eleventh Day of May, 2010

David J. Kappos
*Director of the United States Patent and Trademark Office*

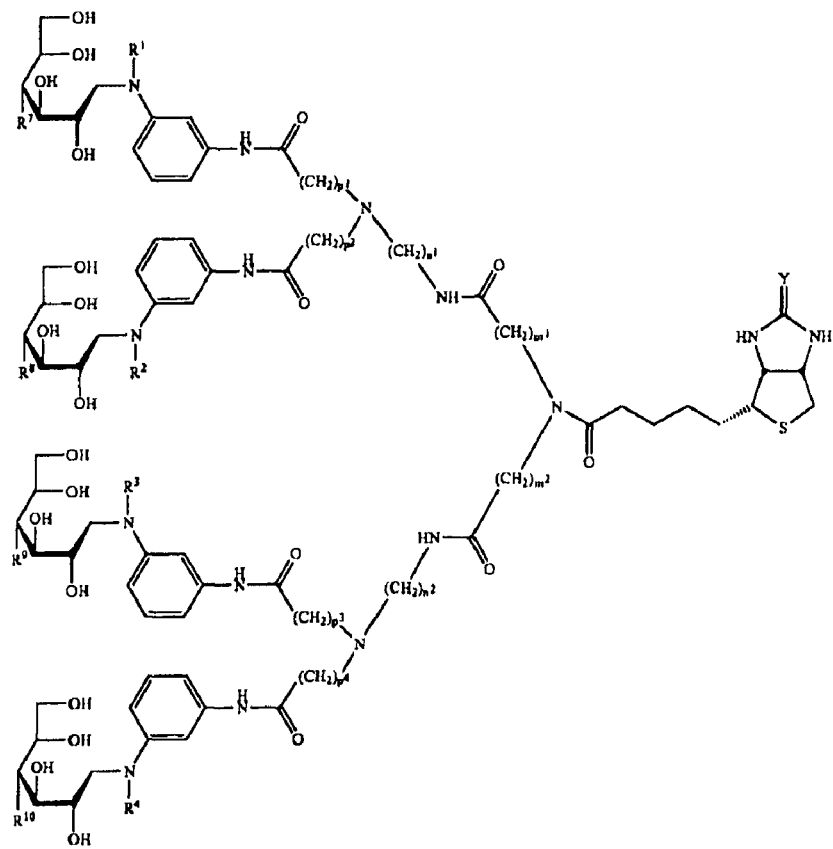
(J)